US011834640B2

(12) United States Patent
Cho et al.

(10) Patent No.: US 11,834,640 B2
(45) Date of Patent: Dec. 5, 2023

(54) DEVICE AND USES THEREOF FOR TREATING DIABETES

(71) Applicant: Board of Regents, The University of Texas System, Austin, TX (US)

(72) Inventors: Michael Cho, Arlington, TX (US); Caleb Liebman, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 424 days.

(21) Appl. No.: 17/021,771

(22) Filed: Sep. 15, 2020

(65) Prior Publication Data
US 2021/0079323 A1 Mar. 18, 2021

Related U.S. Application Data

(60) Provisional application No. 62/900,597, filed on Sep. 15, 2019.

(51) Int. Cl.
| | |
|---|---|
| *C12M 1/42* | (2006.01) |
| *C12M 1/00* | (2006.01) |
| *C12N 5/071* | (2010.01) |
| *A61K 35/39* | (2015.01) |

(52) U.S. Cl.
CPC ............... *C12M 1/42* (2013.01); *A61K 35/39* (2013.01); *C12M 23/34* (2013.01); *C12M 35/02* (2013.01); *C12N 5/0676* (2013.01); *C12N 2506/45* (2013.01); *C12N 2510/00* (2013.01)

(58) Field of Classification Search
CPC .......... C12M 1/42; C12M 35/02; A61K 35/39
See application file for complete search history.

(56) References Cited

FOREIGN PATENT DOCUMENTS

| WO | WO-2011062621 A2 * | 5/2011 | ............ C12M 21/08 |
| WO | WO-2017055421 A1 * | 4/2017 | |

OTHER PUBLICATIONS

Kim et al. Islet architecture: a comparative study. Islets 2009, 1;2:129-136. (Year: 2009).*
Pagliuca et al. Generation of functional pancreatic β cells in vitro. Cell 2014, 159;2:428-439. (Year: 2014).*
Suhariningsih et al. Permanent electric field, direct electric field, and infrared to reduce blood glucose level and hepatic function in mus musculus with diabetic mellitus. Journal of Physics: Conference Series 2017, 853:012024. (Year: 2017).*
Qiu et al. Microfluidic filter device with nylon mesh membranes efficiently dissociates cell aggregates and digested tissue into single cells. Lab on a Chip 2018, 18:2776. (Year: 2018).*
Chen et al. Advanced Near-Infrared Light for Monitoring and Modulating the Spatiotemporal Dynamics of Cell Functions in Living Systems. Advanced Science News 2020, 7:e1093783 (1-27). (Year: 2020).*
Adeghate et al. Effect of electrical field stimulation on insulin and glucagon secretion from the pancreas of normal and diabetic rats. Hormone and Metabolic Research 2001, 33:281-289. (Year: 2001).*
Adam-Vizi, Vera, and Anatoly A. Starkov. "Calcium and mitochondrial reactive oxygen species generation: how to read the facts." Journal of Alzheimer's disease 20.s2 (2010): S413-S426.
Ahrabi, Behnaz, et al. "The Effect of Photobiomodulation Therapy on the Differentiation, Proliferation, and Migration of the Mesenchymal Stem Cell: A Review." Journal of Lasers in Medical Sciences 10.Suppl 1 (2019): S96S-103.
Al-Adra, David P., et al. "Single-donor islet transplantation and long-term insulin independence in select patients with type 1 diabetes mellitus." Transplantation 98.9 (2014): 1007-1012.
Alessandra, Galli, et al. "Shaping Pancreatic β-Cell Differentiation and Functioning: The Influence of Mechanotransduction." Cells 9.2 (2020): 413.
Allen, Greg M., Alex Mogilner, and Julie A. Theriot. "Electrophoresis of cellular membrane components creates the directional cue guiding keratocyte galvanotaxis." Current Biology 23.7 (2013): 560-568.
Amaroli, Andrea, Sara Ferrando, and Stefano Benedicenti. "Photobiomodulation Affects Key Cellular Pathways of all Life-Forms: Considerations on Old and New Laser Light Targets and the Calcium Issue." Photochemistry and photobiology 95.1 (2019): 455-459.
Amon, A., and F. Alesch. "Systems for deep brain stimulation: review of technical features." Journal of Neural Transmission 124.9 (2017): 1083-1091.
Arava, Yoav, Rony Seger, and Michael D. Walker. "Grfβ, a novel regulator of calcium signaling, is expressed in pancreatic beta cells and brain." Journal of Biological Chemistry 274.35 (1999): 24449-24452.
Balke, C. William, Terrance M. Egan, and W. G. Wier. "Processes that remove calcium from the cytoplasm during excitation-contraction coupling in intact rat heart cells." The Journal of physiology 474.3 (1994): 447-462.
Bardaweel, Sanaa K., et al. "Reactive oxygen species: the dual role in physiological and pathological conditions of the human body." The Eurasian Journal of Medicine 50.3 (2018): 193-201.
Bartos, Adam, et al. "Pre-conditioning with near infrared photobiomodulation reduces inflammatory cytokines and markers of oxidative stress in cochlear hair cells." Journal of biophotonics 9.11-12 (2016): 1125-1135.
Baz, Baz, Jean-Pierre Riveline, and Jean-Francoise Gautier. "Gestational diabetes mellitus: definition, aetiological and clinical aspects." Eur J Endocrinol 174.2 (2016): R43-51.
Beebe, Stephen J., et al. "Nanosecond pulsed electric fields modulate cell function through intracellular signal transduction mechanisms." Physiological measurement 25.4 (2004): 1077-1093.
Benninger, Richard KP, et al. "Gap junction coupling and calcium waves in the pancreatic islet." Biophysical journal 95.11 (2008): 5048-5061.

(Continued)

*Primary Examiner* — Allison M Fox
*Assistant Examiner* — Jennifer S Spence
(74) *Attorney, Agent, or Firm* — Meunier Carlin & Curfman LLC

(57) ABSTRACT

Disclosed are devices for improving viability of isolated islets or β-cells and stimulating insulin production from isolated islets or β-cells and uses thereof for treating type 1 diabetes.

16 Claims, 23 Drawing Sheets

(56) References Cited

OTHER PUBLICATIONS

Bensellam, Mohammed, Jean-Christophe Jonas, and D. Ross Laybutt. "Mechanisms of β-cell dedifferentiation in diabetes: recent findings and future research directions." Journal of Endocrinology 236.2 (2018): R109-R143.
Berridge, Michael J., Martin D. Bootman, and H. Llewelyn Roderick. "Calcium signalling: dynamics, homeostasis and remodelling." Nature reviews Molecular cell biology 4.7 (2003): 517-529.
Bertram, Richard, Arthur Sherman, and Leslie S. Satin. "Electrical bursting, calcium oscillations, and synchronization of pancreatic islets." The Islets of Langerhans. Springer, Dordrecht, 2010. 261-279.
Bluestone, Jeffrey A., Kevan Herold, and George Eisenbarth. "Genetics, pathogenesis and clinical interventions in type 1 diabetes." Nature 464.7293 (2010): 1293-1300.
Boucher, Marie-Josée, et al. "Phosphorylation marks IPF1/PDX1 protein for degradation by glycogen synthase kinase 3-dependent mechanisms." Journal of Biological Chemistry 281.10 (2006): 6395-6403.
Braun, Matthias, et al. "Voltage-gated ion channels in human pancreatic β-cells: electrophysiological characterization and role in insulin secretion." Diabetes 57.6 (2008): 1618-1628.
Brini, Marisa, and Ernesto Carafoli. "The plasma membrane Ca2+ ATPase and the plasma membrane sodium calcium exchanger cooperate in the regulation of cell calcium." Cold Spring Harbor perspectives in biology 3.2 (2011): a004168.
Brookes, Paul S., et al. "Calcium, ATP, and ROS: a mitochondrial love-hate triangle." American Journal of Physiology—Cell Physiology 287.4 (2004): C817-C833.
Brown, Guy C. "Regulation of mitochondrial respiration by nitric oxide inhibition of cytochrome c oxidase." Biochimica et Biophysica Acta (BBA)—Bioenergetics 1504.1 (2001): 46-57.
Brüning, Dennis, et al. "Glucose but not KCl diminishes submembrane granule turnover in mouse beta-cells." Journal of Molecular Endocrinology 59.3 (2017): 311-324.
Camello-Almaraz, Cristina, et al. "Mitochondrial reactive oxygen species and Ca2+ signaling." American Journal of Physiology—Cell Physiology 291.5 (2006): C1082-C1088.
Catterall, William A. "Voltage-gated calcium channels." Cold Spring Harbor perspectives in biology 3.8 (2011): a003947.
Cerf, Marlon E. "Beta cell dysfunction and insulin resistance." Frontiers in endocrinology 4 (2013): 37.
Chao, Pen-hsiu Grace, et al. "Effects of applied DC electric field on ligament fibroblast migration and wound healing." Connective tissue research 48.4 (2007): 188-197.
Chay, Teresa Ree. "Effects of extracellular calcium on electrical bursting and intracellular and luminal calcium oscillations in insulin secreting pancreatic beta-cells." Biophysical Journal 73.3 (1997): 1673-1688.
Chen, Bo, et al. "Astrocyte Viability and Functionality in Spatially Confined Microcavitation Zone." ACS applied materials & interfaces 11.5 (2019): 4889-4899.
Chen, Jing-Bo, et al. "Multiple Ca2+ signaling pathways regulate intracellular Ca2+ activity in human cardiac fibroblasts." Journal of cellular physiology 223.1 (2010): 68-75.
Chen, Kejing, Roland N. Pittman, and Aleksander S. Popel. "Nitric oxide in the vasculature: where does it come from and where does it go? A quantitative perspective." Antioxidants & redox signaling 10.7 (2008): 1185-1198.
Chen, Shuibing, et al. "A small molecule that directs differentiation of human ESCs into the pancreatic lineage." Nature chemical biology 5.4 (2009): 258-265.
Cho, Michael R., et al. "Control of calcium entry in human fibroblasts by frequency-dependent electrical stimulation." Front Biosci 7.1 (2002): 1-8.
Cho, Michael R., et al. "Membrane dynamics of the water transport protein aquaporin-1 in intact human red cells." Biophysical journal 76.2 (1999): 1136-1144.
Cho, Michael R., et al. "Induced redistribution of cell surface receptors by alternating current electric fields." The FASEB journal 8.10 (1994): 771-776.
Clapham, David E. "Calcium signaling." Cell 131.6 (2007): 1047-1058.
Colberg, Sheri R., et al. "Exercise and type 2 diabetes: the American College of Sports Medicine and the American Diabetes Association: joint position statement executive summary." Diabetes care 33.12 (2010): 2692-2696.
Colsoul, Barbara, et al. "Loss of high-frequency glucose-induced Ca2+ oscillations in pancreatic islets correlates with impaired glucose tolerance in Trpm5−/− mice." Proceedings of the National Academy of Sciences 107.11 (2010): 5208-5213.
Colton, C. K., and M. X. Zhu. "2-Aminoethoxydiphenyl borate as a common activator of TRPV1, TRPV2, and TRPV3 channels." Transient Receptor Potential (TRP) Channels. Springer, Berlin, Heidelberg, 2007. 173-187.
Connolly, Vincent, et al. "Diabetes prevalence and socioeconomic status: a population based study showing increased prevalence of type 2 diabetes mellitus in deprived areas." Journal of Epidemiology & Community Health 54.3 (2000): 173-177.
Cox, Carly S., et al. "Mitohormesis in mice via sustained basal activation of mitochondrial and antioxidant signaling." Cell metabolism 28.5 (2018): 776-786.
Daoud, Jamal, et al. "The effect of extracellular matrix components on the preservation of human islet function in vitro." Biomaterials 31.7 (2010): 1676-1682.
Daoud, Jamal, Lawrence Rosenberg, and Maryam Tabrizian. "Pancreatic islet culture and preservation strategies: advances, challenges, and future outlook." Cell transplantation 19.12 (2010): 1523-1535.
De Freitas, Lucas Freitas, and Michael R. Hamblin. "Proposed mechanisms of photobiomodulation or low-level light therapy." IEEE Journal of selected topics in quantum electronics 22.3 (2016): 348-364.
Dean, P. M. "Ultrastructural morphometry of the pancreatic β-cell." Diabetologia 9.2 (1973): 115-119.
Dittami, Gregory M., et al. "Intracellular calcium transients evoked by pulsed infrared radiation in neonatal cardiomyocytes." The Journal of physiology 589.6 (2011): 1295-1306.
Docherty, R. J., J. C. Yeats, and A. S. Piper. "Capsazepine block of voltage-activated calcium channels in adult rat dorsal root ganglion neurones in culture." British journal of pharmacology 121.7 (1997): 1461-67.
Dolenšek, Jurij, et al. "Glucose-dependent activation, activity, and deactivation of beta cell networks in acute mouse pancreas tissue slices." bioRxiv (2020). Preprint available at: https://doi.org/10.1101/2020.03.11.986893.
Dolmetsch, Ricardo E., et al. "Differential activation of transcription factors induced by Ca 2+ response amplitude and duration." Nature 386.6627 (1997): 855-858.
Dolmetsch, Ricardo E., Keli Xu, and Richard S. Lewis. "Calcium oscillations increase the efficiency and specificity of gene expression." Nature 392.6679 (1998): 933-936.
Dröse, Stefan, and Ulrich Brandt. "Molecular mechanisms of superoxide production by the mitochondrial respiratory chain." Mitochondrial oxidative phosphorylation. Springer, New York, NY, 2012. 145-169.
Enomoto, Masahiro, et al. "From stores to sinks: structural mechanisms of cytosolic calcium regulation." Membrane Dynamics and Calcium Signaling. Springer, Cham, 2017. 215-251.
Fan, L., et al., "Brief review of image denoising techniques". Visual Computing for Industry, Biomedicine, and Art, 2019; 2(7).
Farnsworth, Nikki L., and Richard KP Benninger. "New insights into the role of connexins in pancreatic islet function and diabetes." FEBS letters 588.8 (2014): 1278-1287.
Ferrandiz-Huertas, Clotilde, et al. "Trafficking of thermoTRP channels." Membranes 4.3 (2014): 525-564.
Fridlyand, Leonid E., and Louis H. Philipson. "Glucose sensing in the pancreatic beta cell: a computational systems analysis." Theoretical Biology and Medical Modelling 7.1 (2010): 15.
Fridlyand, Leonid E., Natalia Tamarina, and Louis H. Philipson. "Modeling of Ca2+ flux in pancreatic β-cells: role of the plasma

(56) References Cited

OTHER PUBLICATIONS membrane and intracellular stores." American Journal of Physiology—Endocrinology and Metabolism 285.1 (2003): E138-E154.
Fridlyand, Leonid E., N. Tamarina, and Louis H. Philipson. "Bursting and calcium oscillations in pancreatic β-cells: specific pacemakers for specific mechanisms." American Journal of Physiology-Endocrinology and Metabolism 299.4 (2010): E517-E532.
Funk, Richard HW. "Endogenous electric fields as guiding cue for cell migration." Frontiers in physiology 6 (2015): 143. https://doi.org/10.3389/fphys.2015.00143/full.
Gamble, Anissa, et al. "The journey of islet cell transplantation and future development." Islets 10.2 (2018): 80-94.
García-Montalvo, Eliud A., Hugo Reyes-Pérez, and Luz M. Del Razo. "Fluoride exposure impairs glucose tolerance via decreased insulin expression and oxidative stress." Toxicology 263.2-3 (2009): 75-83.
Gees, Maarten, Barbara Colsoul, and Bernd Nilius. "The role of transient receptor potential cation channels in Ca2+ signaling." Cold Spring Harbor perspectives in biology 2.10 (2010): a003962.
German, Michael S. "Glucose sensing in pancreatic islet beta cells: the key role of glucokinase and the glycolytic intermediates." Proceedings of the National Academy of Sciences 90.5 (1993): 1781-1785.
Ghafourifar, Pedram, and Enrique Cadenas. "Mitochondrial nitric oxide synthase." Trends in pharmacological sciences 26.4 (2005): 190-195.
Gilon, Patrick, et al. "Control mechanisms of the oscillations of insulin secretion in vitro and in vivo." Diabetes 51.suppl 1 (2002): S144-S151.
Giorgi, Carlotta, et al. "Calcium dynamics as a machine for decoding signals." Trends in cell biology 28.4 (2018): 258-273.
Giugni, Terrence D., Daniel L. Braslau, and Harry T. Haigler. "Electric field-induced redistribution and postfield relaxation of epidermal growth factor receptors on A431 cells." The Journal of cell biology 104.5 (1987): 1291-1297.
Gloyn, Anna L. "Glucokinase (GCK) mutations in hyper-and hypoglycemia: maturity-onset diabetes of the young, permanent neonatal diabetes, and hyperinsulinemia of infancy." Human mutation 22.5 (2003): 353-362.
Görlach, Agnes, et al. "Calcium and ROS: a mutual interplay." Redox biology 6 (2015): 260-271.
Guigas, Bruno, et al. "5-Aminoimidazole-4-Carboxamide-1-β-d-Ribofuranoside and Metformin Inhibit Hepatic Glucose Phosphorylation by an AMP-Activated Protein Kinase-Independent Effect on Glucokinase Translocation." Diabetes 55.4 (2006): 865-874.
Haltaufderhyde, Kirk, et al. "Opsin expression in human epidermal skin." Photochemistry and photobiology 91.1 (2015): 117-123.
Hamblin, Michael R. "Photobiomodulation or low-level laser therapy." Journal of biophotonics 9.11-12 (2016): 1122-1124.
Hamblin, Michael R. "Mechanisms and applications of the anti-inflammatory effects of photobiomodulation." AIMS biophysics 4.3 (2017): 337-361.
Hamblin, Michael R. "Mechanisms and mitochondrial redox signaling in photobiomodulation." Photochemistry and photobiology 94.2 (2018): 199-212.
Hannanta-anan, Pimkhuan, and Brian Y. Chow. "Optogenetic control of calcium oscillation waveform defines NFAT as an integrator of calcium load." Cell systems 2.4 (2016): 283-288.
Heit, Jeremy J., et al. "Calcineurin/NFAT signalling regulates pancreatic β-cell growth and function." Nature 443.7109 (2006): 345-349.
Henquin, Jean-Claude, Nizar I. Mourad, and Myriam Nenquin. "Disruption and stabilization of β-cell actin microfilaments differently influence insulin secretion triggered by intracellular Ca2+ mobilization or store-operated Ca2+ entry." FEBS letters 586.1 (2012): 89-95.
Henquin, Jean-Claude, et al. "In vitro insulin secretion by pancreatic tissue from infants with diazoxide-resistant congenital hyperinsulinism deviates from model predictions." The Journal of clinical investigation 121.10 (2011) 3932-3942.
Hogan, Patrick G., et al. "Transcriptional regulation by calcium, calcineurin, and NFAT." Genes & development 17.18 (2003): 2205-2232.
Hopyan, Sevan. "Biophysical regulation of early limb bud morphogenesis." Developmental Biology 429.2 (2017): 429-433.
Houreld, Nicolette N., Roland T. Masha, and Heidi Abrahamse. "Low-intensity laser irradiation at 660 nm stimulates cytochrome c oxidase in stressed fibroblast cells." Lasers in surgery and medicine 44.5 (2012): 429-434.
Irani, S., et al. "Effect of low-level laser irradiation on in vitro function of pancreatic islets." Transplantation proceedings. vol. 41. No. 10. Elsevier, 2009, 4313-4315.
Jitrapakdee, S., et al. "Regulation of insulin secretion: role of mitochondrial signalling." Diabetologia 53.6 (2010): 1019-1032.
Johnston, Natalie R., et al. "Beta cell hubs dictate pancreatic islet responses to glucose." Cell metabolism 24.3 (2016): 389-401.
Jope, Richard S., Christopher J. Yuskaitis, and Eléonore Beurel. "Glycogen synthase kinase-3 (GSK3): inflammation, diseases, and therapeutics." Neurochemical research 32.4-5 (2007): 577-595.
Kahl, Christina R., and Anthony R. Means. "Regulation of cell cycle progression by calcium/calmodulin-dependent pathways." Endocrine reviews 24.6 (2003): 719-736.
Kahn, Steven E., Mark E. Cooper, and Stefano Del Prato. "Pathophysiology and treatment of type 2 diabetes: perspectives on the past, present, and future." The Lancet 383.9922 (2014): 1068-1083.
Kajiyama, Hiromitsu, et al. "Pdx1-transfected adipose tissue-derived stem cells differentiate into insulin-producing cells in vivo and reduce hyperglycemia in diabetic mice." International Journal of Developmental Biology 54.4 (2009): 699-705.
Kaneto, Hideaki, et al. "Role of reactive oxygen species in the progression of type 2 diabetes and atherosclerosis." Mediators of inflammation 2010 1-11.
Kang, H., et al. "Glucose metabolism and oscillatory behavior of pancreatic islets." Physical Review E 72.5 (2005): 051905.
Karu, T., "Cellular and Molecular Mechanisms of Photobiomodulation (Low-Power Laser Therapy)". IEEE Journal of Selected Topics in Quantum Electronics, 2014, 20(2), pp. 143-148.
Kass, G. E., and Sten Orrenius. "Calcium signaling and cytotoxicity." Environmental Health Perspectives 107.suppl 1 (1999): 25-35.
Kazanietz, Marcelo G., et al. "Characterization of ligand and substrate specificity for the calcium-dependent and calcium-independent protein kinase C isozymes." Molecular Pharmacology 44.2 (1993): 298-307.
Kindzelskii, Andrei L., and Howard R. Petty. "Ion channel clustering enhances weak electric field detection by neutrophils: apparent roles of SKF96365-sensitive cation channels and myeloperoxidase trafficking in cellular responses." European Biophysics Journal 35.1 (2005): 1-26.
Kloth, Luther C. "Electrical stimulation for wound healing: a review of evidence from in vitro studies, animal experiments, and clinical trials." The international journal of lower extremity wounds 4.1 (2005): 23-44.
Koga, Tomoaki, et al. "Mild electrical stimulation with heat shock guides differentiation of embryonic stem cells into Pdx1-expressing cells within the definitive endoderm." BMC biotechnology 17.1 (2017): 1-7.
Kondo, Tatsuya, et al. "Hyperthermia with mild electrical stimulation protects pancreatic β-cells from cell stresses and apoptosis." Diabetes 61.4 (2012): 838-847.
Koyanagi, Masamichi, et al. "Wnt5a increases cardiac gene expressions of cultured human circulating progenitor cells via a PKC delta activation." PloS one 4.6 (2009): e5765.
Kushner, Jake A., et al. "Pdx1 restores β cell function in Irs2 knockout mice." The Journal of clinical investigation 109.9 (2002): 1193-1201.
Lawlor, Nathan, et al. "Alpha TC1 and Beta-TC-6 genomic profiling uncovers both shared and distinct transcriptional regulatory features with their primary islet counterparts." Scientific reports 7.1 (2017): 1-14.
Lawrence, Michael C., Harshika S. Bhatt, and Richard A. Easom. "NFAT regulates insulin gene promoter activity in response to synergistic pathways induced by glucose and glucagon-like peptide-1." Diabetes 51.3 (2002): 691-698.

(56) References Cited

OTHER PUBLICATIONS

Lawrence, Michael C., et al. "NFAT targets signaling molecules to gene promoters in pancreatic β-cells." Molecular endocrinology 29.2 (2015): 274-288.

Lee, Kendall H., et al. "Neurotransmitter release from high-frequency stimulation of the subthalamic nucleus." Journal of neurosurgery 101.3 (2004): 511-517.

Leloup, Corinne, et al. "Mitochondrial reactive oxygen species are obligatory signals for glucose-induced insulin secretion." Diabetes 58.3 (2009): 673-681.

Levin, Michael. "Molecular bioelectricity: how endogenous voltage potentials control cell behavior and instruct pattern regulation in vivo." Molecular biology of the cell 25.24 (2014): 3835-3850.

Li, Fang-Hui, et al. "Photobiomodulation on Bax and Bcl-2 Proteins and SIRT1/PGC-1α Axis mRNA Expression Levels of Aging Rat Skeletal Muscle." International Journal of Photoenergy 2014 (2014), 1-8.

Li, Li, and Jianxin Jiang. "Stem cell niches and endogenous electric fields in tissue repair." Frontiers of Medicine 5.1 (2011): 40-44.

Li, Wan-Chun, et al. "In vitro transdifferentiation of hepatoma cells into functional pancreatic cells." Mechanisms of development 122.6 (2005): 835-847.

Li, Zhushi, et al. "ROS leads to MnSOD upregulation through ERK2 translocation and p53 activation in selenite-induced apoptosis of NB4 cells." FEBS letters 584.11 (2010): 2291-2297.

Liang, Jiangang, Lei Liu, and Da Xing. "Photobiomodulation by low-power laser irradiation attenuates Aβ-induced cell apoptosis through the Akt/GSK3β/β-catenin pathway." Free Radical Biology and Medicine 53.7 (2012): 1459-1467.

Liebano, Richard Eloin, and Aline Fernanda Perez Machado. "Vascular endothelial growth factor release following electrical stimulation in human subjects." Advances in wound care 3.2 (2014): 98-103.

Liebman, Caleb, et al. "Altered β-Cell Calcium Dynamics via Electric Field Exposure." Annals of Biomedical Engineering (2020): 1-9.

Lim, Jinhwan, et al. "Effects of low-level light therapy on hepatic antioxidant defense in acute and chronic diabetic rats." Journal of biochemical and molecular toxicology 23.1 (2009): 1-8.

Lin-Liu, S., W. R. Adey, and M. M. Poo. "Migration of cell surface concanavalin A receptors in pulsed electric fields." Biophysical journal 45.6 (1984): 1211-1217.

Liu, Bo, et al. "The CaMK4/CREB/IRS-2 cascade stimulates proliferation and inhibits apoptosis of β-cells." PLoS One 7.9 (2012): e45711.

Llanos, Paola, et al. "Glucose-dependent insulin secretion in pancreatic β-cell islets from male rats requires Ca 2+ release via ROS-stimulated ryanodine receptors." PLoS One 10.6 (2015): e0129238.

Love, Maria R., et al. "Effects of electrical stimulation on cell proliferation and apoptosis." Journal of cellular physiology 233.3 (2018): 1860-1876.

Marhl, Marko, et al. "Complex calcium oscillations and the role of mitochondria and cytosolic proteins." Biosystems 57.2 (2000): 75-86.

Markwardt, Michele L., Kendra M. Seckinger, and Mark A. Rizzo. "Regulation of glucokinase by intracellular calcium levels in pancreatic β cells." Journal of Biological Chemistry 291.6 (2016): 3000-3009.

Mason, Maria G., Peter Nicholls, and Chris E. Cooper. "Re-evaluation of the near infrared spectra of mitochondrial cytochrome c oxidase: implications for non invasive in vivo monitoring of tissues." Biochimica et Biophysica Acta (BBA)—Bioenergetics 1837.11 (2014): 1882-1891.

Mathieu, Chantal, et al. "Effect of once weekly dulaglutide by baseline beta-cell function in people with type 2 diabetes in the Award programme." Diabetes, Obesity and Metabolism 20.8 (2018): 2023-2028.

Matschinsky, Franz M. "Regulation of pancreatic β-cell glucokinase: from basics to therapeutics." Diabetes 51. suppl 3 (2002): S394-S404.

McCaig, Colin D., et al. "Controlling cell behavior electrically: current views and future potential." Physiological reviews (2005), 943-978.

McColloch, Andrew, et al. "Alterted Adipogenesis of Human Mesenchymal Stem Cells by Photobiomodulation Using 1064 nm Laser Light." Lasers in Surgery and Medicine (2020).

De Meulenaer, Eric Cordemans, et al. "Effects of infrared light on insulin release, cationic fluxes and cellularity in insulin-producing cells." Metabolic and Functional Research on Diabetes (Online) vol. 2 (2009): 63-70.

Miller, Jonathan P., et al. "Parameters of spinal cord stimulation and their role in electrical charge delivery: a review." Neuromodulation: Technology at the Neural Interface 19.4 (2016): 373-384.

Mogami, Hideo, et al. "Calcium binding capacity of the cytosol and endoplasmic reticulum of mouse pancreatic acinar cells." The Journal of physiology 518.2 (1999): 463-467.

Moreau, David, et al. "Infrared neural stimulation induces intracellular Ca2+ release mediated by phospholipase C." Journal of biophotonics 11.2 (2018): e201700020.

Morth, J. Preben, et al. "A structural overview of the plasma membrane Na+, K+-ATPase and H+-ATPase ion pumps." Nature reviews Molecular cell biology 12.1 (2011): 60-70.

Murphy, Michael P. "How mitochondria produce reactive oxygen species." Biochemical journal 417.1 (2009): 1-13.

Murphy, Rinki, Sian Ellard, and Andrew T. Hattersley. "Clinical implications of a molecular genetic classification of monogenic β-cell diabetes." Nature clinical practice Endocrinology & metabolism 4.4 (2008): 200-213.

Mycielska, Maria E., and Mustafa BA Djamgoz. "Cellular mechanisms of direct-current electric field effects: galvanotaxis and metastatic disease." Journal of cell science 117.9 (2004): 1631-1639.

Nuccitelli, Richard. "Endogenous electric fields in embryos during development, regeneration and wound healing." Radiation protection dosimetry 106.4 (2003): 375-383.

Nurković, Jasmin, et al. "Combined effects of electromagnetic field and low-level laser increase proliferation and alter the morphology of human adipose tissue-derived mesenchymal stem cells." Lasers in medical science 32.1 (2017): 151-160.

Pai, Vaibhav P., et al. "Endogenous gradients of resting potential instructively pattern embryonic neural tissue via notch signaling and regulation of proliferation." Journal of Neuroscience 35.10 (2015): 4366-4385.

Pall, Martin L. "Electromagnetic fields act via activation of voltage-gated calcium channels to produce beneficial or adverse effects." Journal of cellular and molecular medicine 17.8 (2013): 958-965.

Pannala, Venkat R., Amadou KS Camara, and Ranjan K. Dash. "Modeling the detailed kinetics of mitochondrial cytochrome c oxidase: Catalytic mechanism and nitric oxide inhibition." Journal of applied physiology 121.5 (2016): 1196-1207.

Paschou, Stavroula A., et al. "On type 1 diabetes mellitus pathogenesis." Endocrine connections 7.1 (2018): R38-R46.

Passarella, Salvatore, and Tiina Karu. "Absorption of monochromatic and narrow band radiation in the visible and near IR by both mitochondrial and non-mitochondrial photoacceptors results in photobiomodulation." Journal of Photochemistry and Photobiology B: Biology 140 (2014): 344-358.

Pathak, Trayambak, and Mohamed Trebak. "Mitochondrial Ca2+ signaling." Pharmacology & therapeutics 192 (2018): 112-123.

Peplow, Philip V., and G. David Baxter. "Defining a therapeutic window for laser irradiation (810 nm) applied to the inguinal region to ameliorate diabetes in diabetic mice." Photomedicine and laser surgery 32.9 (2014): 500-504.

Pernicova, Ida, and Márta Korbonits. "Metformin—mode of action and clinical implications for diabetes and cancer." Nature Reviews Endocrinology 10.3 (2014): 143-156.

Pieralice, Silvia, and Paolo Pozzilli. "Latent autoimmune diabetes in adults: a review on clinical implications and management." Diabetes & Metabolism Journal 42.6 (2018): 451-464.

Poderoso, Juan José, et al. "Nitric oxide inhibits electron transfer and increases superoxide radical production in rat heart mitochondria and submitochondrial particles." Archives of biochemistry and biophysics 328.1 (1996): 85-92.

(56) References Cited

OTHER PUBLICATIONS

Poitout, Vincent, et al. "Morphological and functional characterization of βTC-6 cells—an insulin-secreting cell line derived from transgenic mice." Diabetes 44.3 (1995): 306-313.
Polster, Brian M., and Gary Fiskum. "Mitochondrial mechanisms of neural cell apoptosis." Journal of neurochemistry 90.6 (2004): 1281-1289.
Pozzilli, Paolo, and Silvia Pieralice. "Latent autoimmune diabetes in adults: current status and new horizons." Endocrinology and Metabolism 33.2 (2018): 147-159.
Proks, P., et al. "Sulfonylurea stimulation of insulin secretion. Diabetes. 51: S368-S376." (2002): S368-S376.
Putney, James W. "Pharmacology of store-operated calcium channels." Molecular interventions 10.4 (2010): 209-218.
Radman, Thomas, et al. "Spike timing amplifies the effect of electric fields on neurons: implications for endogenous field effects." Journal of Neuroscience 27.11 (2007): 3030-3036.
Rahman, Faiz Ur, et al. "Critical roles of carbon monoxide and nitric oxide in Ca2+ signaling for insulin secretion in pancreatic islets." Antioxidants & redox signaling 30.4 (2019): 560-576.
Ramadan, James W., et al. "The central role of calcium in the effects of cytokines on beta-cell function: implications for type 1 and type 2 diabetes." Cell calcium 50.6 (2011): 481-490.
Ray, Paul D., Bo-Wen Huang, and Yoshiaki Tsuji. "Reactive oxygen species (ROS) homeostasis and redox regulation in cellular signaling." Cellular signalling 24.5 (2012): 981-990.
Rickels, Michael R., and R. Paul Robertson. "Pancreatic islet transplantation in humans: recent progress and future directions." Endocrine Reviews 40.2 (2019): 631-668.
Rizzo, Mark A., and David W. Piston. "Regulation of β cell glucokinase by S-nitrosylation and association with nitric oxide synthase." The Journal of cell biology 161.2 (2003): 243-248.
Robertson, R. Paul, et al. "Glucose toxicity in β-cells: type 2 diabetes, good radicals gone bad, and the glutathione connection." Diabetes 52.3 (2003): 581-587.
Rodriguez-Calvo, Teresa, et al. "Increased immune cell infiltration of the exocrine pancreas: a possible contribution to the pathogenesis of type 1 diabetes." Diabetes 63.11 (2014): 3880-3890.
Rorsman, Patrik, and Frances M. Ashcroft. "Pancreatic β-cell electrical activity and insulin secretion: of mice and men." Physiological reviews 98.1 (2018): 117-214.
Rorsman, Patrik, and Erik Renström. "Insulin granule dynamics in pancreatic beta cells." Diabetologia 46.8 (2003): 1029-1045.
Rorsman, Patrik, Matthias Braun, and Quan Zhang. "Regulation of calcium in pancreatic α-and β-cells in health and disease." Cell calcium 51.3-4 (2012): 300-308.
Rorsman, Patrik, et al. "Electrophysiology of pancreatic β-cells in intact mouse islets of Langerhans." Progress in biophysics and molecular biology 107.2 (2011): 224-235.
Rosenmund, C., and G. L. Westbrook. "Calcium-induced actin depolymerization reduces NMDA channel activity." Neuron 10.5 (1993): 805-814.
Sabatini, Paul V., Thilo Speckmann, and Francis C. Lynn. "Friend and foe: β-cell Ca2+ signaling and the development of diabetes." Molecular Metabolism 21 (2019): 1-12.
Sachdeva, Mira M., et al. "Pdx1 (MODY4) regulates pancreatic beta cell susceptibility to ER stress." Proceedings of the National Academy of Sciences 106.45 (2009): 19090-19095.
Saisho, Yoshifumi. "β-cell dysfunction: Its critical role in prevention and management of type 2 diabetes." World journal of diabetes 6.1 (2015): 109.
Salehpour, Farzad, et al. "Brain photobiomodulation therapy: a narrative review." Molecular neurobiology 55.8 (2018): 6601-6636.
Samways, Damien SK, and Terrance M. Egan. "Calcium-dependent decrease in the single-channel conductance of TRPV1." Pflügers Archiv—European Journal of Physiology 462.5 (2011): 681-691.
Santulli, Gaetano, et al. "Intracellular calcium release channels: an update." The Journal of physiology 595.10 (2017): 3041-3051.
Sarti, Paolo, et al. "The chemical interplay between nitric oxide and mitochondrial cytochrome c oxidase: reactions, effectors and pathophysiology." International Journal of Cell Biology 2012 (2012).
Schoenbach, Karl H., et al. "Ultrashort electrical pulses open a new gateway into biological cells." Proceedings of the IEEE 92.7 (2004): 1122-1137.
Schoenbach, Karl H., Stephen J. Beebe, and E. Stephen Buescher. "Intracellular effect of ultrashort electrical pulses." Bioelectromagnetics: Journal of the Bioelectromagnetics Society, The Society for Physical Regulation in Biology and Medicine, The European Bioelectromagnetics Association 22.6 (2001): 440-448.
Schoenbach, Karl H., et al. "Ultrashort electrical pulses open a new gateway into biological cells." Proceedings of the IEEE 92.7 (2004): 1122-1137. Schoenbachk, R., n.d. Ultrashort electrical pulses open a new gateway into biological cells. Conference Record of the Twenty-Sixth International Power Modulator Symposium, 2004 and 2004 High-Voltage Workshop.
Seckinger, Kendra M., et al. "Nitric oxide activates β-cell glucokinase by promoting formation of the "glucose-activated" state." Biochemistry 57.34 (2018): 5136-5144.
Shapiro, AM James, Marta Pokrywczynska, and Camillo Ricordi. "Clinical pancreatic islet transplantation." Nature Reviews Endocrinology 13.5 (2017): 268-277.
Sharma, Sulbha K., et al. "Dose response effects of 810 nm laser light on mouse primary cortical neurons." Lasers in surgery and medicine 43.8 (2011): 851-859.
Smedler, Erik, and Per Uhlén. "Frequency decoding of calcium oscillations." Biochimica Et Biophysica Acta (BBA)—General Subjects 1840.3 (2014): 964-969.
Song, Michael Y., Ayako Makino, and Jason X-J. Yuan. "Role of reactive oxygen species and redox in regulating the function of transient receptor potential channels." Antioxidants & redox signaling 15.6 (2011): 1549-1565.
Song, Pei, et al. "Transient microscopy for measuring heat transfer in single cells." arXiv preprint arXiv:1901.00141 (2019). ArVix. org, [online] Available at: <https://arxiv.org/abs/1901.00141> [Accessed Aug. 13, 2020].
Stutzmann, Grace E., and Mark P. Mattson. "Endoplasmic reticulum Ca2+ handling in excitable cells in health and disease." Pharmacological reviews 63.3 (2011): 700-727.
Takayama, Yasunori, et al. "Pain-enhancing mechanism through interaction between TRPV1 and anoctamin 1 in sensory neurons." Proceedings of the National Academy of Sciences 112.16 (2015): 5213-5218.
Tarasov, Andrei I., Elinor J. Griffiths, and Guy A. Rutter. "Regulation of ATP production by mitochondrial Ca2+." Cell calcium 52.1 (2012): 28-35.
Taylor-Clark, Thomas E. "Role of reactive oxygen species and TRP channels in the cough reflex." Cell Calcium 60.3 (2016): 155-162.
Thrivikraman, Greeshma, Sunil Kumar Boda, and Bikramjit Basu. "Unraveling the mechanistic effects of electric field stimulation towards directing stem cell fate and function: A tissue engineering perspective." Biomaterials 150 (2018): 60-86.
Thulé, Peter M., and Guillermo Umpierrez. "Sulfonylureas: a new look at old therapy." Current diabetes reports 14.4 (2014): 473.
Thurmond, Debbie C., et al. "Glucose-stimulated insulin secretion is coupled to the interaction of actin with the t-Snare (target membrane soluble N-ethylmaleimide-sensitive factor attachment protein receptor protein) complex." Molecular endocrinology 17.4 (2003): 732-742.
Tiganis, Tony. "Reactive oxygen species and insulin resistance: the good, the bad and the ugly." Trends in pharmacological sciences 32.2 (2011): 82-89.
Titushkin, Igor A., and Michael R. Cho. "Controlling cellular biomechanics of human mesenchymal stem cells." 2009 Annual International Conference of the IEEE Engineering in Medicine and Biology Society. IEEE, 2009.
Tonelli, Fernanda MP, et al. "Stem cells and calcium signaling." Calcium Signaling. Springer, Dordrecht, 2012. 891-916.
Tong, Jie, et al. "Pulsed electromagnetic fields promote the proliferation and differentiation of osteoblasts by reinforcing intracellular calcium transients." Bioelectromagnetics 38.7 (2017): 541-549.

(56) References Cited

OTHER PUBLICATIONS

Trebak, Mohamed, et al. "Interplay between calcium and reactive oxygen/nitrogen species: an essential paradigm for vascular smooth muscle signaling." Antioxidants & redox signaling 12.5 (2010): 657-674.
Tsai, Shang-Ru, and Michael R. Hamblin. "Biological effects and medical applications of infrared radiation." Journal of Photochemistry and Photobiology B: Biology 170 (2017): 197-207.
Tuomi, Tiinamaija. "Type 1 and type 2 diabetes: what do they have in common?. " Diabetes 54.suppl 2 (2005): S40-S45.
Varadi, Aniko, and Guy A. Rutter. "Dynamic imaging of endoplasmic reticulum Ca2+ concentration in insulin-secreting MIN6 Cells using recombinant targeted cameleons: roles of sarco (endo) plasmic reticulum Ca2+-ATPase (SERCA)-2 and ryanodine receptors." Diabetes 51.suppl 1 (2002): S190-S201.
Vethe, Heidrun, et al. "Probing the missing mature β-cell proteomic landscape in differentiating patient iPSC-derived cells." Scientific reports 7.1 (2017): 1-14.
Wang, Weiwei, Sha Jin, and Kaiming Ye. "Development of islet organoids from H9 human embryonic stem cells in biomimetic 3D scaffolds." Stem cells and development 26.6 (2017): 394-404.
Wang, Yuguang, et al. "Photobiomodulation (blue and green light) encourages osteoblastic-differentiation of human adipose-derived stem cells: role of intracellular calcium and light-gated ion channels." Scientific reports 6 (2016): 33719.
Wang, Yong, et al. "Highly purified versus filtered crude collagenase: comparable human islet isolation outcomes." Cell transplantation 20.11-12 (2011): 1817-1825.
Weir, Gordon C., and Susan Bonner-Weir. "Five stages of evolving beta-cell dysfunction during progression to diabetes." Diabetes 53.suppl 3 (2004): S16-S21.
Whitticar, Nicholas B., and Craig S. Nunemaker. "Reducing Glucokinase Activity to Enhance Insulin Secretion: A Counterintuitive Theory to Preserve Cellular Function and Glucose Homeostasis." Frontiers in Endocrinology 11 (2020): 378.
Wollman, R., and T. Meyer. "Coordinated oscillations in cortical actin and Ca 2+ correlate with cycles of vesicle secretion." Nature cell biology 14.12 (2012): 1261-1269.
Yadav, Anju, and Asheesh Gupta. "Noninvasive red and near-infrared wavelength-induced photobiomodulation: promoting impaired cutaneous wound healing." Photodermatology, photoimmunology & photomedicine 33.1 (2017): 4-13.
Yamada, Masahisa, et al. "Electrical stimulation modulates fate determination of differentiating embryonic stem cells." Stem cells 25.3 (2007): 562-570.
Yan, Xiaodong, et al. "Low-level laser irradiation modulates brain-derived neurotrophic factor mRNA transcription through calcium-dependent activation of the ERK/CREB pathway." Lasers in medical science 32.1 (2017): 169-180.
Yang, Lifen, et al. "TCR-induced Akt serine 473 phosphorylation is regulated by protein kinase C-alpha." Biochemical and biophysical research communications 400.1 (2010): 16-20.
Yao, Jing, Beiying Liu, and Feng Qin. "Heat Activation of Temperature-Gated Ion channels Studied by Fast Temperature Jumps." Biophysical Journal 96.3 (2009): 267a.
Yu, Wei, et al. "Improvement of host response to sepsis by photobiomodulation." Lasers in Surgery and Medicine: The Official Journal of the American Society for Laser Medicine and Surgery 21.3 (1997): 262-268.
Zein, Randa, Wayne Selting, and Michael R. Hamblin. "Review of light parameters and photobiomodulation efficacy: dive into complexity." Journal of biomedical optics 23.12 (2018): 120901.
Zhang, Feng, et al. "Heat activation is intrinsic to the pore domain of TRPV1." Proceedings of the National Academy of Sciences 115.2 (2018): E317-E324.
Zhang, Irina X., Malini Raghavan, and Leslie S. Satin. "The endoplasmic reticulum and calcium homeostasis in pancreatic beta cells." Endocrinology 161.2 (2020): bqz028.

\* cited by examiner

DEVICE AND USES THEREOF FOR TREATING DIABETES

CROSS REFERENCE TO RELATED APPLICATIONS

This application claims the benefit of U.S. Provisional Patent Application Ser. No. 62/900,597, filed Sep. 15, 2019, the disclosures of which are expressly incorporated herein by reference.

FIELD

The present disclosure relates to devices and methods for improving functionality of β-cells and islets.

BACKGROUND

Diabetes mellitus (DM) currently affects approximately 422 million people and costs an estimated $825 billion worldwide. Of those affected by DM, many more suffer from type II in the form of either insulin resistance or β-cell dysfunction than type I. Patients affected by the insulin resistance can manage their condition with proper diet, exercise, and drugs such as metformin; however, some patients suffer from serious β-cell dysfunction which may require similar treatment to those with type I DM. Experimental therapies for type I DM include stem cell therapies to produce insulin secreting cells along with cadaveric islet transplantations, yet these differentiated or isolated cells have been found to have impaired functionality in comparison to their mature in vivo counterparts. Islet transplantation is a procedure used to implant the donated and isolated islets to produce insulin in type I diabetic patients. While the efficacy of the treatment has consistently been improving over the last two decades, several obstacles still remain. For the procedure to be successful, the isolated islets must be quickly transplanted into the patient. If left in culture for several days, the islets lose their viability and functionality and may not be used as a viable treatment. Moreover, cell death after transplantation is commonly high thus limiting the potency of this procedure. Thus, the exploration of methods to manipulate insulin secretion and to improve the viability of isolated islets and β-cell function is beneficial for both forms of diabetes. The compositions and methods disclosed herein address these and other needs.

SUMMARY

In accordance with the purposes of the disclosed materials and methods, as embodied and broadly described herein, the disclosed subject matter, in one aspect, relates to devices and methods of using such devices.

In one aspect, disclosed herein is a bioreactor system comprising:
  a fluid chamber;
  a plurality of cell culture chambers in fluidic communication with the fluid chamber;
  a plurality of cell size sorters coupled to the plurality of cell culture chambers and configured to filter fluid into the plurality of cell culture chambers;
  a sorter inlet in fluidic communication with the fluid chamber;
  a sorted outlet in fluidic communication with the fluid chamber and apart from the sorter inlet;
  at least one electric field generator in electrical communication with at least one of the plurality of cell culture chambers;
  at least one light source in optical communication with the at least one of the plurality of cell culture chambers; and
  a perfusion pump in fluidic communication with the sorter inlet and configured to facilitate the flow of fluid into the sorter inlet and out of the sorted outlet;
  wherein the at least one electric field generator is configured to apply an electric field to at least one of the plurality of cell culture chambers, and
  wherein the at least one light source is configured to generate light in at least one of the plurality of cell culture chambers.

In some embodiments, the at least one electric field generator is configured to apply the electric field, and the at least one light source is configured to generate light simultaneously.

In some embodiments, the at least one electric field generator is configured to apply an electric field, and the at least one light source is configured to generate light sequentially.

In some embodiments, the bioreactor of any preceding aspects further comprises a perfusion manifold, wherein the perfusion manifold is configured to control the inlet and outlet of a culture media to and from the cell culture chambers.

In some embodiments, the bioreactor of any preceding aspects further comprises a culture media reservoir in fluid communication with the perfusion manifold.

In some embodiments, the bioreactor system of any preceding aspects further comprises an oxygenator having a gas inlet and configured to regulate a concentration of oxygen and carbon dioxide inside the culture media.

In some embodiments, the bioreactor system of any preceding aspects further comprises a thermal regulator configured to heat a culture media to a desired temperature level.

In some embodiments, the bioreactor system of any preceding aspects further comprises a computer system, wherein the computer system is configured to control operation of at least the electrical field generator, the light source, and the perfusion pump.

In some embodiments, the bioreactor system of any preceding aspects is configured to sort a group of cells (e.g., β-cells, islets, or stem cells) by size and maintain a favorable culture environment with respect to sterility, oxygenation, nutritional availability, and temperature.

In some embodiments, the bioreactor system of any preceding aspects is configured to facilitate improve functionality of isolated islets or β-cells as an alternative method to donor isolated islet transplantation for induced pluripotent stem cells (iPSCs).

In some embodiments, the bioreactor system of any preceding aspects is configured to facilitate differentiation to the β-cell phenotype to increase the yield of insulin secreting β-cells as an alternative method to donor isolated islet transplantation for induced pluripotent stem cells (iPSCs).

In another aspect, disclosed herein is a method of treating type 1 diabetes, comprising administering to a subject a therapeutically effective amount of isolated islets or β-cells, wherein the isolated islets or the β-cells are generated using the bioreactor system of any preceding aspects.

In yet another aspect, disclosed herein is a method of improving functionality of isolated islets or a group of β-cells comprising pumping the isolated islets or the group of β-cells into a bioreactor system, the bioreactor system comprising:
a fluid chamber;
a plurality of cell culture chambers in fluidic communication with the fluid chamber;
a plurality of cell size sorters coupled to the plurality of cell culture chambers and configured to filter fluid into the plurality of cell culture chambers;
a sorter inlet in fluidic communication with the fluid chamber;
a sorted outlet in fluidic communication with the fluid chamber and apart from the sorter inlet;
at least one electric field generator in electrical communication with at least one of the plurality of cell culture chambers;
at least one light source in optical communication with the at least one of the plurality of cell culture chambers; and
a perfusion pump in fluidic communication with the sorter inlet and configured to facilitate the flow of fluid into the fluid chamber;
wherein the at least one electric field generator is configured to apply an electric field to at least one of the plurality of cell culture chambers, and
wherein the at least one light source is configured to generate light in at least one of the plurality of cell culture chambers; and
applying the electric field to at least one of the plurality of cell culture chambers; and
generating light into at least one of the plurality of cell culture chambers,
wherein the electric field is applied and the light is generated simultaneously or sequentially.

In some aspects, disclosed herein is a method of improving functionality of isolated islets or a group of β-cells, comprising
a) contacting the isolated islets or the group of β-cells with light; and
b) applying an electric field impulse to the isolated islets or the group of β-cells.

In some embodiments, steps a) and b) are applied simultaneously. In some embodiments, steps a) and b) are applied sequentially.

In some embodiments, the isolated islets or the group of β-cells form a cluster with a diameter ranging from about 20 μm to about 1000 μm. In some embodiments, the isolated islets or the group of β-cells form a cluster has a diameter ranging from about 20 μm to about 100 μm.

In some embodiments, the electric field impulse is from about 1.0 to about 5.0 volts per centimeter. In some embodiments, the electric field impulse is from about 3.0 volts per centimeter.

In some embodiments, the light is a near-infrared light. In some embodiments, the near-infrared light has a wavelength from about 600 nm to 1000 nm. In some embodiments, the near-infrared light has a wavelength of about 810 nm.

In some embodiments, the group of β-cells is in contact with the light for about 1 min.

In some embodiments, the light has an intensity of about 150 mW/cm$^2$.

In some embodiments, the electric field impulse is from about 5 min to about 30 min in duration. In some embodiments, the electric field impulse is from about 15 min in duration.

In some embodiments, the group of β-cells are a group of primary β-cells. In some embodiments, the isolated islets are a group of primary islet cells. In some embodiments, the isolated islets or the group of β-cells are differentiated from one or more stem cells. In some embodiments, the one or more stem cells are one or more induced pluripotent stem cells (iPSCs).

In some aspects, disclosed herein is a method of treating type 1 diabetes in a subject in need thereof, comprising
a) contacting isolated islets or a group of β-cells with light;
b) applying an electric field impulse to the isolated islets or the group of β-cells; and
c) administering to the subject a therapeutically effective amount of the isolated islets or the group of β-cells of step a) and/or step b).

In some embodiments, the isolated islets or the group of β-cells are derived from the subject. In some embodiments, the isolated islets or the group of β-cells are not derived from the subject.

The details of one or more embodiments of the invention are set forth in the accompanying drawings and the description below. Other features, objects, and advantages of the invention will be apparent from the description and drawings, and from the claims.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF DRAWINGS

The accompanying figures, which are incorporated in and constitute a part of this specification, illustrate several aspects described below.

FIG. 7A shows comparison between insulin secretion over an hour before and after DCEF exposure. Data represents ELISA absorbance measurements of secreted insulin from 4 independent samples. * denotes $p<0.05$. FIG. 7B shows average intensity of PDX1 expression per cluster between the control and exposed groups. Data represents 181 clusters (control) and 90 clusters (exposed) from 10 independent samples each. *** denotes $p<0.001$. Representative image of anti-PDX1 labeling in βTC6 cells (FIG. 7C) before and (FIG. 7D) after exposure to DCEF.

FIG. 9A shows calcium spiking frequency following PBM exposure with and without (−Ca) extracellular calcium. FIG. 9B shows calcium spiking frequency following PBM in response to treatment with verapamil (+Ver, 100 μM) and capsazepine (+Capz, 10 μM). Data represent mean±SEM of >130, 60, and 60 cells from 10, 9, and 10 independent experiments for −Ca, +Ver, and +Capz, respectively. *$p<0.05$, $p<0.01$, and *$p<0.001$ Immunostained images for TRPV1 channels (FIG. 9C) and L-type VGCCs (FIG. 9D), respectively, with nuclei counterstaining (blue).

FIG. 10A shows calcium spiking frequency after exposure to PBM following treatment with dantrolene (50 μM) to probe the role of the Ryanodine receptor-mediated calcium release. FIG. 10B shows calcium spiking frequency after exposure with 2-APB (20 μM) to probe the role of the IP3 receptor-mediated calcium release. Data represent mean±SEM of >40 active cells from 8 independent experiments. *$p<0.05$, $p<0.01$, and *$p<0.001$.

FIG. 12A shows MitoSOX intensity between PBM and PBM+AA groups following exposure, indicating the diminished levels of superoxide in response to AA treatment (2.5 mM). FIG. 12B shows change in calcium spiking frequency following PBM exposure and after treatment with AA. Data represent mean±SEM of >110 active cells from 8 independent experiments. *$p<0.05$, $p<0.01$, and *$p<0.001$.

FIG. 23A shows schematic illustration of DCEF chamber with a sample mounted to demonstrate the fluid chamber and the flow of an electrical current. FIG. 23B shows image of chamber used for DCEF exposure with electrical terminal sides labeled with corresponding color tape. The design minimizes any unwanted byproducts to reach the sample and is suitable for short exposures (e.g., <1 hr).

DETAILED DESCRIPTION

Figures 1A, 1B:
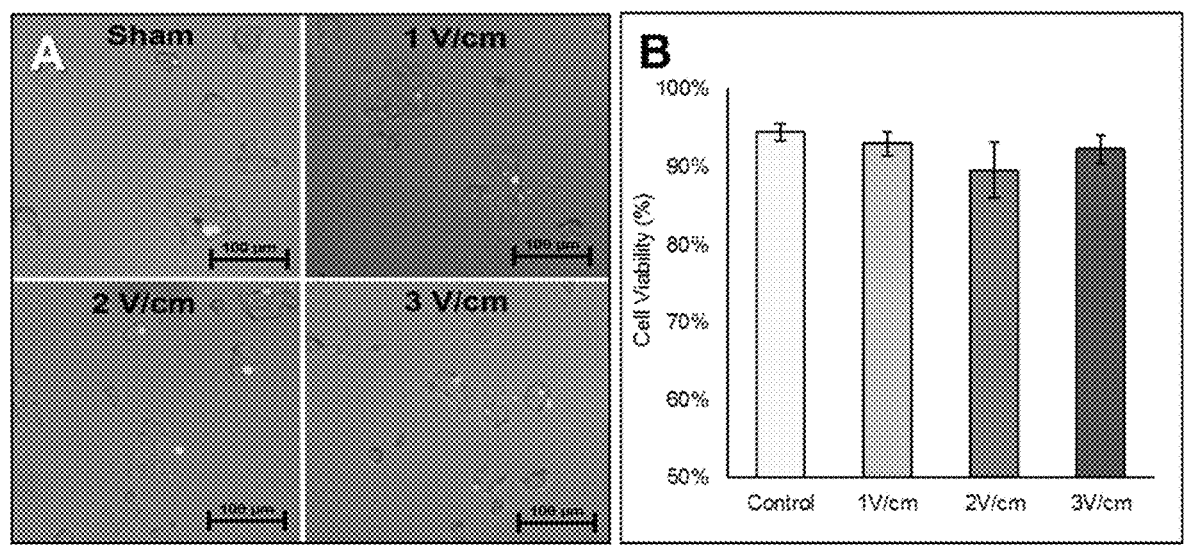
FIG. 1A shows representative images for cell viability in response to EF. Blue stained for all nuclei while green stained for nuclei of dead cells.
FIG. 1B shows quantification of changes in cell viability by various EF strengths. Data represent mean±SEM from 3 independent experiments.

The materials, compounds, compositions, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Terms used throughout this application are to be construed with ordinary and typical meaning to those of ordinary skill in the art. However, Applicant desires that the following terms be given the particular definition as defined below.

Terminology

As used in the specification and claims, the singular form "a," "an," and "the" include plural references unless the context clearly dictates otherwise. For example, the term "an agonist" includes a plurality of agonist, including mixtures thereof.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir, and the like. Administration includes self-administration and the administration by another.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "islet of Langerhans" or "islet" refers to a group of specialized cells in the pancreas that make and secrete hormones. An islet generally contains one or more of the following cell types: (1) alpha cells that make glucagon, which raises the level of glucose (sugar) in the blood; (2) β-cells that make insulin; (3) delta cells that make somatostatin which inhibits the release of numerous other hormones in the body; (4) pancreatic peptide producing PP cells; (5) D1 cells, which secrete vasoactive intestinal peptide; or (6) endothelial cells (ECs) which secrete secretin, motilin, and substance P.

As used herein, the term "β-cell" refers to any cell which can produce and secrete insulin in a similar amount to that produced and secreted by a beta cell of the islets of Langerhans in the human pancreas.

As used herein, the term "islet cell" refers to any one of the cells found in an islet. The islet cells used in the disclosed devices and methods are preferably a combination insulin-producing β-cells with other islet cell types.

As used herein, the term "differentiates or differentiated" defines a stem cell that takes on a more committed ("differentiated") position within the lineage of a cell (e.g., a β-cell).

A "stem cell" as used herein is an undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. Stem cells are pluripotential, and given the appropriate signals from their environment, they can differentiate into any tissue or any cell type (e.g., β-cell) in the body.

As used herein, the term "inducible pluripotent stem cell (iPSC)" or "induced pluripotent stem cell" is understood to mean a pluripotent stem cell artificially derived from a non-pluripotent cell, typically an adult somatic cell, by inducing forced expression of specific genes. By having the potential to become iPSCs, it is meant that the differentiated somatic cells can be induced to become, i.e. reprogrammed to become, iPSCs. In other words, the somatic cell can be induced to re-differentiate so as to establish cells having the morphological characteristics, growth ability and pluripotency of pluripotent cells. iPSCs express one or more key pluripotency markers by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42.

As used herein, the term "diabetes" refers to the set of diseases and conditions known collectively as "diabetes mellitus," including "type 1 diabetes," "type 2 diabetes," "gestational diabetes" (during pregnancy), "Mutant INS-gene-induced Diabetes of Youth" (MIDY), and other states that cause hyperglycaemia. The term is used for disorders in which the pancreas produces and/or secretes insufficient amounts of active/properly-folded insulin, and/or in which the cells of the body fail to respond appropriately to insulin (e.g., "insulin resistance") thus preventing cells from absorbing glucose. As a result of the different, untreated forms of diabetes, glucose builds up in the blood.

"Type 1 diabetes," also called "insulin-dependent diabetes mellitus" ("IDDM") and "juvenile-onset diabetes," is caused by β-cell destruction and/or the inability of the pancreas to produce active insulin, usually leading to absolute insulin deficiency.

"Insulin" refers to a peptide created by β-cells of the pancreatic islets. It regulates the metabolism of carbohydrates, fats, and proteins. In some embodiments, the insulin disclosed herein refers to the peptide comprising the sequence of UniProt ID #P01308-1.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, "stimulate", as well as the correlated term "stimulation", refer to the action of generating, promoting, forming, regulating, activating, enhancing or accelerating a biological phenomenon.

"Increase" can refer to any change that results in a higher level of gene expression, protein expression, amount of a symptom, disease, composition, condition, or activity. A substance is also understood to increase the level of the gene, the protein, the composition, or the amount of the condition when the level of the gene, the protein, the composition, or the amount of the condition is more/higher relative to the output of the level of the gene, the protein, the composition, or the amount of the condition without the substance. Also, for example, an increase can be a change in the symptoms of a disorder such that the symptoms are less than previously observed. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

"Decrease" can refer to any change that results in a lower level of gene expression, protein expression, amount of a symptom, disease, composition, condition, or activity. A substance is also understood to decrease the level of the gene, the protein, the composition, or the amount of the condition when the level of the gene, the protein, the composition, or the amount of the condition is less/lower relative to the output of the level of the gene, the protein, the composition, or the amount of the condition without the substance. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

The term "subject" refers to a human in need of treatment for any purpose, and more preferably a human in need of treatment to treat a disease or disorder, such as ischemia. The term "subject" can also refer to non-human animals, such as dogs, cats, horses, cows, pigs, sheep and non-human primates, among others.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, New Jersey). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder (e.g., type 1 diabetes), or a symptom of a disease or disorder. The terms "treating" and "treatment" can also refer to reduction in severity and/or frequency of symptoms, elimination of symptoms and/or underlying cause, and improvement or remediation of damage.

"Therapeutically effective amount" or "therapeutically effective dose" of a composition (e.g. β-cells) refers to an amount that is effective to achieve a desired therapeutic result. In some embodiments, a desired therapeutic result is the decrease of glucose levels in blood. In some embodiments, a desired therapeutic result is the increase of insulin levels. In some embodiment, a desired therapeutic result is the treatment of diabetes. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Reference will now be made in detail to specific aspects of the disclosed materials, compounds, compositions, articles, and methods, examples of which are illustrated in the accompanying Examples and Figures.

Bioreactor System

The underlying mechanisms that cause β-cell dysfunction are still being investigated, but current models generally involve chronic elevated levels of oxidative stress. This chronic elevation of reactive oxygen species (ROS) can result in a decrease in insulin regulating transcription factors, in particular pancreatic and duodenal homeobox 1 (PDX1). The PDX1 transcription factor regulates the production of insulin along with assortment of other roles in β-cell functionality and survival. It is potent enough that transfection with PDX1 in hepatic cells and stem cells yielded insulin expression. A small molecule named Indolactam V (IL-V) has been reported to increase PDX1 levels in stem cells committed towards a pancreatic lineage, and has been used to improve stem cell differentiation protocols. IL-V can exert this effect by activating protein kinase C (PKC) with downstream effectors elevating the PDX1 expression.

Direct current electric fields (DCEFs) have demonstrated the capacity to affect a multitude of cellular processes leading to changes at the cellular and tissue scale. In particular interest, DCEFs have been shown to elevate the intracellular calcium levels in a variety of cell types. While these exogenous electric fields (EFs) have been applied artificially, natural endogenous EFs have been observed during organogenesis and embryogenesis and are believed to act as a signaling mechanism in the differentiation and organization of various tissues. While exogenous DCEFs have been applied to a variety of cell types, only a limited knowledge can be found on how these applied DCEFs affect the functionality of insulin producing cells. Investigation on the response of β-cell to DCEFs identifies potential therapeutic effects that proves advantageous in mending dysfunctional insulin producing cells. In the present disclosure, mouse derived insulinoma (βTC6) cells were selected since these cells have already been widely used as a β-cell model and have shown to be glucose responsive. Exposure of non-invasive electric field for a short period of time (e.g., 15 min) upregulates the PDX1 expression and increase the insulin secretion.

Both electric field and light therapies have been used to induce therapeutic effects. If optimized each stimulus appears to induce beneficial effects although the coupling mechanisms mediating such effects are likely different. It represents a clinical and scientific breakthrough by combining the two different stimulatory modalities and synergistically increase the viability of islets and improve the functionality of insulin secretion.

By using a chamber that is capable of controlling the application of both of these modalities, the isolated islets can be pre-conditioned and improved prior to transplantation into the Type I diabetic patient. Both of these stimuli have been proven to affect the islets through the regulation of intracellular calcium dynamics Change in the intracellular calcium dynamics alters the physiological responses and modulate the viability and functionality of the islets.

While systems have been developed for both of these types of stimuli, this design allows to explore and implement the synergistic effects. By improving the viability of islets using these physical stimulations simultaneously or sequentially, the overall efficiency of islet transplantations can be improved. This can dramatically increase the potency of precious donor islets and improve the outcome for the patient. In addition, these combined stimulations are capable of preserving the functionality of the islets, and therefore provide a needed technique to preserve the islet for longer culture duration. Clinically, it allows the clinicians more time and flexibility with the logistics of islet transplantation including selection of proper islet recipients.

Islet transplantation is limited by the availability of donor islets. One way to overcome this limitation has been to differentiate stem cells to insulin-secreting cell types or islet cells and transplant the differentiated β-cells. While stem cells have been shown to differentiate to the β-cell phenotype, a number of unresolved issues prevent transplantation of differentiated β-cells to the Type I diabetic patient. Among the most challenging issues is the lack of complete differentiation and also the lack of insulin secretion. The device disclosed herein can be used to facilitate stem cell differentiation to the β-cell phenotype and therefore offers an alternative to the donor islet transplantation.

The current disclosure shows a bioreactor system comprising:
a fluid chamber;
a plurality of cell culture chambers in fluidic communication with the fluid chamber;
a plurality of cell size sorters coupled to the plurality of cell culture chambers and configured to filter fluid into the plurality of cell culture chambers;
a sorter inlet in fluidic communication with the fluid chamber;
a sorted outlet in fluidic communication with the fluid chamber and apart from the sorter inlet;
at least one electric field generator in electrical communication with at least one of the plurality of cell culture chambers;
at least one light source in optical communication with the at least one of the plurality of cell culture chambers; and
a perfusion pump in fluidic communication with the sorter inlet and configured to facilitate the flow of fluid into the sorter inlet and out of the sorted outlet;
wherein the at least one electric field generator is configured to apply an electric field to at least one of the plurality of cell culture chambers, and
wherein the at least one light source is configured to generate light in at least one of the plurality of cell culture chambers.

Figure 24:
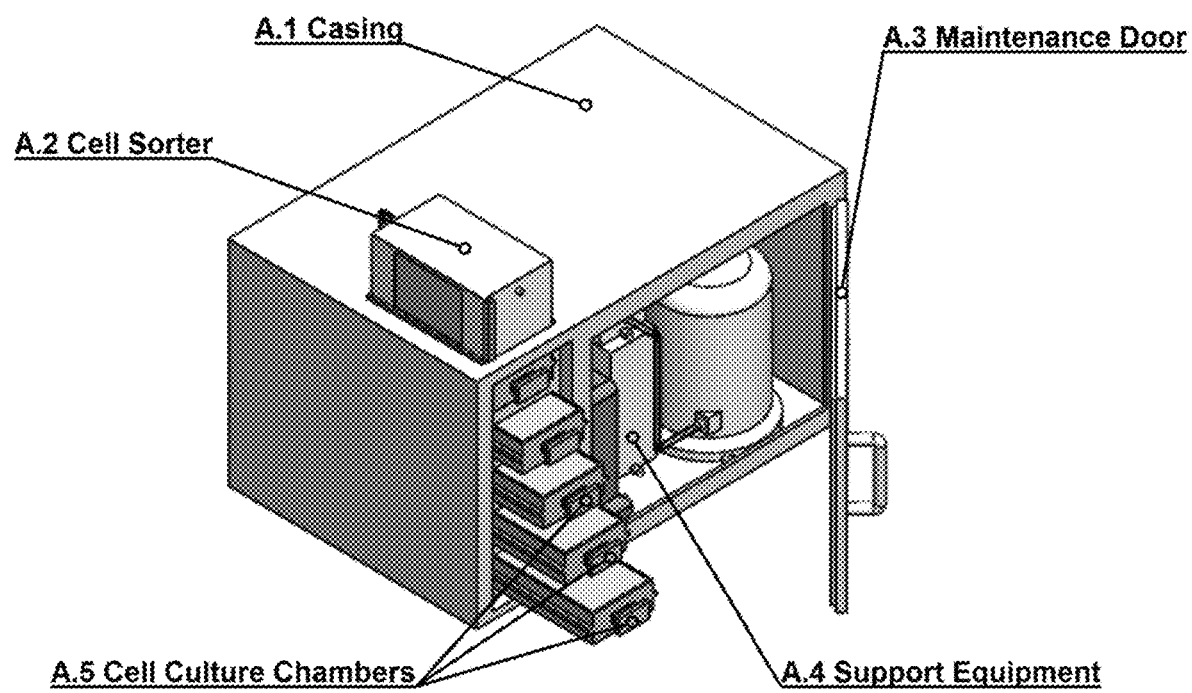
FIG. 24 shows external overview of the device with the maintenance door open.

In some aspects, disclosed herein is a method of improving functionality of isolated islets or a group of β-cells comprising pumping the isolated islets or the group of β-cells into a bioreactor system, the bioreactor system comprising:
a fluid chamber;
a plurality of cell culture chambers in fluidic communication with the fluid chamber;
a plurality of cell size sorters coupled to the plurality of cell culture chambers and configured to filter fluid into the plurality of cell culture chambers;
a sorter inlet in fluidic communication with the fluid chamber;
a sorted outlet in fluidic communication with the fluid chamber and apart from the sorter inlet;
at least one electric field generator in electrical communication with at least one of the plurality of cell culture chambers;
at least one light source in optical communication with the at least one of the plurality of cell culture chambers; and
a perfusion pump in fluidic communication with the sorter inlet and configured to facilitate the flow of fluid into the fluid chamber;
wherein the at least one electric field generator is configured to apply an electric field to at least one of the plurality of cell culture chambers, and
wherein the at least one light source is configured to generate light in at least one of the plurality of cell culture chambers; and
applying the electric field to at least one of the plurality of cell culture chambers; and
generating light into at least one of the plurality of cell culture chambers,
wherein the electric field is applied and the light is generated simultaneously The overall geometry and external design are displayed in FIG. 24. The casing (A.1) can be composed of either metal or plastic with a sole role of protecting the internal components from the local environment. The cell sorter (A.2) can be placed at the top of the casing with tubing placed through the casing and leading to the back plate and eventually into each of the cell culture chambers. At the front (A.3) a maintenance door has been placed that can be latched shut. Support equipment (A.4) is placed inside and fixed to the bottom of the casing. This equipment is responsible for maintaining the cell culture environment. Multiple cell culture chambers (A.5) are stacked and interfaced with the internal components to support and stimulate the cell cultures.

Figure 25:
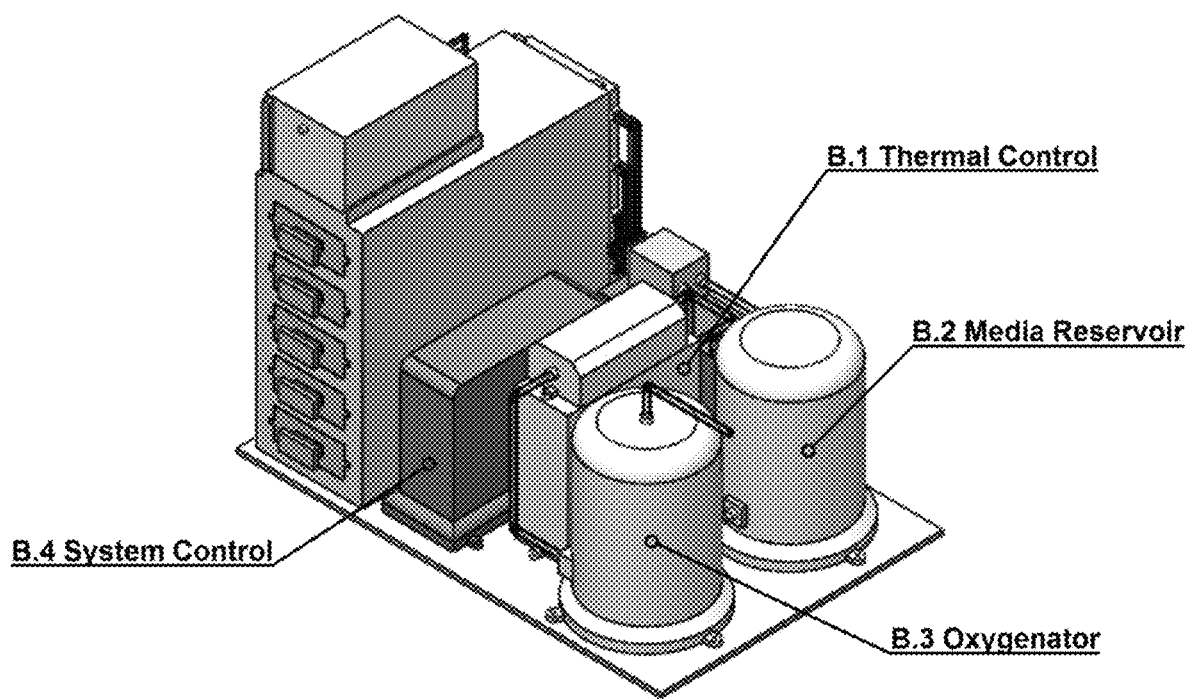
FIG. 25 shows front right view of the device without casing wall displaying major support components.
Figure 26:
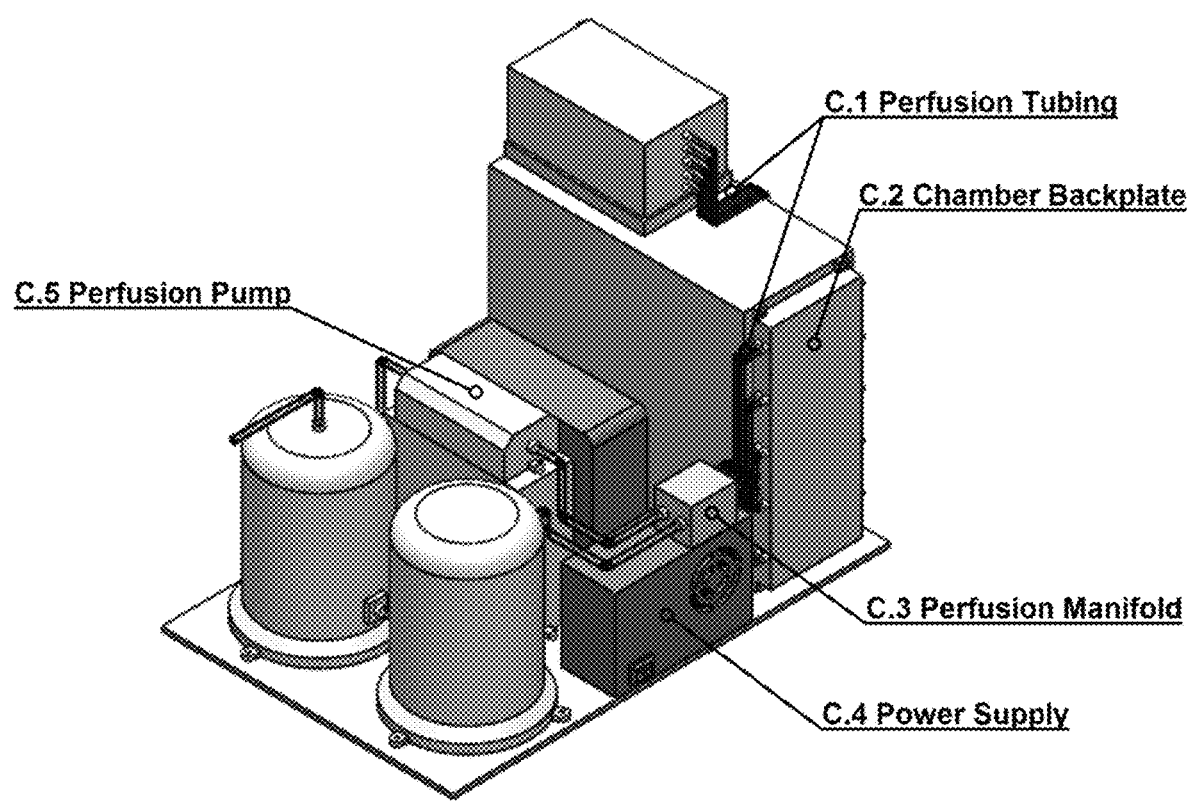
FIG. 26 shows back right view of device displaying support components not easily seen in FIG. 25.

Several stock or custom pieces of equipment maintain the cell culture housed within the external casing. Media flows from the cell culture chambers to the back plate (C.2 of FIG. 26) and into the perfusion manifold (C.3 of FIG. 26) via plastic tubing (C.1 of FIG. 26). The back plate interfaces with the culture chambers for media perfusion along with electrical and lighting control. The perfusion manifold controls the inlet and outlet of media to and from the culture chambers. From the manifold, the media flows into a large removable chamber (B.2 of FIG. 25) acting as a reservoir for the culture media. The media then flows from the reservoir into the oxygenator (B.3 of FIG. 25) which has a gas inlet for regulating the concentration of oxygen and carbon dioxide inside the media. Conditioned media is then led into the perfusion pump (C.5 of FIG. 26) along with being further conditioned by a thermal regulator (B.1 of FIG. 25). The thermal regulator heats the perfused media to a desired level between room temperature and 37° C. (98° F.) using electrical heating. This media is led back into the perfusion manifold and sent to each individual culture chamber. All of these components are controlled by a computer system (B.4 of FIG. 25) that interact with an external computer and controlled by the device's user.

Figure 27:
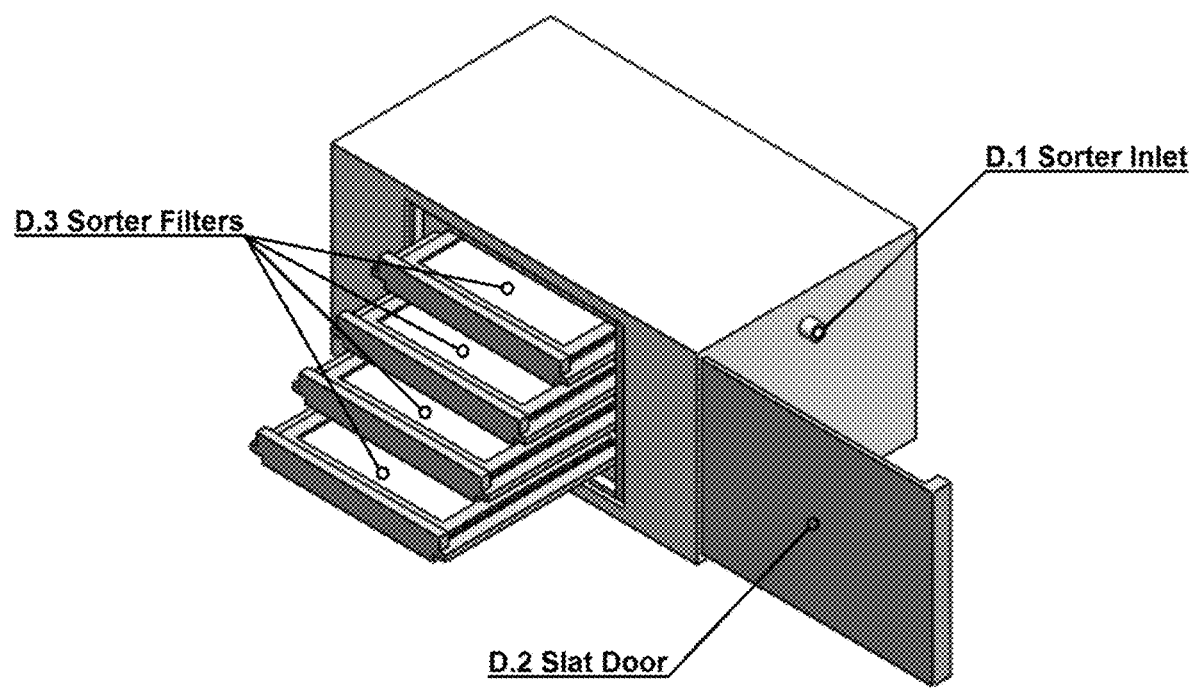
FIG. 27 shows cell size sorter with door open and size filters pulled out and on display.
Figure 28:
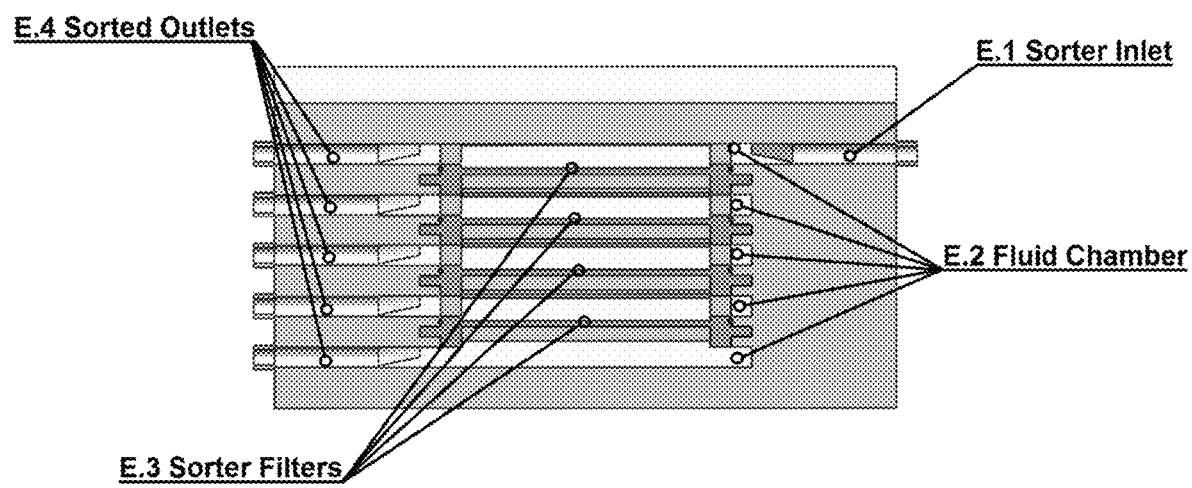
FIG. 28 shows cross-section of cell sorter displaying multiple fluid channels with interspaced filters.

The overall chamber for the sorter is be constructed out of a stiff yet biocompatible polymer, while the filters are manufactured separately with particular size cutoffs. The islet sorter starts with the inlet (D.1 of FIG. 27) for where islet containing media may be inserted with a proper pressure potential. From here the cells continue into the fluid chambers where a downwards and horizontal pressure causes smaller islets to pass through the filters (D.3 of FIG. 27) while islets larger than the cutoff remain in the chamber and flow towards their respective outlet. To allow user control over which size islets go to which chamber, filters will be modular and allow for different size exclusions. The cutoff of the filter can be, for example, less than about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 1 cm. To protect the channels and filter slats, a closing slat door (D.2 of FIG. 27) is be included in the sorting device. A cross sectional view of the islet sorter demonstrates more clearly the paths the islets may take. From the inlet (E.1 of FIG. 28) to the chambers (E.2 of FIG. 28) and through their size specific filters (E.3 of FIG. 28) until each islet size group passes to their respective outlets (E.4 of FIG. 28) and towards the individual culture chambers.

Figure 29:
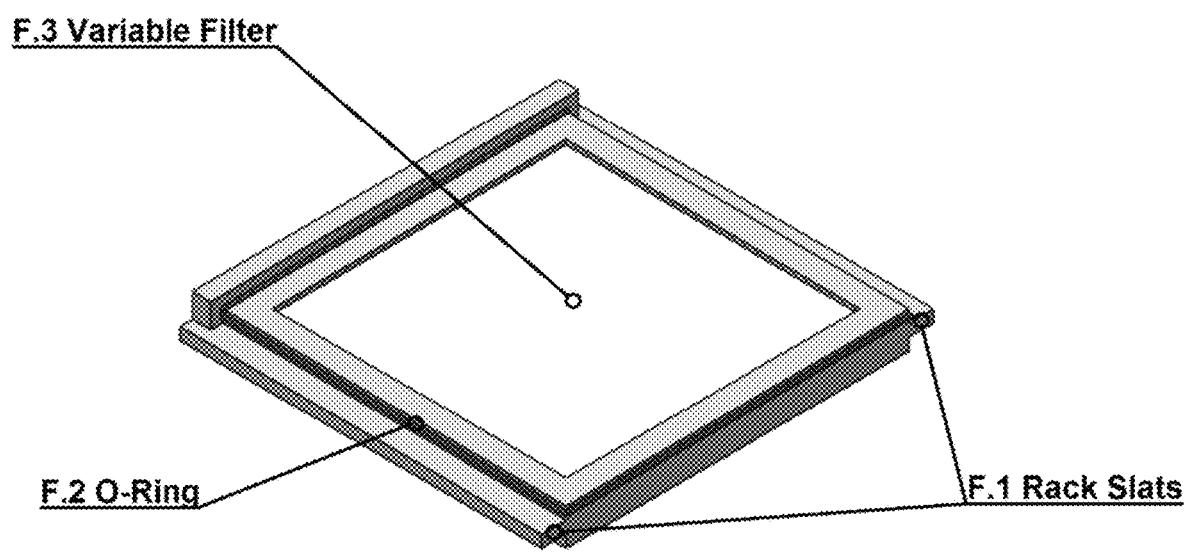
FIG. 29 shows individual filter with guide rails and O-ring on display.

Each filter casing is likely be made out of a similar material to the chamber. The casing contains slats (F.1 of FIG. 29) on the sides so as to easily interface with the sorter while keeping the filter in place. The center of the filter contains a homogenous pore size filter (F.3 of FIG. 29) to preclude islets of a certain size from passing through. To maintain a proper seal, a sealing part (F.2 of FIG. 29) such as an O-ring, is placed around the casing to prevent any media leaking into another flow chamber or into the surrounding casing.

Figure 30:
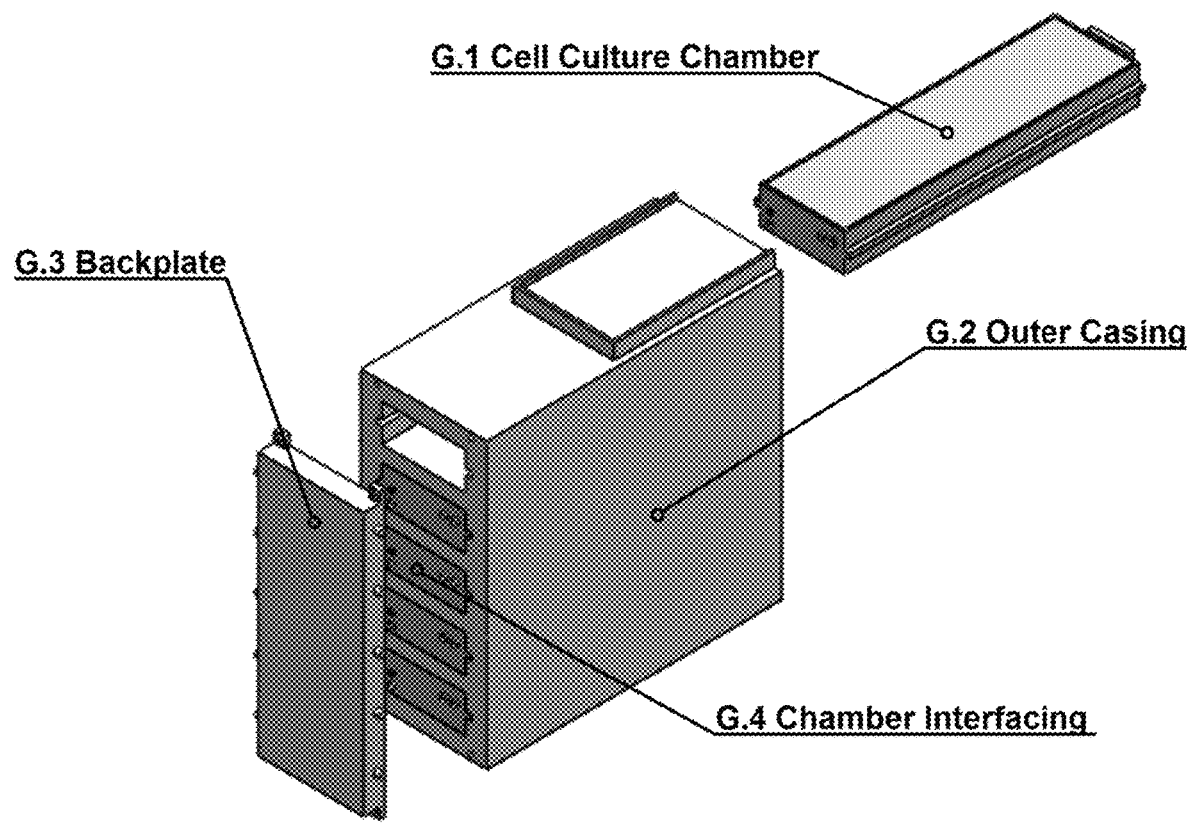
FIG. 30 shows interfacing between cell culture chambers, the chamber casing, and the back plate.

The culture chambers (G.1 of FIG. 30) are be placed next to each other inside of a chamber casing (G.2 of FIG. 30). Each chamber includes guiderails on the side that match with the casing. At the end of the casing a back plate is placed (G.3 of FIG. 30) that interfaces (G.4 of FIG. 30) with the individual cell culture chambers. This includes piping to allow for media perfusion along with a valve to allow cell cultures to enter from the sorting device. Wiring inside the back plate connects the electrical components (LED Array and Electrical Loop) to the central controller for application of electric field and light therapeutics.

Figure 31:
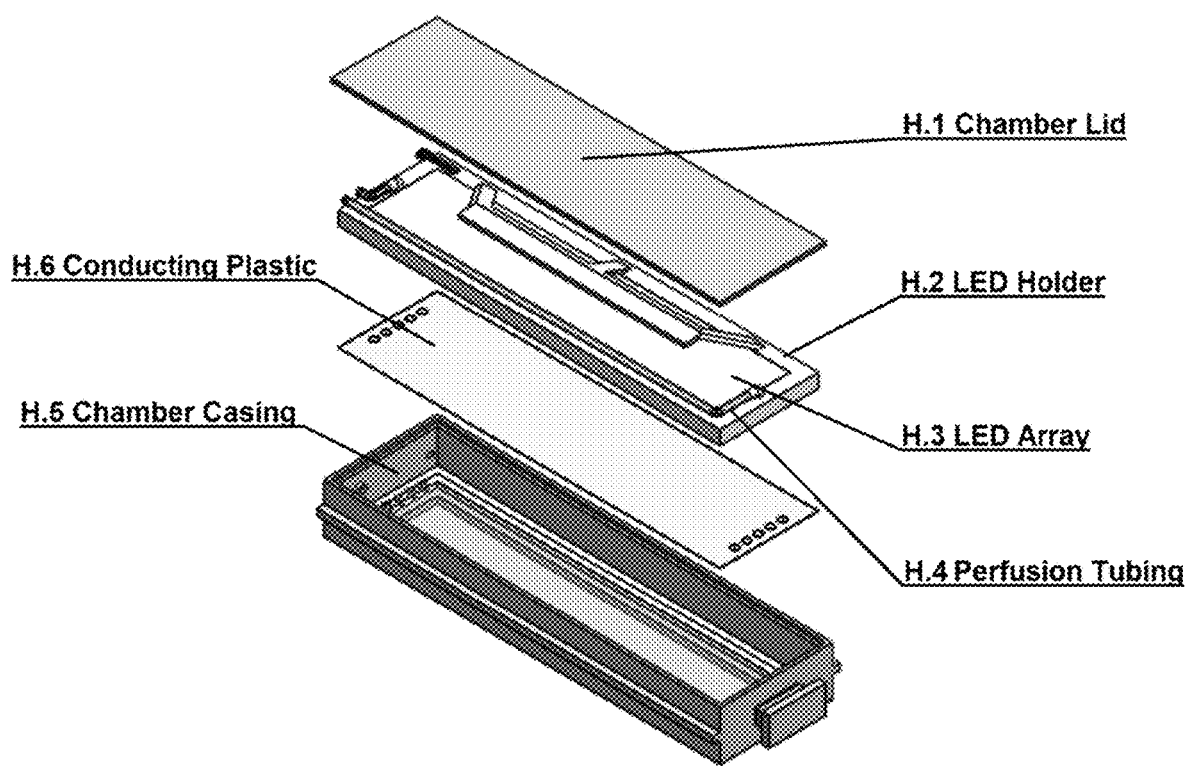
FIG. 31 shows exploded view of cell culture chamber with major components displayed.

FIG. 31 shows how the individual components the cell culture chamber fit together. On top the chamber lid (H.1 of FIG. 31) is placed to preserve the internal environment with a sealing material around it to prevent any contamination. Below is an LED holder (H.2 of FIG. 31) that can be removable and house the LED Array (H.3 of FIG. 31) along with perfusion tubing (H.4 of FIG. 31) that interfaces with the back plate (G.3 of FIG. 30). The material (e.g., conducting plastic sheet or glass) below the LED holder uniformly conducts current through the culture media. Finally, all of these components can be fitted within the external chamber casing (H.5 of FIG. 31).

Figures 12A, 12B:
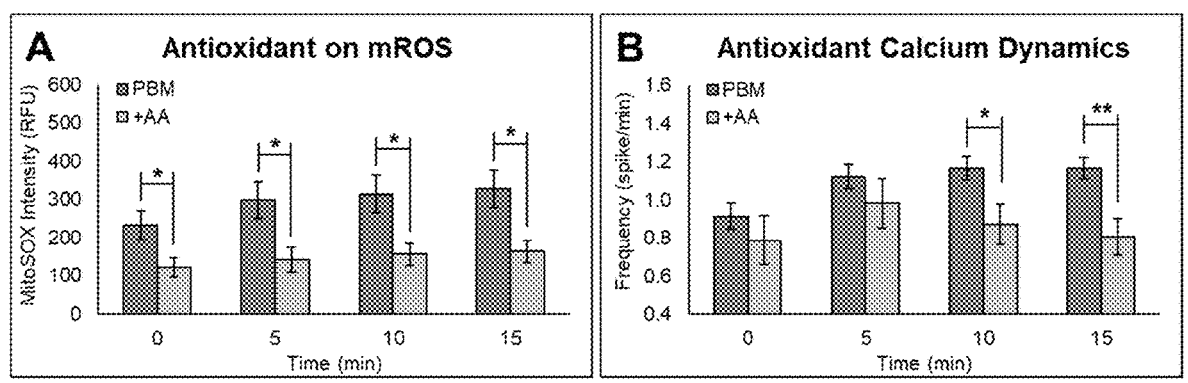
FIGS. 12A-12B show effects of ascorbic acid (AA).
Figure 32:
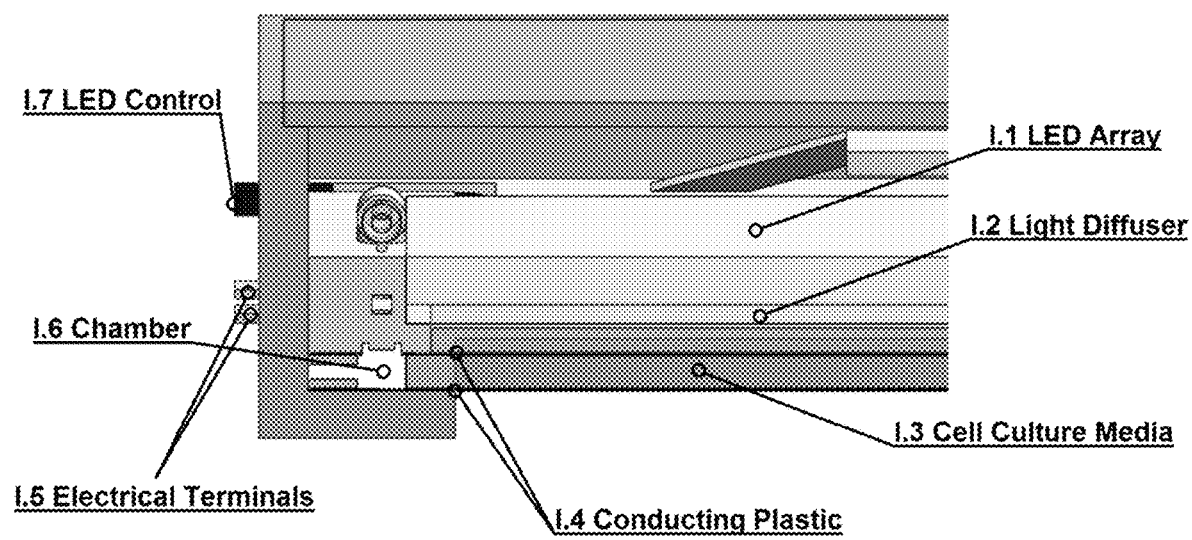
FIG. 32 shows cross-section of cell culture chamber demonstrating the fitting between components.

FIGS. 12A-12B show a zoomed in cross section of the internal assembly of the cell culture chamber. At the top, the LED Array (I.1 of FIG. 32) rests on top of a light diffuser (I.2 of FIG. 32). The light that the LED emits can be in several frequencies within the visible light spectrum (400-700 nm) all the way into the near infrared spectrum (700-1400 nm). The diffuser is made out of a polymer as long as the optical properties allow for high transmittance and diffusion of the light. A conducting sheet (I.4 of FIG. 32) is below the diffusor in contact with the cell culture media (I.3 of FIG. 32). The conducting sheets are in contact with the media both above and below the culture area. In contact with the sheets at the periphery, electric loops of conducting metal lead to terminals (I.5 of FIG. 32) leading out of the culture chamber.

These interact with the back plate and be managed by the control system while supplied by the power supply. An insulating material (I.6 of FIG. 32) is placed between the two conducting sheets and defining the geometry of the culture area. Additionally, this part contains holes that connect to the LED holder allowing for media perfusion. Finally, a channel allows LED controller wiring (I.7 of FIG. 32) to lead into the back plate of the culture casing.

Figure 33:
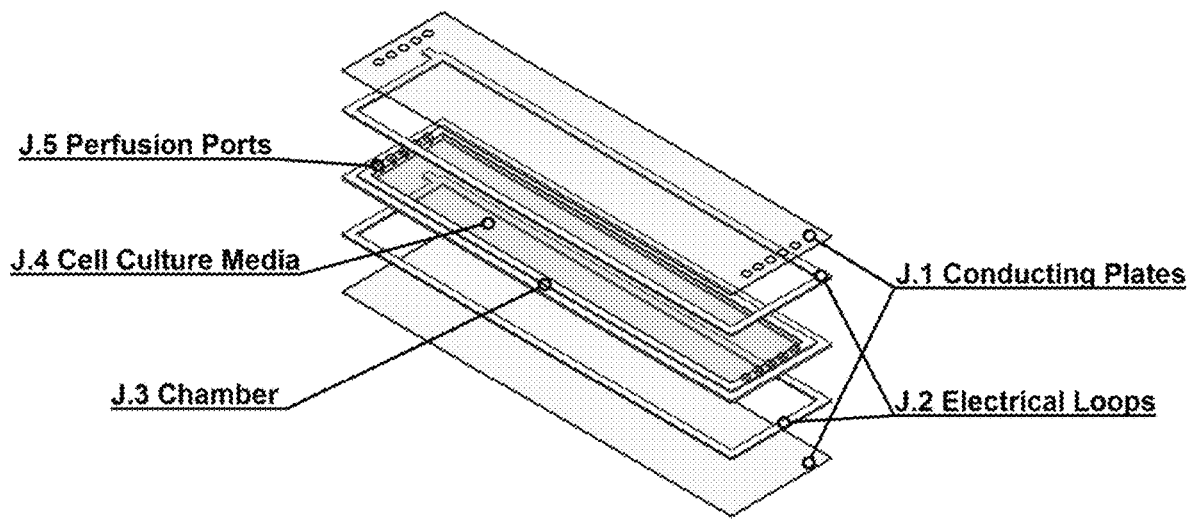
FIG. 33 shows exploded view of internal chamber showing stimulatory components next to the cell culture.

An exploded view of the internal chamber is shown in FIG. 33. Two conducting plates (J.1 of FIG. 33) are placed above and below the culture area to allow for the generation of an electric field. The top sheet contains holes (J.5 of FIG. 33) allowing for diffusion connections. In close contact to the conducting sheets are the electrical loops (J.2 of FIG. 33) that carry current from the system to the conducting sheets. The distance between the conducting sheets are made such to maintain a voltage below 1.2 Volts while allowing an applied electric field from about 10 to about 1000 V/m. This should prevent electrolysis of the media and the development of gases with a resulting shift in pH. The chamber (J.3 of FIG. 33) is made large enough to accommodate a reasonable number of islets while maintaining a low distance between the sheets. Additionally, it insulates well enough to prevent current from traveling directly from loop to loop. In the center of the chamber cells are attached to the bottom sheet while media flows at a rate that allows for adequate nutrient and oxygen perfusion but slow enough to prevent significant shear stress on the cells.

The disclosed bioreactor system can be a complete cell culture system capable of applying non-invasive electrical and light stimulation simultaneously with its primary application to increase the viability of isolated islets and to improve their functionality prior to transplantation. The same device can also be applied to stem cells and other relevant cell types to facilitate the differentiation to insulin-secreting cells. Optimization of delivery of the physical stimuli affects the electrical active cell types such as brain cells and heart muscle cells to regulate their functionality.

In some implementations, the bioreactor system is capable of applying both electric field and light exposure simultaneously or sequentially in order to improve the viability and functionality of donor isolated pancreatic islets so as to improve the efficiency of islet transplantation procedures and allow for further investigation into the synergistic effects of these modalities.

It should be understood here that the above noted bioreactor system applied to human iPSCs to facilitate differentiation to the β-cell phenotype to increase the yield of insulin secreting β-cells can be an alternative method to donor isolated islet transplantation.

In some aspects, disclosed herein is a bimodal stimulation system that is additionally capable of sorting islets by size and maintaining a favorable culture environment with respect to sterility, oxygenation, nutritional availability, and temperature.

Accordingly, disclosed herein is a method of treating type 1 diabetes, comprising administering to a subject a therapeutically effective amount of β-cells, wherein the β-cells are generated using the bioreactor of any preceding aspects.

Methods of Treatment

In some aspects, disclosed herein is a method of treating type 1 diabetes in a subject in need thereof, comprising
  a) contacting isolated islets or a group of β-cells with light;
  b) applying an electric field impulse to the isolated islets or the group of β-cells; and
  c) administering to the subject a therapeutically effective amount of the isolated islets or the group of β-cells of step a) and/or step b).

In some embodiments, steps a) and b) are applied simultaneously. In some embodiments, steps a) and b) are applied sequentially.

The methods disclosed herein can improve functionality of isolated islets and/or β-cells, wherein the improvement in functionality comprises, for example, an increase in insulin production and/or secretion of β-cells, increase in viability (e.g., increase in live cell numbers) of isolated islets and/or β-cells, and/or increase in proliferation of isolated islets and/or β-cells. In one example, the increase or the improvement refers to a higher level relative to the level without an application of the method disclosed herein.

According, in some aspect, disclosed herein is a method of improving functionality of isolated islets and/or a group of β-cells or functionality of isolated islets and/or a group of β-cells, comprising
  a) contacting the isolated islets and/or the β-cells with light; and
  b) applying an electric field impulse to the isolated islets and/or the group of β-cells In some aspects, disclosed herein is a method of improving viability of isolated islets and/or a group of β-cells or functionality of isolated islets and/or a group of β-cells, comprising
  a) contacting the isolated islets and/or the β-cells with light; and
  b) applying an electric field impulse to the isolated islets and/or the group of β-cells.

It should be understood that an isolated islet can comprise one islet cell or more than one islet cell, wherein an islet cell refers to any type of cells found in an islet, as discussed above. It should also be understood that β-cells or isolated islets (or islet cells) tend to form clusters. Such a cluster preferably comprises β-cells as the predominant cell type, and may optionally include one or more other islet cell types. The cluster preferably has a morphology such that the diffusional barrier for any cell within the cluster. In some embodiments, the isolated islets or the group of β-cells form a cluster having a diameter ranging from about 5 µm to about 1000 µm. Accordingly, the isolated islets or the group of β-cells form a cluster having a diameter of about, for example, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 1 cm. In some embodiments, the isolated islets or the group of β-cells form a cluster having a diameter ranging from about 20 µm to about 100 µm. In some embodiments, the isolated islets or the group of β-cells form a cluster having a diameter of about 50 µm.

As noted above, a plurality of cell size sorters are used to select β-cell clusters having diameters below a cutoff value. It is understood herein that any sorter well known in the art can be used herein for selecting islet cells and β-cell clusters having diameters below a cutoff value.

In some embodiments, the electric field impulse is from about 1.0 to about 10.0 volts per centimeter. In some embodiments, the electric field impulse is from about 2.0 to about 5.0 volts per centimeter. Accordingly, the electric field impulse applied to isolated islets or a group of β-cells can be, for example, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 7.0, about 8.0, about 9.0, or about 10.0 volts per centimeter. In some embodiments, the electric field impulse is about 3.0 volts per centimeter.

In some embodiments, the electric field impulse is from about 5 min to about 60 min in duration. In some embodiments, the electric field impulse is from about 5 min to about 30 min in duration. Accordingly, the electric field impulse is about 1 min, about 2 min, about 3 min, about 4 min, about 5 min, about 6 min, about 7 min, about 8 min, about 9 min, about 10 min, about 11 min, about 12 min, about 13 min, about 14 min, about 15 min, about 16 min, about 17 min, about 18 min, about 19 min, about 20 min, about 21 min, about 22 min, about 23 min, about 24 min, about 25 min, about 26 min, about 27 min, about 28 min, about 29 min, about 30 min, about 31 min, about 32 min, about 33 min, about 34 min, about 35 min, about 36 min, about 40 min, about 45 min, about 50 min, or about 60 min in duration. In some embodiments, the electric field impulse is from about 15 min in duration. In some embodiments, the duration of electric field impulse is one continuous period of electric field impulse or the sum of total of multiple continuous periods of electric field impulse.

In some embodiments, the light comprises a wavelength of from about 50 nm to about 1000 nm, such as from about 50 nm to about 400 nm, from about 400 nm to about 500 nm, from about 500 nm to about 600 nm, from about 600 nm to about 750 nm, from about 650 nm to about 800 nm, from about 600 nm to about 1000 nm, from about 700 nm to about 900 nm, from about 750 nm to about 950 nm, from about 350 nm to about 750 nm, from about 750 nm to about 850 nm, from about 800 nm to about 850 nm, from about 800 nm to about 900 nm, or from about 800 nm to about 1000 nm. In some embodiment, the light is a near-infrared light. In some embodiments, the light has a wavelength about 600 nm, about 620 nm, about 640 nm, about 660 nm, about 680 nm, about 700 nm, about 710 nm, about 720 nm, about 730 nm, about 740 nm, about 750 nm, about 760 nm, about 770 nm, about 780 nm, about 790 nm, about 800 nm, about 810 nm, about 820 nm, about 830 nm, about 840 nm, about 850 nm, about 860 nm, about 870 nm, about 880 nm, about 890 nm, about 900 nm, about 920 nm, about 940 nm, about 960 nm, about 980 nm, or about 1000 nm.

In some embodiments, the light is applied over from about 5 seconds to about 60 min in duration. In some embodiment, the light is applied over from about 30 seconds to about 5 min. In some embodiments, the light is applied over from about 30 seconds to about 2 min. In some embodiments, the light is applied over from about 1 min to about 5 min. In some embodiments, the light is applied over from about 5 min to about 72 hours. In some embodiments, the light is applied over from about 5 min to about 30 min in duration. Accordingly, the light is about 30 seconds, about 1 min, about 1.5 min, about 2 min, about 2.5 min, about 3 min, about 3.5 min, about 4 min, about 4.5 min, about 5 min, about 5.5 min, about 6 min, about 7 min, about 8 min, about 9 min, about 10 min, about 11 min, about 12 min, about 13 min, about 14 min, about 15 min, about 16 min, about 17 min, about 18 min, about 19 min, about 20 min, about 21 min, about 22 min, about 23 min, about 24 min, about 25 min, about 26 min, about 27 min, about 28 min, about 29 min, about 30 min, about 31 min, about 32 min, about 33 min, about 34 min, about 35 min, about 36 min, about 40 min, about 45 min, about 50 min, or about 60 min in duration. In some embodiments, the light is applied over from about 15 min in duration. In some embodiments, the light is about 1 hour, about 2 hours, about 3 hours, about 4 hours, about 5 hours, about 6 hours, about 7 hours, about 8 hours, about 9 hours, about 10 hours, about 12 hours, about 13 hours, about 14 hours, about 15 hours, about 16 hours, about 17 hours, about 18 hours, about 19 hours, about 20 hours, about 22 hours, about 24 hours, about 28 hours, about 32 hours, about 36 hours, about 40 hours, about 44 hours, about 48 hours, about 54 hours, about 60 hours, about 66 hours, or about 72 hours in duration. In some embodiments, the duration of light is one continuous period or the sum of total of multiple continuous periods of light.

In some embodiments, the light has an intensity from about 50 mW/cm$^2$ to about 500 mW/cm$^2$ (e.g., about 50 mW/cm$^2$, about 60 mW/cm$^2$, about 70 mW/cm$^2$, about 80 mW/cm$^2$, about 90 mW/cm$^2$, about 100 mW/cm$^2$, about 110 mW/cm$^2$, about 120 mW/cm$^2$, about 130 mW/cm$^2$, about 140 mW/cm$^2$, about 150 mW/cm$^2$, about 160 mW/cm$^2$, about 170 mW/cm$^2$, about 180 mW/cm$^2$, about 190 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, or about 500 mW/cm$^2$).

In some embodiments, the light results in a fluence from about 1 J/cm$^2$ to about 50 J/cm$^2$ (for example, from about 1 J/cm$^2$ to about 20 J/cm$^2$, from about 5 J/cm$^2$ to about 20 J/cm$^2$, from about 5 J/cm$^2$ to about 10 J/cm$^2$, from about 7 J/cm$^2$ to about 12 J/cm$^2$, from about 9 J/cm$^2$ to about 15 J/cm$^2$, from about 9 J/cm$^2$ to about 12 J/cm$^2$, from about 10 J/cm$^2$ to about 20 J/cm$^2$). In some embodiments, the light results in a fluence of about 1 J/cm$^2$, about 1.5 J/cm$^2$, about 2 J/cm$^2$, about 2.5 J/cm$^2$, about 3 J/cm$^2$, about 3.5 J/cm$^2$, about 4 J/cm$^2$, about 4.5 J/cm$^2$, about 5 J/cm$^2$, about 5.5 J/cm$^2$, about 6 J/cm$^2$, about 6.5 J/cm$^2$, about 7 J/cm$^2$, about 7.5 J/cm$^2$, about 8 J/cm$^2$, about 8.1 J/cm$^2$, about 8.2 J/cm$^2$, about 8.3 J/cm$^2$, about 8.4 J/cm$^2$, about 8.5 J/cm$^2$, about 8.6 J/cm$^2$, about 8.7 J/cm$^2$, about 8.8 J/cm$^2$, about 8.9 J/cm$^2$, about 9 J/cm$^2$, about 9.1 J/cm$^2$, about 9.2 J/cm$^2$, about 9.3 J/cm$^2$, about 9.4 J/cm$^2$, about 9.5 J/cm$^2$, about 9.6 J/cm$^2$, about 9.7 J/cm$^2$, about 9.8 J/cm$^2$, about 9.9 J/cm$^2$, about 10 J/cm$^2$, about 10.1 J/cm$^2$, about 10.2 J/cm$^2$, about 10.3 J/cm$^2$, about 10.4 J/cm$^2$, about 10.5 J/cm$^2$, about 10.6 J/cm$^2$, about 10.7 J/cm$^2$, about 10.8 J/cm$^2$, about 10.9 J/cm$^2$, about 11 J/cm$^2$, about 11.5 J/cm$^2$, about 12 J/cm$^2$, about 12.5 J/cm$^2$, about 13 J/cm$^2$, about 14 J/cm$^2$, about 15 J/cm$^2$, about 16 J/cm$^2$, about 17 J/cm$^2$, about 18 J/cm$^2$, about 19 J/cm$^2$, or about 20 J/cm$^2$.

In some embodiments, the isolated islets or the group of β-cells are derived from the subject. In some embodiments, the isolated islets or the group of β-cells are differentiated from one or more stem cells derived from the subject. In some embodiments, the one or more stem cells are one or more induced pluripotent stem cells (iPSCs) derived from the subject. In some embodiments, the isolated islets or the β-cells are engineered cells derived from the subject.

In some embodiments, the isolated islets or the group of β-cells are not derived from the subject. In some embodiments, the isolated islets or the group of β-cells are differentiated from one or more stem cells derived from another subject. In some embodiments, the isolated islets or the one or more stem cells are one or more induced pluripotent stem cells (iPSCs) derived from another subject. In some embodiments, the isolated islets or the β-cells are engineered cells derived from another subject. In some embodiments, the isolated islets or the β-cells are cell lines. In some embodiments, the isolated islets or the β-cells are engineered cells.

It is understood and herein contemplated that type 1 diabetes can arise from dysfunction of β-cells. As the timing of type 1 diabetes can often not be predicted, it should be understood the disclosed methods of treating, preventing, reducing, and/or inhibiting type 1 diabetes can be used following the dysfunction of β-cells, prior to or following the onset of type 1 diabetes, to treat, prevent, inhibit, and/or reduce type 1 diabetes. In some embodiments, the disclosed methods can be performed any time prior to the onset of type 1 diabetes including prior to the dysfunction of β-cells occurs. In one aspect, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3, or 2 years, 12, 11, 10, 9, 8, 7, 6, 5, 4, 3, or 2 months, 30, 29, 28, 27, 26, 25, 24, 23, 22, 21, 20, 19, 18, 17, 16, 15, 14, 13, 12, 11, 10, 9, 8, 7, 6, 5, 4, or 3 days, 60, 48, 36, 30, 24, 18, 15, 12, 10, 9, 8, 7, 6, 5, 4, 3, or 2 hours, 60, 45, 30, 15, 10, 9, 8, 7, 6, 5, 4, 3, 2, or 1 minute prior to dysfunction of β-cells; concurrently with dysfunction of β-cells; or 1, 2, 3, 4, 5, 6, 7, 8, 9, 10, 15, 20, 25, 30, 35, 40, 45, 50, 55, 60, 75, 90, 105, 120 or more minutes, 3, 4, 5, 6, 7, 8, 9, 10, 11, 12, 15, 18, 24, 30, 36, 48, 60 or more hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days, 4, 5, 6, 7, 8, 9, 10, 11, 12 or more months, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more years after dysfunction of endothelial cell barrier, but prior to onset of any symptoms of type 1 diabetes. In one aspect, the disclosed methods can be employed 1, 2, 3, 4, 5, 6, 7, 8, 9, 10, 15, 20, 25, 30, 35, 40, 45, 50, 55, 60, 75, 90, 105, 120 or more minutes, 3, 4, 5, 6, 7, 8, 9, 10, 11, 12, 15, 18, 24, 30, 36, 48, 60 or more hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more years after onset of type 1 diabetes.

Dosing frequency for the isolated islets or the β-cells, includes, but is not limited to, at least about once every five years, once every four years, once every three years, or once every two years. In some embodiments, the dosing frequency for the isolated islets or the β-cells, includes, but is not limited to, at least about once every twelve months, once every eleven months, once every ten months, once every nine months, once every eight months, once every seven months, once every six months, once every five months, once every four months, once every three months, once every two months, once every month, once every three weeks, once every two weeks, or once a week. In some embodiments, the dosing frequency for the β-cells, includes, but is not limited to, at last, about once every 14 days, once every 13 days, once every 12 days, once every 11 days, once every 10 days, once every 9 days, once every 8 days, once every 7 days, once every 6 days, once every 5 days, once every 4 days, once every 3 days, once every 2 days, or daily. In some embodiments, the interval between each administration is less than about a year, such as less than about any of 12, 10, 8, 6, 4, or 2 months. In some embodiments, the interval between each administration is less than about a month, such as less than about any of 30, 28, 26, 24, 22, 20, 18, 16, 14, 12, 10, 8, 6, 4, or 2 days. In some embodiments, the interval between each administration is less than about a week, such as less than about any of 6, 5, 4, 3, 2, or 1 day. In some embodiments, the dosing frequency for the therapeutic agent includes, but is not limited to, at least once a day, twice a day, three times a day, or four times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is less than about 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is constant. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between a course of administration is no more than about a week.

In some aspects, the above noted β-cells are formulated with a pharmaceutically acceptable carrier.

In some aspects, the method of any preceding aspects further comprises administering to the subject an anti-diabetes agent.

In some aspects, disclosed herein is a method of stimulating insulin production from a group of β-cells, improving insulin secretion, improving functionality of islets or β-cells comprising a) contacting the group of islets or β-cells with light; and
b) applying an electric field impulse to the group of islets or β-cells.

SPECIFIC EMBODIMENTS

In some aspects, disclosed herein is a bioreactor system comprising:
  a fluid chamber;
  a plurality of cell culture chambers in fluidic communication with the fluid chamber;
    a plurality of cell size sorters coupled to the plurality of cell culture chambers and configured to filter fluid into the plurality of cell culture chambers;
    a sorter inlet in fluidic communication with the fluid chamber;
    a sorted outlet in fluidic communication with the fluid chamber and apart from the sorter inlet;
    at least one electric field generator in electrical communication with at least one of the plurality of cell culture chambers;
    at least one light source in optical communication with the at least one of the plurality of cell culture chambers; and
    a perfusion pump in fluidic communication with the sorter inlet and configured to facilitate the flow of fluid into the sorter inlet and out of the sorted outlet;
  wherein the at least one electric field generator is configured to apply an electric field to at least one of the plurality of cell culture chambers, and
  wherein the at least one light source is configured to generate light in at least one of the plurality of cell culture chambers.

In some embodiments, the at least one electric field generator is configured to apply the electric field, and the at least one light source is configured to generate light simultaneously.

In some embodiments, the at least one electric field generator is configured to apply an electric field, and the at least one light source is configured to generate light sequentially.

In some embodiments, the bioreactor system disclosed herein further comprises a perfusion manifold, wherein the perfusion manifold is configured to control the inlet and outlet of a culture media to and from the cell culture chambers.

In some embodiments, the bioreactor system disclosed herein further comprises a culture media reservoir in fluid communication with the perfusion manifold.

In some embodiments, the bioreactor system disclosed herein further comprises an oxygenator having a gas inlet and configured to regulate a concentration of oxygen and carbon dioxide inside the culture media.

In some embodiments, the bioreactor system disclosed herein further comprises a thermal regulator configured to heat a culture media to a desired temperature level.

In some embodiments, the bioreactor system disclosed herein further comprises a computer system, wherein the computer system is configured to control operation of at least the electrical field generator, the light source, and the perfusion pump.

In some embodiments, the bioreactor is configured to sort a group of β-cells by size and maintain a favorable culture environment with respect to sterility, oxygenation, nutritional availability, and temperature.

In some embodiments, the bioreactor system disclosed herein is configured to facilitate differentiation to the β-cell phenotype to increase the yield of insulin secreting β-cells as an alternative method to donor isolated islet transplantation for induced pluripotent stem cells (iPSCs).

In some aspects, disclosed herein is a method of treating type 1 diabetes, comprising administering to a subject a therapeutically effective amount of isolated islets or β-cells, wherein the isolated islets or the β-cells are generated using the bioreactor system of disclosed herein.

In some embodiments, disclosed herein is a method of improving functionality (e.g., increasing insulin production, viability, and/or proliferation) of isolated islets or a group of β-cells comprising
pumping the isolated islets or the group of β-cells into a bioreactor system, the bioreactor system comprising:
  a fluid chamber;
  a plurality of cell culture chambers in fluidic communication with the fluid chamber;
  a plurality of cell size sorters coupled to the plurality of cell culture chambers and configured to filter fluid into the plurality of cell culture chambers;
  a sorter inlet in fluidic communication with the fluid chamber;
  a sorted outlet in fluidic communication with the fluid chamber and apart from the sorter inlet;
  at least one electric field generator in electrical communication with at least one of the plurality of cell culture chambers;
  at least one light source in optical communication with the at least one of the plurality of cell culture chambers; and
  a perfusion pump in fluidic communication with the sorter inlet and configured to facilitate the flow of fluid into the fluid chamber;
  wherein the at least one electric field generator is configured to apply an electric field to at least one of the plurality of cell culture chambers, and
  wherein the at least one light source is configured to generate light in at least one of the plurality of cell culture chambers; and
  applying the electric field to at least one of the plurality of cell culture chambers; and generating light into at least one of the plurality of cell culture chambers,
  wherein the electric field is applied and the light is generated simultaneously.

In some aspects, disclosed herein is a method of improving functionality (e.g., increasing insulin production, viability, and/or proliferation) of isolated islets or a group of β-cells, comprising
  a) contacting the isolated islets or the group of β-cells with light; and
  b) applying an electric field impulse to the isolated islets or the group of β-cells.

In some embodiments, steps a) and b) are applied simultaneously. In some embodiments, steps a) and b) are applied sequentially.

In some embodiments, the isolated islets or the group of β-cells form a cluster with a diameter ranging from about 20 µm to about 1000 µm.

In some embodiments, the isolated islets or the group of β-cells form a cluster with a diameter ranging from about 20 µm to about 100 µm.

In some embodiments, the electric field impulse is from about 1.0 to about 5.0 volts per centimeter. In some embodiments, the electric field impulse is from about 3.0 volts per centimeter.

In some embodiments, the electric field impulse is from about 5 min to 30 min in duration. In some embodiments, the electric field impulse is from about 15 min in duration.

In some embodiments, the light is a near-infrared light. In some embodiments, the near-infrared light has a wavelength from about 600 nm to 1000 nm. In some embodiments, the near-infrared light has a wavelength about 810 nm.

In some embodiments, the isolated islets or the group of β-cells is in contact with the light for about 1 min.

In some embodiments, the light has an intensity of about 150 mW/cm$^2$.

In some embodiments, the group of β-cells are a group of primary β-cells. In some embodiments, the isolated islets are primary islet cells. In some embodiments, the isolated islets or the group of β-cells are differentiated from one or more stem cells. In some embodiments, the one or more stem cells are one or more induced pluripotent stem cells (iPSCs).

In some aspects, disclosed herein is a method of treating type 1 diabetes in a subject in need thereof, comprising
  a) contacting the isolated islets or a group of β-cells with light;
  b) applying an electric field impulse to the isolated islets or the group of β-cells; and
  c) administering to the subject a therapeutically effective amount of the isolated islets or the group of β-cells of step a) and/or step b).

In some embodiments, steps a) and b) are applied simultaneously. In some embodiments, The method of claim 18, steps a) and b) are applied sequentially.

In some embodiments, the isolated islets or the group of β-cells form a cluster with a diameter ranging from about 20 µm to about 1000 µm.

In some embodiments, the isolated islets or the group of β-cells form a cluster with a diameter ranging from about 20 µm to about 100 µm.

In some embodiments, the electric field impulse is from about 1.0 to about 5.0 volts per centimeter. In some embodiments, the electric field impulse is from about 3.0 volts per centimeter.

In some embodiments, the electric field impulse is from about 5 min to 30 min in duration. In some embodiments, the electric field impulse is from about 15 min in duration.

In some embodiments, the isolated islets or the group of β-cells are derived from the subject. In some embodiments, the isolated islets or the group of β-cells are not derived from the subject.

In some embodiments, the light is a near-infrared light. In some embodiments, the near-infrared light has a wavelength from about 600 nm to 1000 nm. In some embodiments, the near-infrared light has a wavelength about 810 nm.

In some embodiments, the isolated islets or the group of β-cells is in contact with the light for about 1 min.

In some embodiments, the light has an intensity of about 150 mW/cm$^2$.

In some embodiments, the group of β-cells are a group of primary β-cells. In some embodiments, the isolated islets are primary islet cells. In some embodiments, the isolated islets or the group of β-cells are differentiated from one or more stem cells. In some embodiments, the one or more stem cells are one or more induced pluripotent stem cells (iPSCs).

EXAMPLES

Those skilled in the art will recognize or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Example 1 Altered B-Cell Calcium Dynamics Via Electric Field Exposure

Introduction

In insulin producing β-cells, their calcium dynamics play a critical role in the signaling mechanisms affecting their functionality. It affects the secretion and production of insulin, the expression of transcription factors, and the cell's viability. In healthy β-cells, insulin secretion is normally initiated by an elevation in glucose uptake, resulting in an increase of glucokinase activity, ultimately leading to an increase in glucose catabolism. The resulting rise in ATP closes ATP sensitive potassium channels leading to membrane depolarization. The resulting depolarizing events activate voltage gated calcium channels (VGCCs) leading to an increase in intracellular calcium. This rise in cytosolic calcium directly activates insulin granule exocytosis leading to insulin secretion. Unfortunately, this process along with insulin production can be hindered by several disease states or by chronic cellular stress resulting in β-cell dysfunction.

The most common disease state affecting β-cell function is type II Diabetes Mellitus (DM). In type II diabetes, β-cells will eventually become dysfunctional due to glucotoxicity brought about by a chronic hyperglycemic environment. Hyperglycemia can usually be managed with diet, exercise, and drugs such as metformin, leading to some recovery of β-cell function. However, in some cases chronic hyperglycemia can lead to irreversible glucotoxicity, and thus a more direct intervention is required. Drugs such as Sulfonylurea's and GLP-1 agonists exert direct effects on β-cells to improve insulin secretion and manage type II DM. While these drugs act via differing mechanisms, both influence the calcium dynamics and thus insulin release dynamics within these cells.

Exogenous electric fields (EFs) have demonstrated the capacity to affect a multitude of cellular processes. Its therapeutic potential has been well demonstrated in wound healing by effecting cell migration, proliferation, and protein expression in various cell types. Some of these responses have been attributed to the ability of various modes of EFs to modify intracellular calcium dynamics. For instance, there has been success in controlling intracellular calcium dynamics and thus their biological effects via pulsed electric fields. While pulsed fields have some advantages over continuous DCEFs, the naturally occurring DC endogenous fields are commonly found at strengths between 1 to 5 V/cm. In addition, using a constant DCEFs limits the effects of electrical stimulation to the cell membrane surface, as pulsed fields are able to effect intracellular dynamics. Of particular interest here, DCEFs have also been shown to alter intracellular calcium dynamics in several cell types. While these cell types have been investigated, very little knowledge exists about the effects of EFs on the calcium dynamics of β-cells. By elucidating the effects of electric field stimulation (EFS) on the calcium dynamics of a β-cell model, new modes of therapies can be adapted for in vivo stimulation and islet transplantation for type II and type I diabetes, respectively.

Materials and Methods

Device design. The electric field exposure chamber was designed to minimize temperature rise (<0.1° C.) and unwanted byproducts, as described in detail elsewhere. Briefly, a direct current from an amplifier (BOP100, KEPCO, Flushing, NY) was applied to the chamber using two platinum electrodes. The cross-sectional area of the chamber has been designed with specific dimensions (16 mm×0.8 mm) to minimize the input electrical current (<4 mA) and yet produce an electric field strength of up to 3±0.1 V/cm. This range of electric field strengths was intentionally chosen to represent the physiological electric field of ~2 v/cm. A feedback control mechanism was applied to maintain a constant current during the 15 min exposure. The electric field was calculated using Ohm's law, $J=\sigma E$, when J is the current density and $\sigma$ is the conductivity of the buffer (1 S/m at room temperature) and monitored using an oscilloscope (Model 2205, Tektronix, Beaverton, OR). It should be noted that the device was designed for a short time EF exposure (<1 hr) to living cells and to be mounted onto a microscope stage for real-time observation. All experiments were performed at room temperature.

Figures 23A, 23B:
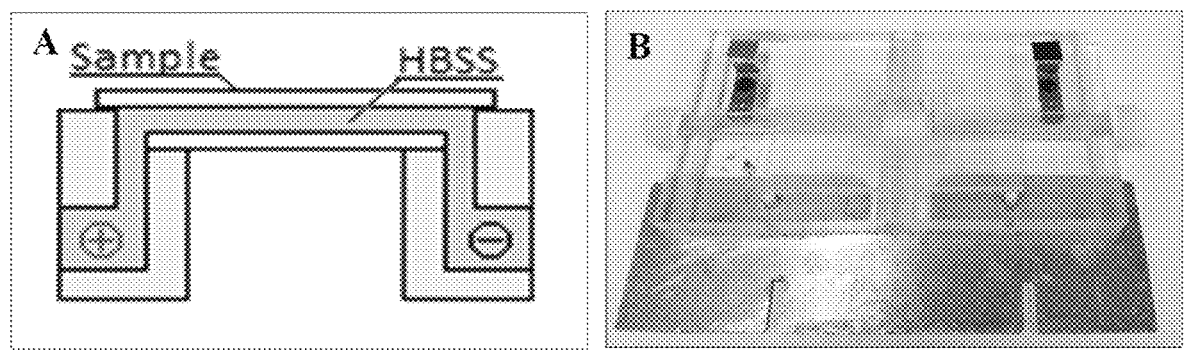
FIGS. 23A and 23B show chamber design for DCEF exposure.

The electric field chamber consists of an observation window through which subcellular processes can be visualized (FIG. 23A and FIG. 23B). The bottom of the window is covered with a bottom glass coverslip to efficient conduct away any Ohmic heating. The top glass coverslip that contained seeded cells was placed and its edges were sealed with vacuum grease to prevent any leaking. This observation chamber is filled with different buffer solutions depending on the experiment (e.g., calcium free HBSS). The cross-sectional area of the chamber can be designed with specific dimensions (16 mm×0.8 mm) to minimize the input electrical current (4 mA) and produce an electric field strength of 3±0.1 V/cm. The electric field was calculated using Ohm's law, $J=\delta E$, when J is the current density and $\delta$ is the conductivity of the buffer (1 S/m at room temperature). It should be noted that the device was designed for a short time EF exposure (<1 hr) to living cells and to be mounted onto a microscope stage. Further details of the chamber have been provided elsewhere.

Electric Field Stimulation Parameters. The field's intensity was set to 3 V/cm and for a 15 mM exposure for all experiments. A DC power supply (100 W, KEPCO) was calibrated using a precision 5 Ohm resistor. A feedback control mechanism was applied to maintain a constant 4 mA current during the 15 min exposure.

Calcium labeling and depletion. Samples were washed with HBSS (Sigma) and incubated with 0.8 µM Fluo-8 (Abcam) for 30 minutes. NucBlue solution (Thermo) was added for 15 min in accordance to the manufacturer's recommended concentration to stain the nuclei. Cells were washed again and mounted onto the chamber. Changes in the Fluo-8 fluorescent intensity were monitored and recorded. Fluorescent images were acquired for 2 min at 5 s intervals with a 250 ms exposure time before and after the DCEF was applied. Image analysis was performed using the Nikon Elements image processor by identifying a ROI selection on selected nuclei with mean intensity of Fluo-8 over time. The calcium channel blocking agent verapamil (100 µM)51 was utilized along with calcium-depleted HBSS that was supplemented with a magnesium sulfate solution (0.8 mM).

Radial Distance Analysis. ROIs for clusters were generated based on the boundary of the calcium images, while each cell's ROI was generated using its nucleus staining. The Cartesian coordinates of each cell's ROI centroid were recorded alongside the coordinates of the cluster's center. Radial distance was determined for each cell and compared to the fold change in Fluo-8 intensity over the baseline readings.

Insulin Secretion Quantification. All samples were seeded at the density of $4 \times 10^4$ cells/cm2 and grown for 3 to 4 days. The samples were washed, transferred to a new petri dish, and then incubated at 37° C. for 30 min in 0.55 mM glucose phosphate buffered saline (G-PBS) to remove any external insulin. The samples were then washed and incubated for an additional hour in 1 mL of G-PBS at 37° C. Following the incubation, the buffer was removed and frozen for analysis (pre-EF), and the sample was mounted on the chamber and exposed for 15 minutes at 3 V/cm. The sample was then placed in a new petri dish and incubated in 1 mL of G-PBS for another hour. After which, the sample's buffer (post-EF) was collected also stored in a freezer. Frozen samples were then thawed and sampled for insulin content using a mouse insulin ELISA (Thermo). Microplate readings for absorption were recorded for both the pre- and post-EF insulin concentration.

PDX1 Immunostaining. βTC6 cells were seeded on glass coverslips at the density of 104 cells/cm2 and grown for 3 to 4 days. Following an EF treatment, the cells were fixed using 4% paraformaldehyde for 15 min, permeabilized using 0.25% Triton X100 for 10 min, and blocked using 1% BSA solution for 30 min. Samples were then immersed in 1% BSA solution with 3 µg/mL anti-PDX1 antibodies (Abcam) and incubated overnight at 4° C. The samples were then washed again and incubated at room temperature for 90 minutes with 1% BSA solution supplemented with 1 drop/mL of NucBlue (Thermo), and Alexa 488 conjugated secondary antibody at a 1:1000 ratio (Jackson Immunoresearch). The samples were mounted onto slides, imaged, and fluorescent intensity was measured and recorded.

Live/Dead Assay. A Live/Dead cell viability assay (Thermo) was used to rule out any adverse effects associated with the DCEF exposure. A sample was mounted on the chamber and exposed to 3 V/cm for 15 min, followed by the viability assay staining and imaging. A second sample was also mounted on the chamber for 15 min but without any electric field exposure. Percent viability was determined by the number of live cells (green fluorescence) divided by the total cell count.

Statistical Analysis. For statistical analysis of intracellular calcium, a two-sided paired t-test was performed on the Fluo-8 fluorescent intensities between post and pre time points. For calcium versus radial distance plot, a simple linear regression was performed with an evaluation of the Pearson coefficient after a modified Z score outlier test with z=3.5 removed 11 outliers. Insulin ELISA results were compared using a two-sided paired t-test. A two-sided unpaired t-test was performed for the intensity from the PDX1 experiments. Alpha for all tests was set to 0.05.

Cell culture. Insulinoma (βTC-6) mouse β-cells were purchased from ATCC (CRL-11506) and used as a model to study the effect of EF on β-cells. The cells were cultured in a high glucose (4.5 g/L) DMEM (Sigma) with 15% FBS (Gibco) and 1% Penicillin-Streptomycin according to the prescribed protocol. Cells were passaged using 0.25% Trypsin-EDTA and seeded on glass coverslips immersed in a low glucose (1.0 g/L) DMEM media. These samples were allowed to grow for 2 to 5 days at 37° C. and in a humidified 5% CO2 environment before being imaged.

Calcium Fluorescent Microscopy. Fluo-8, a calcium specific AM ester dye, was used to determine any changes in intracellular calcium. Samples were washed and stained with 0.8 µM Fluo-8 and 1 drop/mL Nucblue in Hanks Balanced Salt Solution (HBSS) for 30 minutes at 37° C. Samples were then loaded onto the EF chamber and imaged for calcium rise and spiking. Measurements for calcium rise recorded a single static image before and after EF exposure, while calcium spiking was recorded over 2 minutes before and after EFS with a 5 second sampling interval.

Calcium Image Analysis. For calcium rise, the mean intensity of clusters in the sample were measured at 0 minute (Pre) and 15 minute (Post) time points using Nikon Elements. Background subtraction was then performed and the percent change was determined by comparing the post-exposure to the pre-exposure mean intensities. For calcium spiking, regions of interest (ROIs) were generated over the nuclei of individual cells. The mean intensity over time was measured for both the pre and post imaging sessions. A moving average (n=10) was used as a baseline with a 10% (F/Fo) threshold for spiking determination. This was done account for the background rise in calcium along with filtering out noise. For spatial analysis, each cluster's ROI centroid coordinates (x, y) were determined along with the centroid coordinates for each cell's ROI. The radial distance for each cell from the center of the cluster was determined using the equation:

$$r = \sqrt{(x_{cell} - x_{cluster})^2 + (y_{cell} - y_{cluster})^2}$$

Each cells change in Fluo-8 intensity was determined and compared to its radial distance from its respective cluster's center.

Blocking Experimentation. Samples were imaged before and after EF stimulation for average calcium rise under differing buffer conditions. HBSS with calcium was used as the control, while calcium-free HBSS (supplemented with 0.8 mM magnesium) was used to demonstrate the calcium influx from the extracellular space. Verapamil (100 µM) was added to the HBSS staining solution and incubated for 30 minutes prior to imaging for testing the role of a calcium influx through L-type VGCCs.

Immunofluorecent Microscopy. Samples were imaged before and after EF stimulation for average calcium rise under differing buffer conditions. HBSS with calcium was used as the control, while calcium-free HBSS (supplemented with 0.8 mM magnesium) was used to demonstrate the calcium influx from the extracellular space. Verapamil (100 µM) was added to the HBSS staining solution and incubated for 30 minutes prior to imaging for testing the role of a calcium influx through L-type VGCCs Insulin Secretion. Samples for insulin secretion were seeded at 50,000 cell/cm2 three days prior to experimentation. Kreb's Ringer buffer (KRB) with 0.1% BSA was used for all steps in secretion (118.5 mM NaCl, 2.54 mM CaCl2, 1.19 mM KH2PO4, 4.74 mM KCL, 25 mM NaHCO3, 1.19 mM MgSO4, 10 mM HEPES, pH 7.4). Samples were first washed and incubated for 30 minutes in (KRB) without glucose at 37° C., and then KRB was replaced and samples were incubated another 30 minutes. Samples were then washed and mounted to the EF device and exposed to either no EF (control) or 3 V/cm EF for a total of 15 minutes. Following exposure, approximately 600 µL of solution was taken from the chamber at the area were the cells were exposed and was frozen. A mouse insulin ELISA kit from Thermofisher (EMINS) was used. All samples were diluted 1:10 for the assay reading.

CyQuant for Secretion. To normalize the insulin secretion, CyQuant (Thermo), a nucleic acid assay, was used to estimate the number of cells in each sample used for insulin secretion. Samples were first frozen at −20° C. and then lysed with 2 mL of CyQuant 1× lysing solution. A cell scrapper was used to suspend the cells and then 200 μL (1:10 dilution for assay) of the sample lysate were added to three wells for each sample in a black sided 96 well plate. CyQuant stain was then added to each well for a 2× concentration in accordance with the manufactures protocol for cell counts up to 100,000 cells.

Viability Experimentation. Samples were stained using Nucblue for all nuclei and Nucgreen for the nuclei of dead cells. All samples were mounted to the device and exposed to either no EF (sham) or EF at 1, 2, and 3 V/cm. Samples were then placed into new dishes, re-immersed in media, and placed inside the incubator overnight. The following day cells were stained and imaged. Nikon Elements auto generation for ROI was used to determine the total area of Nucblue (viable cells) or Nucgreen (dead cells). The percent viability was determined by the following equation:

$$\text{Viability (\%)} = \frac{(N - D)}{N} \times 100\%$$

Were N is the total area of all nuclei in the image and D is the total area of all the NucGreen stained nuclei in the image.

Statistical Analysis. A two-tailed paired t-test was used to determine significance between the pre and post conditions for all calcium experiments. For insulin secretion, a simple unpaired t-test was performed, while the viability testing used a one factor ANOVA with post-hoc multiple unpaired t-tests with bonferroni correction. An Iglewicz and Hoaglin's multiple outlier test (modified Z score of 3.5) was used for to detect outliers for spatial calcium results and insulin secretion. Analysis was performed using Microsoft Excel, Contchart software for outlier tests, and the plugin from Real Statistics Resource Pack.

Results

Cell viability. To determine if an external electric field caused any cytotoxic effects, βTC-6 insulinoma cells were exposed to 1, 2, and 3 V/cm electric fields for 15 min, and the cell viability was assessed as described above. A composite image (FIG. 1A) was constructed to illustrate representative cell viability tests using the three different EF strengths. Quantitative results demonstrated cell viability of approximately 90% or greater for all exposure conditions with no significant difference when compared to the sham experiments (FIG. 1B). Application of electric fields in range of 1 to 3 V/cm for 15 min exposure did not adversely affect the cell viability.

Figures 2A, 2B:
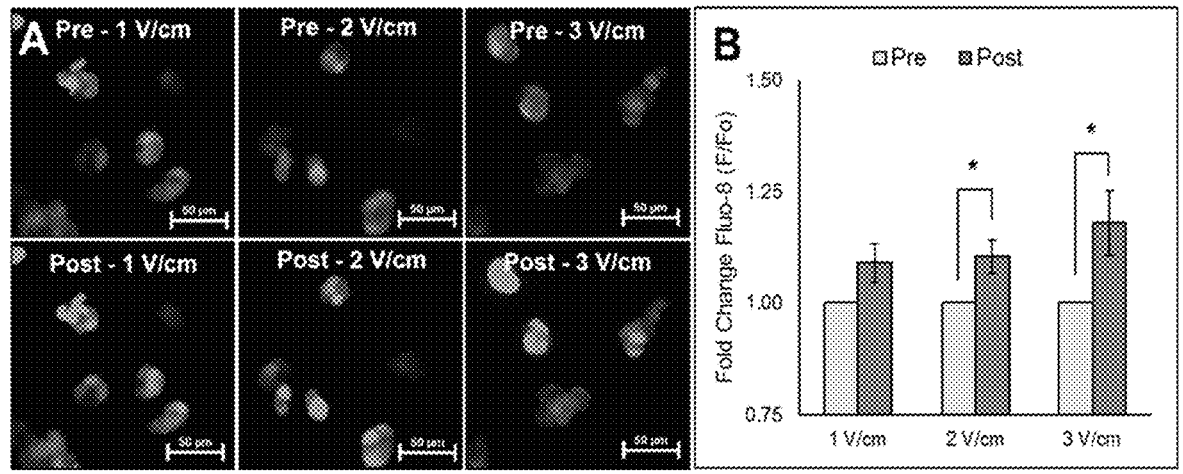
FIG. 2A shows representative images of intracellular calcium increase after 15 minutes of exposure to various EF strengths.
FIG. 2B shows average increase in intracellular calcium after the 15 minutes of exposure. Data represent 14, 11, and 10 independent samples for 1, 2, and 3 V/cm respectively. All error bars represent standard error of the mean. *p<0.05.

Intracellular Calcium Dynamics. Imaging for Fluo-8 intensity, βTC-6 insulinoma cells demonstrated an elevation in intracellular calcium that appeared to depend on the strength of the EF exposure. (FIG. 2A). Following the 15 minutes of exposure, the percent change in Fluo-8 intensity was measured to quantify the rise in intracellular calcium. The application of the three different electric field strengths induced a 9%, 11%, and 18% response to 1, 2, and 3 V/cm, respectively (FIG. 2B). As anticipated, application of a 1 V/cm EF did not induce a statistically significant elevation in the intracellular calcium level. This is consistent with the previous results that a weak EF (e.g., 1 V/cm) requires ~52 min exposure to illicit maximum changes, whereas only a 20 min exposure of a 3 V/cm EF should be sufficient to raise the intracellular calcium level. Because the exposure time was limited to 15 min to determine short-term effects, a 1 V/cm EF is not be sufficient in strength to elevate the intracellular calcium level.

Figures 3A, 3B:
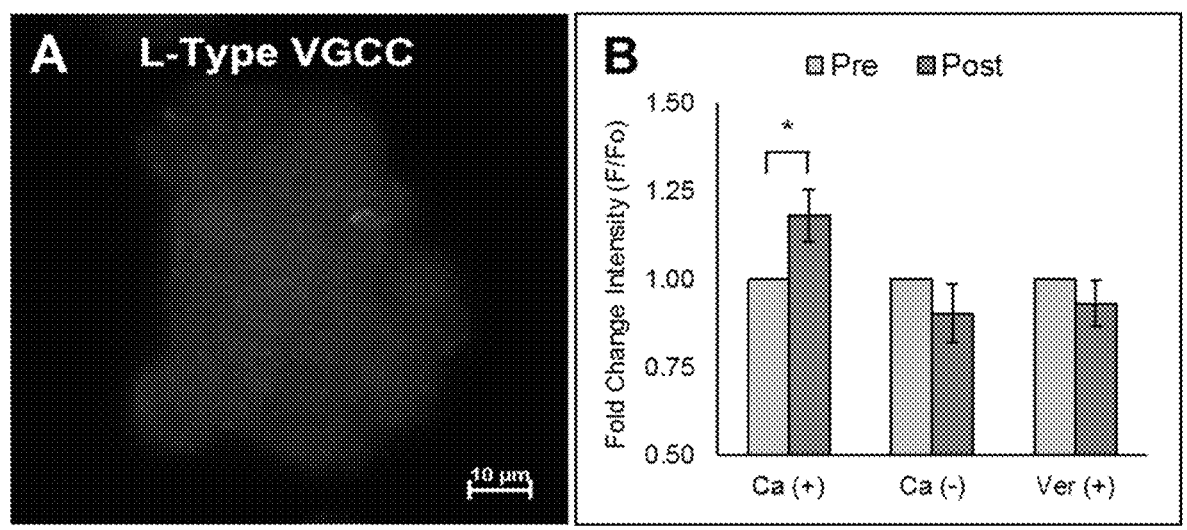
FIG. 3A shows anti-CaV1.3 fluorescent imaging demonstrating expression of L-type VGCCs in β-TC6 cells with counterstained nuclei.
FIG. 3B shows intracellular calcium increase after 15 minutes of exposure to 3 V/cm in Hanks solution, Hanks without calcium, and Hanks with a L-type VGCC inhibitor (verapamil) Data represents 10, 9, and 9 independent samples for the conditions respectively. The control data (e.g., normal Hanks solution) were repeated from FIGS. 2A and 2B. All error bars represent standard error of the mean. *p<0.05.

Potential calcium pathways that can mediate the EF-induced increase in the intracellular calcium level were probed. First, the presence of L-type VGCCs on the cells was confirmed using immunofluorescence. An abundant expression of L-type calcium channels stained with anti-CaV1.3 antibodies was clearly visible on the βTC-6 cells (FIG. 3A). Next, the calcium ions was depleted in the extracellular buffer. The removal of calcium from the buffer inhibited any rise in intracellular calcium in response to a 3 V/cm EF (FIG. 3B). This indicates that an influx across the cell membrane was responsible for the EF-mediated calcium rise. Based on previously reported findings, and the immunofluorescent images recorded (see FIG. 3A), it is plausible that L-type VGCCs were one of the dominant pathways for the calcium influx. To demonstrate the role of L-type VGCCs, cells were incubated with a specific L-type channel inhibitor (verapamil) prior to EF exposure. Verapamil effectively blocked the increase in intracellular calcium level (FIG. 3B), providing evidence that the L-type channels have been activated.

Figures 4A, 4B:
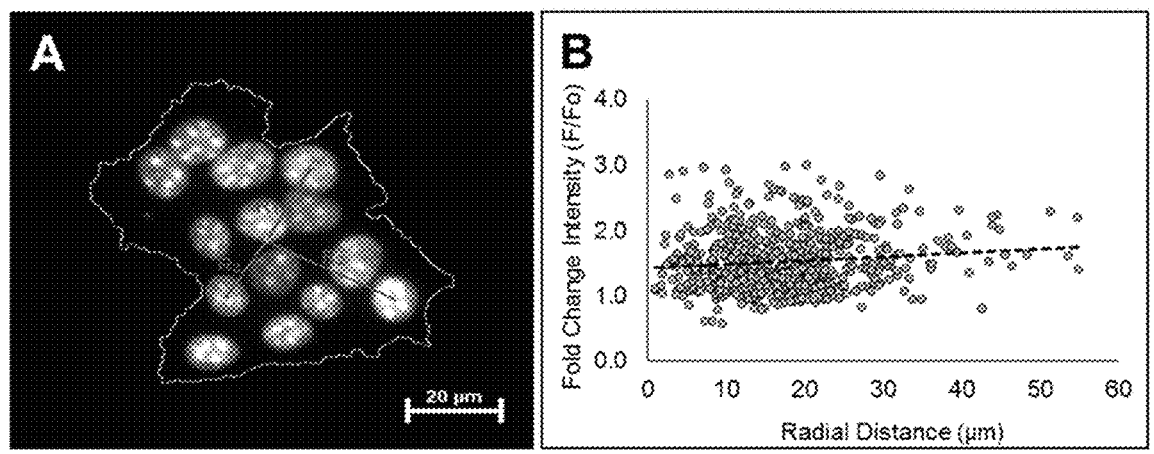
FIG. 4A shows illustrative image of positional ROI's and how distance from cluster center was determined.
FIG. 4B shows fold change in individual cell's Fluo-8 intensity in response to an EFS (3 V/cm) with respect to distance from its cluster's center. Data represent 547 cells exposed to the EF.

Given that these βTC-6 cells grow in clusters and VGCCs are affected by the local field strength, the location of each individual cell within a cluster can alter its intracellular calcium response to the electrical stimulation. This is because cells at the periphery of a cluster experience the full impact of an EF, but cells near the center are shielded. While the average response of the clusters was determined, variation within a given cluster can be explained by the shielding effect. The centroid of each cell was determined based on the location of its nucleus, and then the centroid of its respective cluster was determined. The radial distance from the centroid of each cell to the centroid of its cluster was calculated. As an illustration, in FIG. 4A, three cells within a cluster were randomly selected, and the distance from each cell to the center of the cluster was denoted by $R_1$, $R_2$ and $R_3$. Such a strategy of data analysis led to establishing a correlation between the Fluo-8 intensity of each cell and its location relative to the cluster's center (FIG. 4B). Using a linear regression, a 5.8% increase was observed for every 10 μm the cell was located away from the cluster's center. A Pearson coefficient of 0.12 was calculated indicating that other factors are also affecting the cellular response to the EF in addition to the shielding effect.

Figures 5A, 5B, 5C:
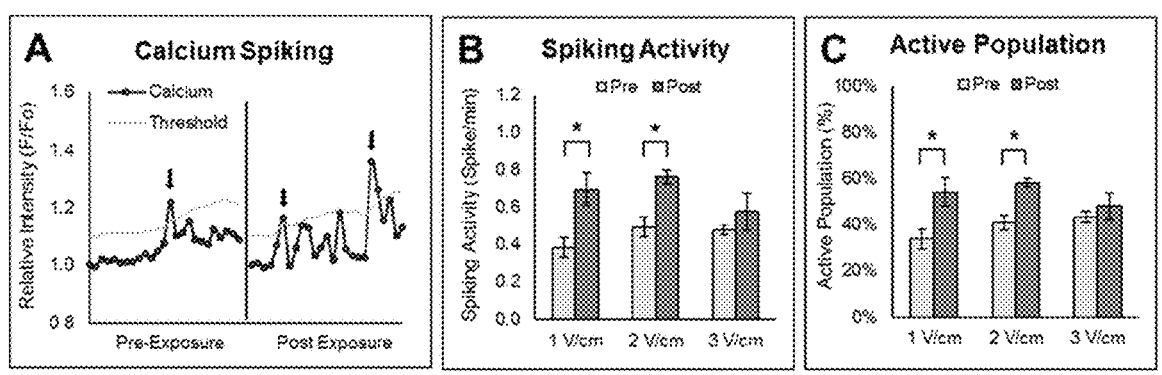
FIG. 5A shows calcium tracing of a cell before and after EFS at 3 V/cm (black line) alongside the moving average threshold (gold line). A moving average was used to account for background calcium increase and to reduce noise.
FIG. 5B shows mean spiking frequency of all measured cells before and after exposure, against all EF strengths.
FIG. 5C shows the average percentage of the population found to spike at least once during the observation time period before and after EF exposure. Both spiking activity and active population represent 10, 10, and 9 independent samples for 1, 2, and 3 V/cm respectively. All error bars represent standard error of the mean. *$p<0.05$.

Insulin secreting cells have been shown to depend critically on intracellular calcium levels as well as the calcium dynamics (e.g., calcium spiking). In an effort to understand the effects of EFs on calcium spiking, the Fluo-8 intensity was recorded over a 2 minute imaging window before and after the EF was applied. The baseline calcium level did not remain stable but varied during the calcium spiking recording (FIG. 5A). This presented a challenge in defining a calcium spike. For example, using a constant baseline can lead to an excessive estimate of calcium spikes due to the changing baseline. Therefore a moving 10 data point average threshold was applied and a calcium spike is scored if the Fluo-8 intensity was at least 10% above the moving average baseline (FIG. 5A). Mean activity was defined as the total number of spikes recorded over time divided by the number of cells being measured. The mean calcium spiking activity following the EF stimulation was found to increase in response to a 1 or 2 V/cm but not 3 V/cm EF (FIG. 5B). There was also a change in the number of cells showing active spiking. The percentage of cells that spiked at least once during the observation time period was compared between pre- and post-exposure (FIG. 5C). Again, both 1 and 2 V/cm but not 3 V/cm EF were found to significantly increase the percentage of actively spiking cells.

Figure 6:
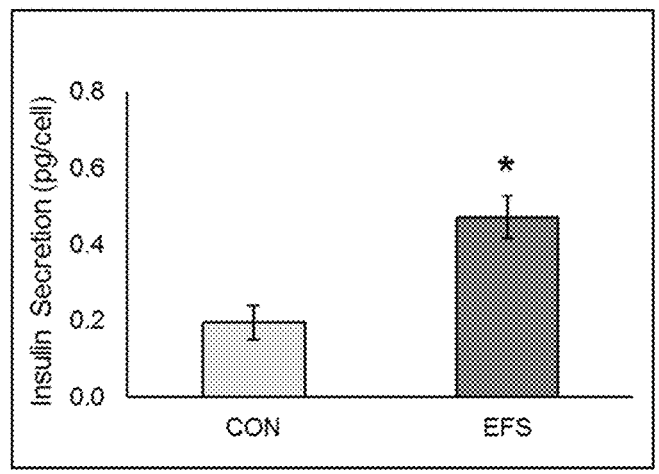
FIG. 6 shows average insulin secretion per cell for 0 mM glucose (CON) and 0 mM glucose and 3 V/cm EF exposure after 15 minutes. Data represent 7 and 8 independent samples over 3 separate experiment sets for CON and EFS, respectively. Error bars represent standard error of the mean. *$p<0.05$.

Given that calcium directly activates insulin granule exocytosis, the next experiment aimed to determine if the EF stimulates insulin secretion even in the absence of glucose in response to a 3 V/cm EF, since this EF strength demonstrated the greatest rise in intracellular calcium level. All samples were mounted on the device and immersed in glucose free Kreb's Ringer buffer. By sampling the buffer after stimulation, the total insulin secretion was determined. Using a nucleic acid assay (CyQuant) enabled the determination of average insulin secretion per cell. In response to a 3 V/cm EF for a 15 min exposure, the insulin secretion per cell demonstrated a >2-fold increase (FIG. 6). This is a significant rise in intracellular calcium that produces more total insulin secretion than small transient rises derived from calcium spiking.

Figures 7A, 7B, 7C, 7D:
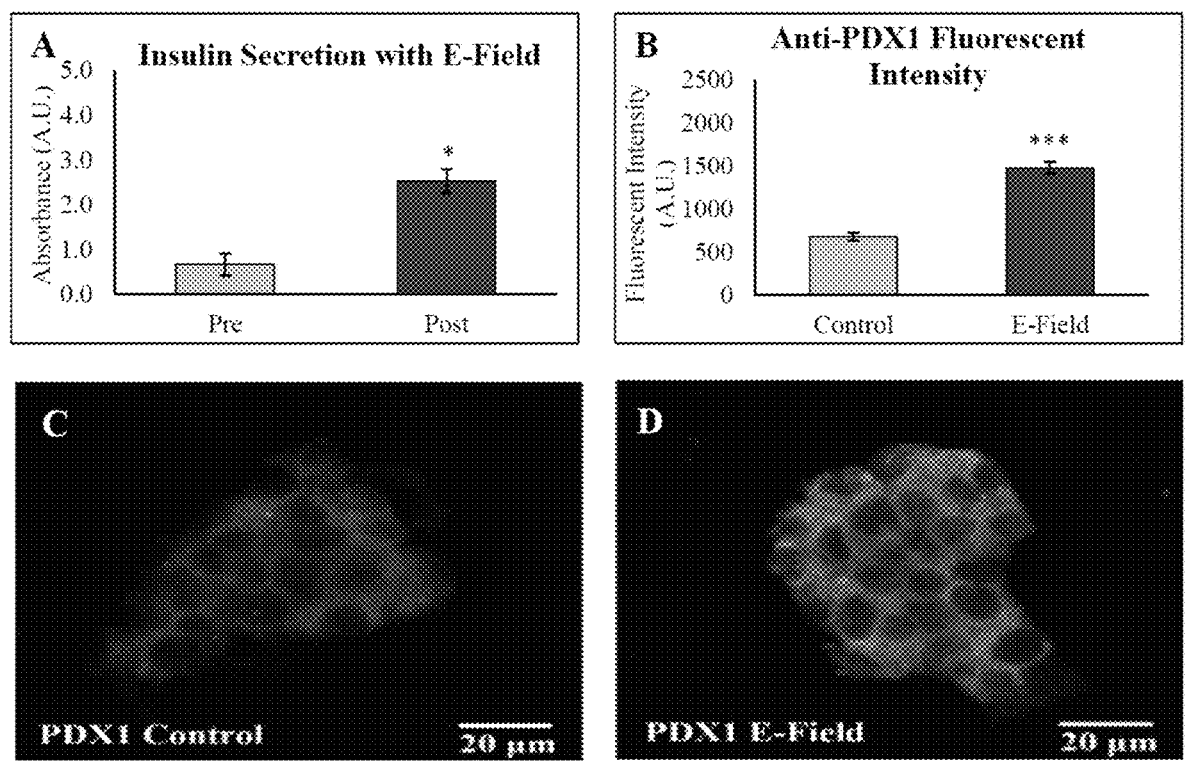
FIGS. 7A-7D show effects from DCEF exposure on insulin secretion and PDX1 expression.

Effects on insulin secretion and PDX1 expression. An increase in intracellular calcium in βTC6 cells can facilitate insulin secretion. Therefore, changes in insulin secretion due to exposure to the DCEF were next determined. First, the samples were incubated in PBS for 30 minutes to remove any free insulin before taking measurements. The cells were then incubated 1 hour to determine the baseline secretion, followed by a 15-minute exposure to the DCEF, and followed by another hour incubation. The relative concentration of insulin before and after DCEF exposure was determined using an insulin ELISA assay and a microplate reader for absorbance. The results indicated a significant rise in insulin secretion following the DCEF exposure (FIG. 7A). A rise in intracellular calcium can also affect various protein kinases, in particular protein kinase C (PKC). Given that an elevation in PKC can exert an effect on PDX1 levels, whether exposure to the DCEF leads to an increase in the PDX1 expression was investigated. Cells were then exposed to the DCEF 15 minutes, followed by an additional 15 minutes of incubation, compared to a control group with no exposure. These groups were then fixed and immunostained with anti-PDX1 and imaging for average fluorescent intensity. The results yielded ~2-fold increase in intensity (FIG. 7B). Representative fluorescent images of PDX1 were shown in FIG. 7C and FIG. 7D.

Cell viability following DCEF exposure. To ensure the cell viability has not been impacted by the DCEF, a Live/Dead fluorescent staining kit was applied to determine the viability of samples exposed to the DCEF versus control cells. Analysis yielded an approximate viability of 92% for the exposed sample versus 98% viability of control cells, indicating that exposure to the DCEF had a negligible effect on the cell viability.

Discussion

The aim of the study was to apply physiologically relevant electric fields (e.g., 1-3 V/cm DC electric field; DCEF) while limiting the exposure time to focus on the short term effects (e.g., 15 min exposure). Under these exposure conditions, direct activation of the L-type VGCCs by the DCEF is unlikely since a 3 V/cm EF strength only induces a small membrane voltage differential. For example, considering a typical β-cell cluster ~50 μm in size, it can be considered as an electrical insulator in response to a direct current EF. The membrane potential change is ~15 mV, not sufficient to depolarize the membrane potential. Instead, many laboratories have repeatedly demonstrated that the charged cell surface receptors can be redistributed on the cell surface in response to an external electrical stimulation.

The diffusion and electromigration coefficients of cell surface receptors have been measured using various experimental techniques including fluorescence recovery after photobleaching (FRAP). The lateral diffusion coefficients (D) in the membrane plane are in the range of $10^{-9}$ and $10^{-11}$ cm$^2$/s, and the electromigration coefficients (μ) in the range of $10^{-6}$ (cm/s)/(V/cm). The distance traversed by random movement is described by $X_D=(4D\ t)^{1/2}$, and that by electromigration is $X_E=\mu E\ t$. The characteristic time after which the electromigration becomes dominant can be estimated by assuming the ratio of $[(4Dt)^{1/2}/(\mu Et)]$ to be 0.05, e.g., 5% of the distance traversed by electromigtation. Assuming D=$10^{-10}$ cm$^2$/s, the characteristic time is calculated 15 min. It has been shown that the charged surface receptors do indeed redistribute, and that selection of the exposure time of 15 min was carefully chosen based on this prediction in order to mitigate the effects of redistribution. As seen in fibroblast cells, an EF of 10 V/cm for an hour was required for an 80% asymmetrical redistribution of charged surface receptors.

For comparative purposes, one can also estimate the time that is required to induce a similar cell surface receptor redistribution if a 1 V/cm EF was applied (~45 min). This time estimate is consistent with the previous results that a weak 1 V/cm EF was applied for >50 min to induce maximal changes in the intracellular calcium level.

Although the estimated change in membrane potential is small and can be insufficient to induce membrane depolarization, it can nonetheless increase calcium influx through several potential mechanisms. During EF exposure, the shift in membrane potential can lead to the redistribution of charged cell surface receptors along with alterations in other ionic currents. For example, the sodium channels can be more sensitive and respond to the 15 mV change attributed to exposure to a 3 V/cm EF. These events can further influence the membrane potential yielding a direct effect on the magnitude of the calcium current. This rise in the electromotive force for calcium can increase the rate of calcium entry across open VGCCs, thus elevating the cytosolic calcium concentration. Once the applied EF is removed, an increased activity in calcium dynamics gradually decreases. Within a 60 min observation time period post-field, the calcium spiking activity appeared to be abated but remained above the baseline.

These β-cells typically grown in clusters. Since cellular membranes acts as electrical insulators, cells at the periphery of the cluster can experience a stronger local EF than those at the cluster's center. If so, cells near the cluster's edge can demonstrate a greater response to the EFS than those near the center. This question was addressed by first determining the centroid of each cell's nucleus along with its respective cluster's centroid. One can then calculate each cell's radial distance from the center of its cluster. As shown in FIG. 4, a suppressed calcium elevation was observed in cells near the cluster's center, while cells near the perimeter had greater calcium elevations. Such data analysis shows that the EF differentially affects a given cell's intracellular calcium level depending on its spatial location within a cluster. Optimization of electrical stimulation for therapeutic purposes can overcome this type of shielding effect.

Since calcium spiking is thought to be an integral part of β-cell physiology, the effects of EF exposure on calcium spiking activity was determined. It has been seen in neuronal cell types that weak electrical stimulation can modulate the spike timing and frequency of depolarization events. Since depolarization spiking trains are responsible for the calcium spiking events, it follows that an increase in electrical activity can lead to an increase in calcium activity. From these results, it was clear that EF exposure did influence calcium spiking activity along with increasing the number of active cells. The data demonstrated an inverse relationship between calcium accumulation and calcium spiking activity. Since L-type VGCCs are known to be sensitive to calcium dependent inactivation (CDI), it can be that the significant rise in intracellular calcium brought about by a stronger EF (e.g., 3 V/cm) interferes with the calcium spiking machinery thus reducing calcium spiking frequency. This response can be a protective mechanism to prevent the cytotoxic effects of calcium overload.

Since insulin secretion directly depends on a rise in intracellular calcium, the capacity of EFS to induce insulin secretion in the absence of glucose was determined. Following the initial observations on calcium accumulation, the EF strength of 3 V/cm was chosen since it had the greatest effect on intracellular calcium. The results demonstrated the ability of EFS to induce insulin secretion even in the absence of glucose. Since calcium is the direct trigger for insulin secretion, the significant rise in calcium due to EFS corresponds with insulin secretion. A commonly used method to induce insulin secretion is exposure to high concentrations of potassium chloride (KCl). This depolarizes the cellular membrane resulting in a dramatic and sustained elevation in intracellular calcium via L-type VGCCs. Calcium elevation via KCl exposure can induce a stronger initial insulin release than glucose and appear to differentially affect granule turnover rate. The mechanisms by which EFS stimulates insulin secretion can be similar to those of KCl-induced insulin secretion.

Altered β-cell physiology in response to the electric field-induced rise in intracellular calcium is rather complex. For example, the expression of the transcription factor PDX1 can be modulated due to the activation of various calcium dependent signaling pathways. An elevation in the anti-PDX1 immunofluorescent intensity of the βTC6 clusters was observed following the DCEF exposure. This corresponds to an increase in PDX1 protein abundance within the cells. While it has been shown that IL-V can increase PDX1 expression via PKC activation, the important isoform PKCδ is not calcium dependent. However, PKCδ does respond to an increase in diacylglycerol by phospholipase C (PLC). Electric field can activate the membrane-bound PLC that can lead to an increase in DAG and thus affects the PKC activity. Mild electrical stimulus can enhance the expression of PDX1 within pancreatic progenitors from embryonic stem cells. PDX1 upregulation can be due to the EF effects on the PI3K/Akt pathway. Alternatively or concurrently, an increase in PDX1 can also be due to a reduction in its degradation via the inhibition of glycogen synthase kinase 3 beta (GSK3β). Both PKC and Akt inhibit GSK3β activity and thus can allow for an increase in PDX1 accumulation. In addition, PKCα is calcium dependent and positively regulates Akt which can further be driving the response. While the mechanism is yet to be fully elucidated, the ability of a DCEF to increase PDX1 expression can be useful in improving the functionality, maturity, and survivability of β-cells. The data that this DCEF stimulation can upregulate critical transcription factors in β-cells indicate long term alterations in protein expression due to repeated exposure events.

The present disclosure shows a measurable increase in intracellular calcium with β-cells exposed to an exogenous EF likely mediated by L-type VGCCs on the cellular membrane. Additionally, the observed increase in intracellular calcium is dependent on each cell's spatial location within a cluster of cells. The elevated calcium level was shown to induce insulin secretion from βTC6 cells. The PDX1 expression is upregulated and correlated with the calcium-dependent and DCEF-induced increase in insulin secretion. Collectively, non-invasive exogenous EFs prove useful in therapeutics by improving the functionality of insulin producing cells either from donated islets or stem cell-derived.

It is shown herein that a DCEF is able to modulate both the intracellular calcium concentration and the spiking activity, which appears to be inversely related with the strength of the EF. Although a longer exposure of EFS can result in a greater insulin secretion, it was demonstrated herein that even a 15 min exposure was sufficient to induce insulin secretion despite an absence of glucose. This shows a novel non-pharmaceutical therapy to modulate intracellular calcium and stimulate dysfunctional β-cells.

Example 2. Stimulatory Effects of Near-Infrared (810 Nm) Photobiomodulation on Calcium Dynamics and Insulin Secretion in B-Cells Introduction Over the last 50 years, low level laser therapy (LLLT) has been investigated for use in various medical applications. However, the cellular mechanisms by which this method provides its therapeutic effects has not been rigorously explored until recently. Now more commonly known as photobiomodulation (PBM), it has been shown to effect Cytochrome C Oxidase (CCO) activity, mitochondrial reactive oxygen species (mROS), and intracellular calcium levels. By influencing these physiological functions, PBM has been shown to modulate stem cell differentiation and impart an increased resistance to oxidative stress.

Given these effects, PBM can be used to modulate β-cell physiology and thus insulin secretion in response to glucose load. Insulin secretion is canonically initiated by elevations in ATP, leading to depolarization and calcium influx and driven by the resulting rise of intracellular calcium. The effects of PBM on calcium dynamics mediated by the pathways other than ATP elevation can also lead to insulin secretion.

β-cells are an electrically active cell type displaying spontaneous calcium spiking behavior. These patterns of calcium spiking influence a wide array of cellular functions including transcription factor expression, apoptosis and survival, and in particular exocytosis of insulin granules. Calcium spiking frequency directly affects pulsatile insulin secretion. When challenged by a glucose load, the β-cell spiking frequency and activity increase that spurs insulin secretion. Thus PBM can emulate or alter β-cell calcium dynamics and subsequently regulate their insulin functionality.

The current mechanistic theory shows that near-infrared light (NIR) can be absorbed by CCO and disassociates nitric oxide (NO) binding. This disassociation allows for an increase in oxygen binding, thus increasing the rate oxidative phosphorylation. The rise in oxidative phosphorylation increases ATP production and is accompanied by an increase in mROS generation. While signaling by mROS and NO have been shown to be involved in insulin secretion, the primary driver of insulin secretion is intracellular calcium and thus remained the focus of our investigation.

While a shift in the ATP/ADP ratio causes depolarization with activation of voltage gated calcium channels (VGCCs), it has been shown that transient receptor potential calcium channels (e.g., TRPV1) are also activated by NIR light. Blocking these channels inhibit the effects of NIR PBM on intracellular calcium thus supporting the involvement of TRPV channels. However, other groups have shown that calcium spikes can be initiated by NIR-PBM and inhibited by various intracellular calcium channel blockers. Since these photons transmit through the entire cell, absorption by various chromophores is likely to result in a complex and multifaceted response.

Materials and Methods

Cell Culture. Mouse insulinoma cells (βTC-6) were obtained from ATCC (CRL-11506, Manassas, VA) and cultured in high glucose DMEM (D6429, Sigma, St. Louis, MO) with 15% FBS (Ser. No. 16/000,044, Gibco) and 1% Penicillin-Streptomyzin. Cell passage was performed weekly with 0.25% Trypsin-EDTA. Samples were prepared by seeding βTC-6 cells on glass coverslips in low glucose media. These samples were used for experimentation between days 2 through 5. All cells were incubated at 37° C. in a 5% $CO_2$ environment.

PBM Parameters. A Cytonsys (Austin, TX) 810 nm near-infrared laser was used to perform all experimentation. Previous reports have demonstrated therapeutic effects of this wavelength on various cell types. The energy density of 9 $J/cm^2$ was previously shown to have therapeutic effects on hepatic tissue in a diabetic state. In addition, 810 nm PBM stimulation at the fluence of 10.2 $J/cm^2$ was shown to have therapeutic potential as a diabetic therapy on mice. Densities higher than 10 $J/cm^2$ have been shown to exhibit inhibitory effects. Herein, all βTC-6 samples were exposed to 810 nm for 1 minute with an irradiance of 150 $mW/cm^2$, resulting in a fluence of 9 $J/cm^2$. To measure the bulk temperature rise that was due to laser exposure, an Omega HH42A thermistor was used before and after irradiation.

Live Cell Imaging. For calcium and mitochondrial superoxide (mROS) detection, the cells were stained with Fluo-8 (0.8 μM, Abcam, Cambridge, UK), Mitosox (5 μM, Thermo-Fisher, Waltham, MA) and 1 drop/mL of Nucblue (Thermo-Fisher, Waltham, MA) for detection of intracellular calcium, mROS, and nucleic acid, respectively. The fluorescent dye DAF-FM (5 μM, Thermo-Fisher) was used to detect and measure cytosolic nitric oxide (NO). Hanks balanced salt solution (HBSS) was used (H8264, Sigma, St. Louis, MO) unless stated otherwise. Samples were stained at 37° C. for 30 minutes before being washed and mounted onto the imaging chamber.

Calcium Activity Analysis. Regions of interest (ROIs) were placed on individual cells using the nucleic acid staining and transferred to perform and calculate mean fluorescent intensity over time with background subtraction. Approximately 100 to 200 cells were monitored for each data point, and the results were averaged. A conservative moving average threshold (10 data points) with a 10% cutoff was used to determine a calcium spike. (see FIG. 8A) Any cell that displayed at least one spike above the moving threshold during each imaging window was defined to be active. The active population was defined by the total number of active cells divided by the number of cells analyzed. The average spiking frequency of these active cells was then determined at each time point. Measurements were taken using Nikon Elements software and data analysis was carried out using Microsoft Excel. Heat mapping of calcium activity was produced using ImageJ by taking the absolute difference between 2 frames and summing the differences together. A Gaussian smoothing was performed in ImageJ to remove background noise.

Pharmacologic Studies. All drugs were added to the staining buffer. Samples were treated with each drug for 30 minutes before imaging. For L-type VGCC blocking, Verapamil (100 μM, V4629, Sigma) was applied. Capsazepine (10 μM, C191, Sigma) was added as a TRPV1 antagonist. Dantrolene (50 μM, 251680, Sigma) and 2-APB (10 μM, 100065, Sigma) were used to inhibit the Ryanodine- or $IP_3$-receptors respectively. Ascorbic Acid (2.5 mM, A0278, Sigma) was used as an antioxidant to diminish the effects of ROS.

Insulin Secretion Assay. Krebs Ringer Buffer (KRB) was made (118.5 mM NaCl, 2.54 mM $CaCl_2$, 1.19 mM $KH_2PO_4$, 4.74 mM KCL, 25 mM $NaHCO_3$, 1.19 mM $MgSO_4$, 10 mM HEPES, pH 7.4), followed by 0.1% bovine serum albumin being added before insulin secretion experiment. Either 0.5 mM or 3.0 mM glucose was added to simulate a low or high glucose loading. Samples were seeded at 40,000 cells/$cm^2$ three days before experimentation. Samples were then washed with 0 mM KRB and incubated for 1 hour without glucose. Following an additional wash, samples were mounted to the chamber with the appropriate glucose concentration and with or without laser irradiation. After 15 minutes, samples were removed and frozen. A mouse insulin ELISA (EMINS, Thermo-Fisher) was used to measure insulin content with a 1:10 dilution. Cyquant (C7026, Thermo-Fisher), a nucleic acid assay, was used to estimate the number of cells for each sample and normalize the total insulin by the estimated number of cells.

Immunostaining. Cell samples were first washed and fixed for 15 minutes in 4% paraformaldehyde and permeabilized using 0.25% Triton-X100 for 10 minutes. BSA (1%) blocking was then performed for 30 minutes. Primary staining for L-type VGCC utilized 1:100 primary anti-CaV1.3 (Abcam AB85491) while staining for TRPV1 used 1:1000 anti-VR1 (Abcam, AB31895) with overnight staining at 4° C. Secondary staining was performed at room temperature for 90 minutes with 1:200 anti-mouse Alexa 555 for CaV1.3 and 1:200 anti-rabbit Alexa 488 for TRPV1. Samples were then washed and imaged.

Statistical Analysis. For calcium spiking frequency, each group was screened for outliers using Iglewicz and Hoaglin's test with a modified Z score of 3.5. To determine significance for the effects of PBM, a one-way repeated measures ANOVA was performed followed by pairwise t-tests between each time point and the baseline with Holms-Bonferonni correction. Significance between PBM time points and all pharmacological runs was determined using pairwise t-tests also utilizing Holms-Bonferonni correction. Unpaired t-tests were used to test between the 0.5 mM and 3.0 mM glucose insulin secretion groups. All data was processed using Microsoft Excel with the Real Statistics Resource Pack. Outlier tests were performed using Contchart software.

Results

Bulk Temperature Rise. Laser irradiation can induce heating. Before proceeding with quantitative determination of PBM effects, it is important to delineate potential temperature rise due to laser exposure. A thermistor was used to measure the temperature in the media. After 1 minute of 810 nm exposure at 150 $mW/cm^2$, the average bulk temperature rise was 0.08±0.02° C. This is well below the suggested threshold of 1° C. that might induce non-negligible thermal effects.

Figures 8A, 8B, 8C, 8D:
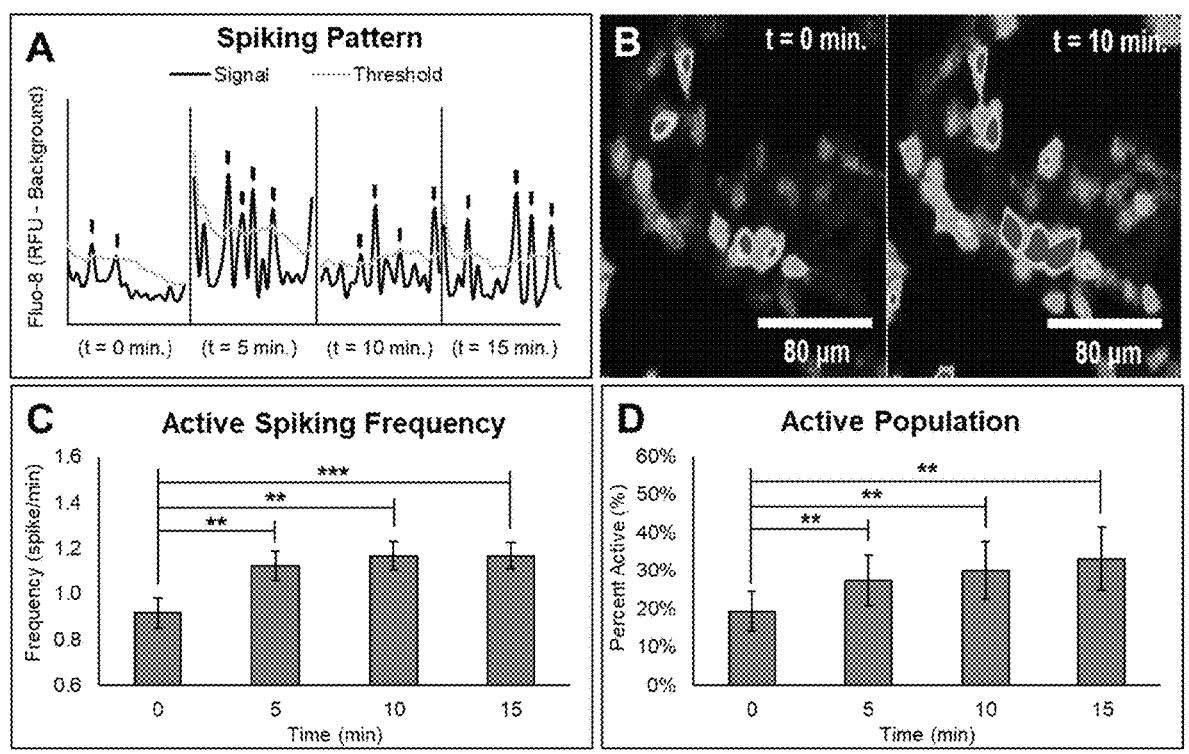
FIG. 8A shows representative trace of Fluo-8 signals alongside a 10-point moving average threshold with indicators (dark arrows) for calcium spikes. Background was subtracted from the fluorescent intensity.
FIG. 8B shows heat map images of the summed absolute difference between frames yielding a visual representation of calcium activity. Blue to red indicates low to high spiking activity.
FIG. 8C shows mean spiking frequency for active cells (e.g., 1 or more spikes) of >1,200 cells from 18 independent experiments.
FIG. 8D shows percentage of the active population. All data represent mean±SEM. $p<0.01$ and *$p<0.001$.

Calcium Spiking Response. How PBM can affect the intracellular calcium dynamics in the β-cell phenotype was determined. Using the fluorescent probe Fluo-8, calcium spiking activity in βTC-6 cells can be recorded. Using a 10-point moving average with 10% threshold for quantifying calcium spikes, a significant increase in calcium activity was observed following PBM exposure. (FIGS. 8A and 8B)

Active cells were defined as any cell with at least one spike during an imaging window. Of these cells, a significant increase in frequency from 0.92±0.07 to 1.17±0.06 spikes per minute was observed. (FIG. 8C) In addition to elevating the spiking frequency, the number of active cells increased following the irradiation. The average proportion of active cells was found to increase from 19.3±5.2% to 33.2±8.3% after PBM. (FIG. 8D) These results demonstrated that 810 nm PBM is capable of stimulating the calcium activity in β-cells.

Figures 9A, 9B, 9C, 9D:
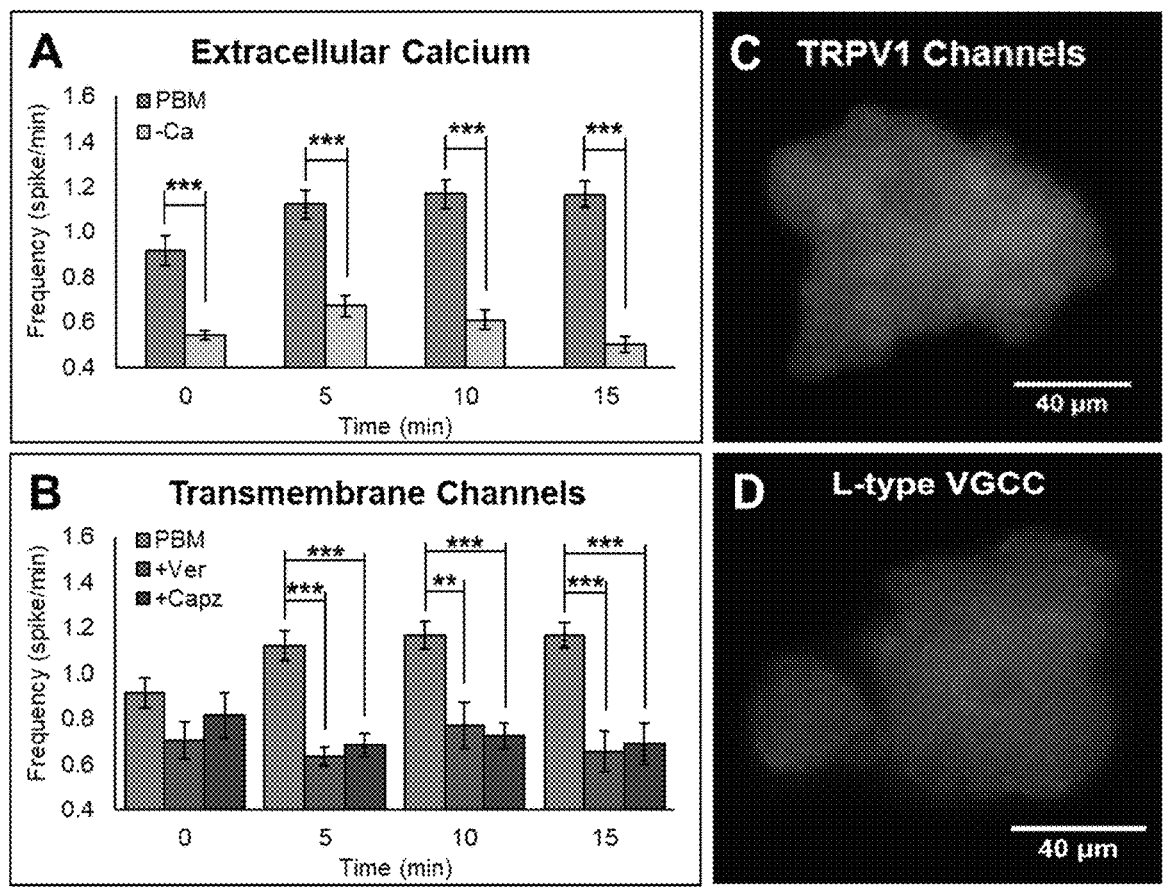
FIGS. 9A-9D show that calcium influx across the cell membrane.

Extracellular Calcium and Entry Pathways. In an effort to understand the mechanism(s) by which PBM exerts these effects, the dominant source of calcium rise was determined by depleting the extracellular calcium ions. This significantly impeded the spiking frequency following PBM exposure. This indicates that the primary source of calcium influx was across the cell membrane and into the cytosol. (FIG. 9A) Since the cell membrane has several pathways to mediate calcium influx, both L-type VGCCs and cell membrane TRPV1 channels were blocked using Verapamil and Capsazepine, respectively. Calcium spiking frequency between the PBM-treated group and those treated with PBM and channel blockers was significantly different, indicating both L-type VGCCs and TRPV1 channels are involved in the rise of calcium spiking activity by PBM. (FIG. 9B) Capsazepine was intentionally selected because it is membrane-impermeant (Millipore-Sigma). This indicates that the TRPV1 channels expressed on the cell surface were preferentially blocked. However, immunolabeling experiments showed both of these two channels are abundantly expressed in βTC-6 cells (FIGS. 9C and 9D). Thus these pharmacological studies alone were not be able to directly delineate the role of the two channel types in response to PBM stimulation.

Figures 10A, 10B:
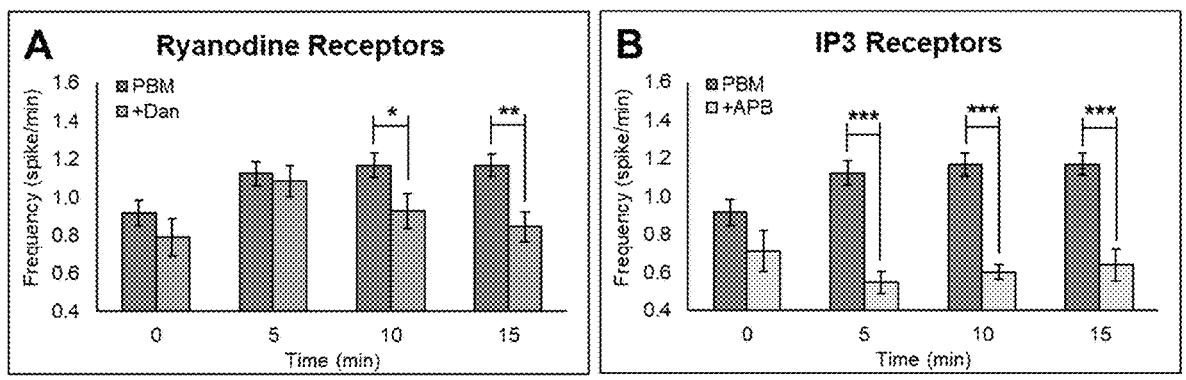
FIGS. 10A-10B show involvement of intracellular calcium store.

Intracellular Calcium. Despite the dominant influx of calcium from the extracellular space, one cannot readily rule out the contribution of PBM-induced activation of intracellular stores. Thus, the cells were treated with either dantrolene or 2-APB to inhibit the Ryanodine- and IP$_3$-receptor mediated intracellular calcium release. While the spiking frequency of dantrolene-treated samples was decreased in comparison to the control, this difference was only noticeable at the 15-minute mark. (FIG. 10A) However, a treatment with 2-APB to inhibit the IP$_3$-receptor-mediated pathway was shown to significantly impede such an increase in the calcium spiking frequency by PBM. (FIG. 10B).

Figures 11A, 11B, 11C, 11D:
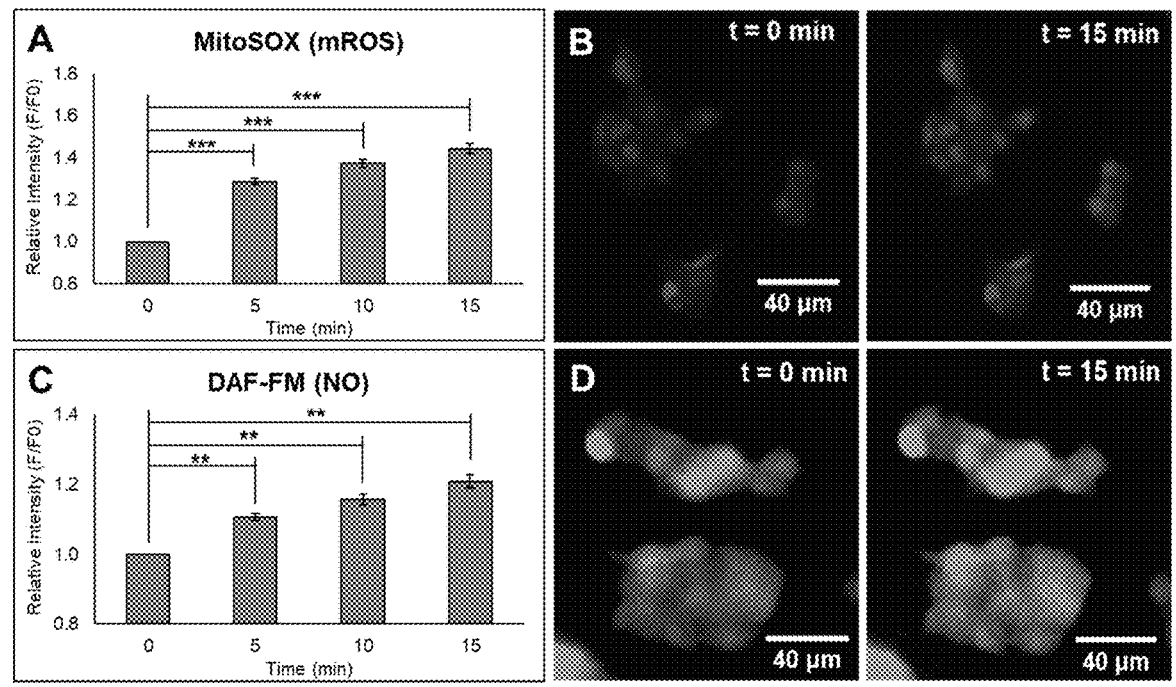
FIG. 11A shows normalized increase in Mitosox intensity over baseline value following PBM irradiation from 12 independent experiments.
FIG. 11B shows representative images demonstrating the rise in Mitosox intensity pre- and 15-minute post-irradiation.
FIG. 11C shows normalized increase in DAF-FM intensity over baseline value following PBM irradiation from 5 independent experiments.
FIG. 11D shows representative images demonstrating the rise in DAF-FM intensity pre- and 15-minute post-irradiation. Date represents mean±SEM. *$p<0.05$, $p<0.01$, and *$p<0.001$.

ROS and NO Elevations. In addition to apparent direct effects on TRP channels by PBM (see FIG. 9), it is well documented that CCO activity can also be increased by PBM. This should result in an increased production of ROS and NO. To verify this, the superoxide fluorescent probe MitoSOX was used to observe changes in mROS (superoxide). Following PBM irradiation, a maximum rise of 44.3±2.3% was observed at the 15-minute mark over the baseline level. (FIGS. 11A and 11B) In the same PBM-induced CCO activation model, cytosolic NO is also known to increase as NO dissociates from the heme group of CCO. The molecular probe DAF-FM was then used to measure the relative levels of cytosolic NO. Measuring its fluorescent intensity, a maximum rise of 20.8±1.8% in 15 minutes was observed. (FIGS. 11C and 11D) These results are consistent with and support the mechanism of PBM on CCO activity in β-cells by dissociating NO and resulting in an increase in mROS.

Antioxidants to reverse PBM-induced ROS increases. Given the influence ROS has on calcium dynamics, how the suppression of mROS affects the calcium spiking frequency was determined. Therefore, the samples were treated with ascorbic acid (AA) and a significant reduction in the Mito-SOX intensity was observed. (FIG. 12A) The spiking frequency of active cells treated with AA was next analyzed. There was no significant difference in the calcium spiking frequency analysis between the AA-treated and control cells until the 10-minute time point. (FIG. 12B). An increase in the ROS level at the early stage of PBM stimulation (<10 minutes) can be abrogated by AA and yet has no significant impact of the calcium dynamics, indicating ROS is not interfering with activation of the calcium channels at the cell membrane level. At later stages (>10 min), ROS-mediated calcium release from intracellular calcium stores is inhibited by AA and therefore diminishes the calcium spiking activity. Thus, mROS can act to sustain the calcium spiking patterns through ROS-dependent intracellular calcium release pathways.

Figure 13:
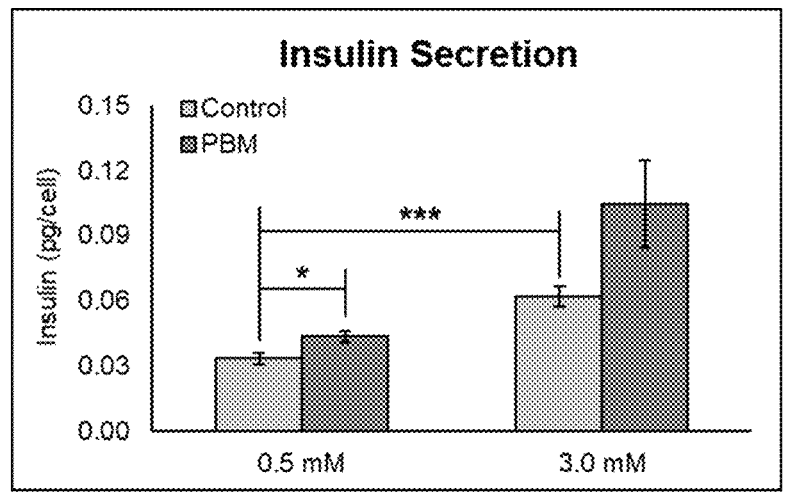
FIG. 13 shows insulin secretion under different glucose loading in presence of either 0.5 mM and 3.0 mM glucose in Krebs ringer buffer, the cells were expose to PBM and the insulin secretion was measured using ELISA assay. Data represent mean±SEM from 8 independent experiments. *$p<0.05$, $p<0.01$, and *$p<0.001$.

Insulin Secretion. Finally, how the stimulation of PBM-induced calcium dynamics affects insulin secretion was determined. βTC-6 cells have been shown to have a maximum secretion at 3 mM with a half-maximum at 0.5 mM glucose loads. For both the control and PBM-treated groups, the samples were washed in Krebs Ringer Buffer (KRB) at 0 mM glucose for 1 hour, and then mounted onto the chamber. Following laser irradiation, the samples were allowed to secrete for 15 minutes. The samples exposed to PBM in a 0.5 mM glucose solution demonstrated a 30% increase in insulin secreted over the control samples. PBM exposure of cells in a 3 mM solution also appeared to increase insulin secretion by ~70% over the control group. However, the amount of secreted insulin was not found to be significantly different than that measured among the 3 mM control group (p>0.05). (FIG. 13)

Discussion

It was clear from the results that 810 nm PBM was capable of stimulating the calcium dynamics in βTC-6 cells, as the calcium spiking frequency and the active proportion of the population was increased. This response is similar to what is found in glucose-stimulated insulin secretion (GSIS) in that both the frequency increased along with the number of cells actively spiking. In GSIS, this response is due to an increased rate of depolarization events caused by ATP-sensitive potassium channels in the cell membrane. Membrane depolarization can open the VGCCs allowing a calcium influx, which influences the rate of calcium spiking events. However, the mechanisms by which PBM modulates the calcium dynamics in β-cells are yet to be fully elucidated.

Much of the work performed by the Hamblin group, has demonstrated that NIR-PBM likely affects intracellular calcium via activation and opening of TRPV channels. In this mechanism, light is absorbed by structured water surrounding the channels, heating it and opening the channels. While the TRPV channels allow for calcium influx, other cations such as sodium and potassium are also able to proceed down their electrochemical gradients resulting in membrane depolarization. Since the calcium currents for TRPV channels is relatively low, it is more likely that the depolarization by TRPV channels leads to the activation of VGCCs resulting in much stronger calcium currents. Capsazepine is stated to be membrane impermeable, indicating the TRPV1 channels at the cell surface are one of the targets that responds to PBM. Thus, the findings here indicate that the activation of TRPV1 channels at the surface is involved in the early stage of calcium spiking than other TRP channels that are expressed on the endoplasmic reticulum. Overall, these results support the model that both membrane surface TRPV1 and L-type VGCC channels mediate the response of modulating calcium dynamics by PBM.

It was demonstrated that very short pulses of NIR light were able to bring about calcium spikes in cardiomyocytes. In this work, blocking the Ryanodine receptors that generally control calcium induced calcium release (CICR) did not significantly affect the calcium spiking frequency but did reduce the amplitude. In addition, $IP_3$-receptor blocking by 2-APB appeared to disrupt calcium spiking. It was also shown that 2-APB inhibits the PBM-induced calcium dynamics in glioblastoma cells. PBM is able to stimulate the phospholipase $C/IP_3$ pathway that regulates CICR by involving intracellular calcium stores. The results show that Ryanodine receptor blocking does diminish but not abolish the calcium spiking in response to PBM. However, the $IP_3$-receptor pathway appears critical in the overall stimulation of calcium spiking (see FIG. 10).

The results from the present study help clarify the mechanisms in which PBM affects the calcium response. With respect to the metabolic mechanism(s), it has been shown that NO plays an inhibitory role in the energy production of the mitochondria. Higher concentrations of NO lead to an increase in reversible binding to CCO, thus slowing its binding to $O_2$ and leading to a reduced flux in the electron transport chain (ETC). When laser photons are absorbed by CCO, NO is dissociated from CCO and increases its $O_2$ consumption. This allows for an increase in flux through the ETC, corresponding with an increase in ATP and ROS production. The results herein demonstrated an increase in intensity from both MitoSOX ($O^-_2$) and DAF-FM (NO) indicating elevations in available superoxide and nitric oxide, respectively. While the calcium channels can be responsible for the initial stage of calcium influx across the cell membrane, an elevation in mROS is postulated to contribute to and sustain the increased calcium dynamics beyond the initial stimulation induced by PBM through activation of TRP channels in endoplasmic recticulum, $IP_3$- and Ryanodine-receptors.

Intracellular concentrations of ROS can be both therapeutic and pathological depending on the concentration and the amount of time present. For instance, chronic glucose load brought about by insulin resistance is well known to cause β-cell oxidative stress via ROS production that leads to the cell's dysfunction and apoptosis. Alternatively, mROS production has been shown to help stimulate the release on insulin, and therefore acting as a signal of glucose load in β-cells. ROS formation can induce calcium spiking along with insulin secretion in β-cells via endoplasmic calcium release. The results herein demonstrate that the antioxidant AA is able to suppress the superoxide concentration, which inhibits the calcium spiking frequency at later time points. (see FIGS. 12A-12B) Localized water heating around TRPV1 channels initially activates the channels with subsequent VGCC activation via membrane depolarization. Moreover, a metabolic shift that increases the intracellular ROS levels acts to sustain the calcium spiking activity in response to PBM via ROS-mediated activation of Ryanodine- and IP3-receptor and TRPV channels.

Finally, based on these changes to calcium dynamics in β-cells, 810 nm PBM was used to modulate insulin secretion. The results herein demonstrated an increase in insulin secretion in response to PBM at a lower glucose load. (see FIG. 13) While PBM exposure substantially increased the insulin secretion at a higher glucose load, it was not statistically significant. The number of combinatory PBM parameters can exponentially grow if one considers dependence on the wavelength, fluence and also the rate of energy deposit.

Figure 14:
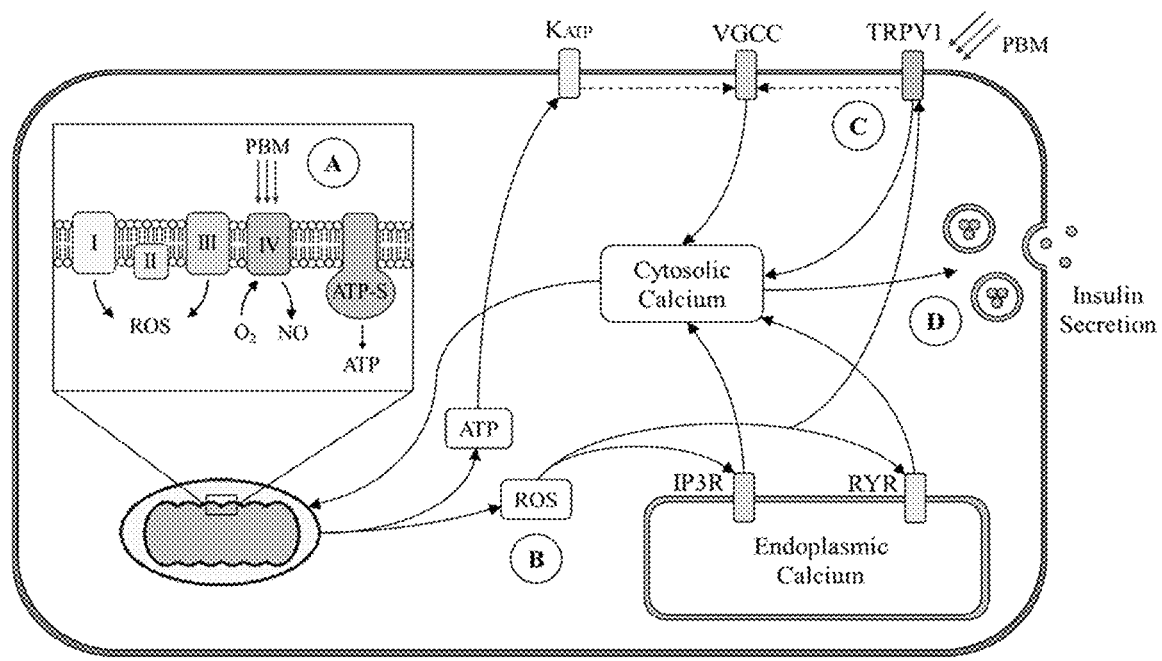
FIG. 14 shows schematic of working model. Inset A shows that PBM activates TRPV1 channels at the cell membrane that leads to membrane depolarization and opening for voltage-operated calcium channels. Point B shows that PBM dissociates NO from CCO that increases $O_2$ consumption and flux through the ETC. This results in an increase in mROS and likely ATP. Point C shows while the metabolic changes may further contribute to membrane depolarization via the canonical pathway, ROS is involved in the activation of IP3 receptors, Ryanodine receptors, or endoplasmic TRPV channels. Point D shows that collectively, the resulting increase in calcium spiking activity alongside the metabolic shift is presumed to induce insulin secretion by the β-cells. In the context of a short 15-minute observation period of time, exocytosis of the pre-packaged insulin in vesicles rather than translation is more likely.

This study here demonstrates that PBM can stimulate the calcium spiking frequency and activity in β-cells. A working model is shown that incorporates several mechanisms. (FIG. 14) PBM is postulated to activate TRPV1 channels at the cell surface and mediate ion fluxes across the cell membrane. Changes in the ion concentrations can lead to membrane depolarization and activate electrically operating channels such as L-type VGCCs. Combined effects of TRVP1 channel and VGCC activation initiate and enhance calcium spiking. In tandem, PBM couples to COO and increases intracellular mROS that can potentially release calcium from intracellular calcium stores primarily through the $IP_3$-receptor pathway. Such an elevation in mROS can sustain and extend the calcium spiking response beyond the initial stage. Taken collectively, these events lead to insulin secretion and support the ability of NIR PBM to alter both the calcium and insulin dynamics in β-cells with therapeutic applications to promote the functionality of islets. Finally, the laser exposure apparatus employed in the current study was designed to determine and elucidate coupling mechanisms in a short 15-minute observation time window. Increases in the insulin secretion under two glucose loadings can be interpreted as facilitated exocytosis of the pre-packaged vesicles rather than translational synthesis of insulin. Additional apparatuses are created to expose β-cells to PBM for a longer period of time (e.g., 9 $J/cm^2$ per day over several days).

Example 3. An Integrated Model for Predicting the Functional Effects of Electrical and Photonic Stimuli on β-Cells Introduction It has been well established that cells are able to sense and respond to their local environment, with insulin secreting β-cells being no exception. While many efforts have focused on the biologic environment, few reports have demonstrated how these cells may respond to various physical stimuli. Previous research has demonstrated that cellular functionality can be altered by physical stimuli such as electrical fields and laser therapy. Electric fields are natively found in several biological processes from wound healing to neural signaling, while cellular responses to light are commonplace in the eye and skin. Depending on the parameters, exogenous EFS and PBM have demonstrated therapeutic potential by altering various aspects of cellular physiology.

EFS has been used to improve wound healing alongside therapies such as deep brain stimulation. EFS affects the polarity of the cellular membrane leading to changes with the cell's electrophysiology with respect to depolarization event timing and cation flux. At biologically relevant electric field (EF) strengths (~1-5 V/cm), a slow increase in calcium entry has been demonstrated and is mediated by the opening of voltage gated calcium channels (VGCCs). When the EF strengths are orders of magnitude higher, electroporation can occur with applications for transfection and instigating cellular death. While the study here focuses on direct current (DC) EFs given their biologic mimicry, many other groups have demonstrated therapeutic benefits with pulsed DC- and alternating current (AC-) EFs. While biologically relevant DC-EFs only affect the cellular membrane's polarity, pulsed and AC EFs are capable of affecting intracellular physiology, thus increasing the complexity of the cellular response.

While the mechanisms of EFS are relatively well established, the mechanisms for PBM have yet to be fully elucidated. Some of the leading mechanisms of PBM include the activation of TRP channels, dissociation of nitric oxide (NO) from the functional heme binding site on cytochrome C oxidase (CCO) leading to an increase in electron transport chain (ETC) flux, and release of calcium from the endoplasmic reticulum via IP3- or Ryanodine-receptor channels. Regardless of the mechanisms, PBM has demonstrated the ability to increase various intracellular signaling molecules such as calcium, reactive oxygen species (ROS) including superoxide and NO, and metabolic signals such as the ATP/ADP ratio.

Of particular interest here, previous work has demonstrated electrophysiological and insulin secretory changes in the β-cell phenotype by EFS and PBM exposure. To explore the effects of these stimuli along with any synergistic or antagonistic responses, an integrated numerical model was developed to simulate calcium and insulin responses to these modalities independently and in combination. By elucidating these interactions, these modalities are be able to stimulate β-cell insulin secretion for use in various therapeutic applications.

Methods

Figure 15:
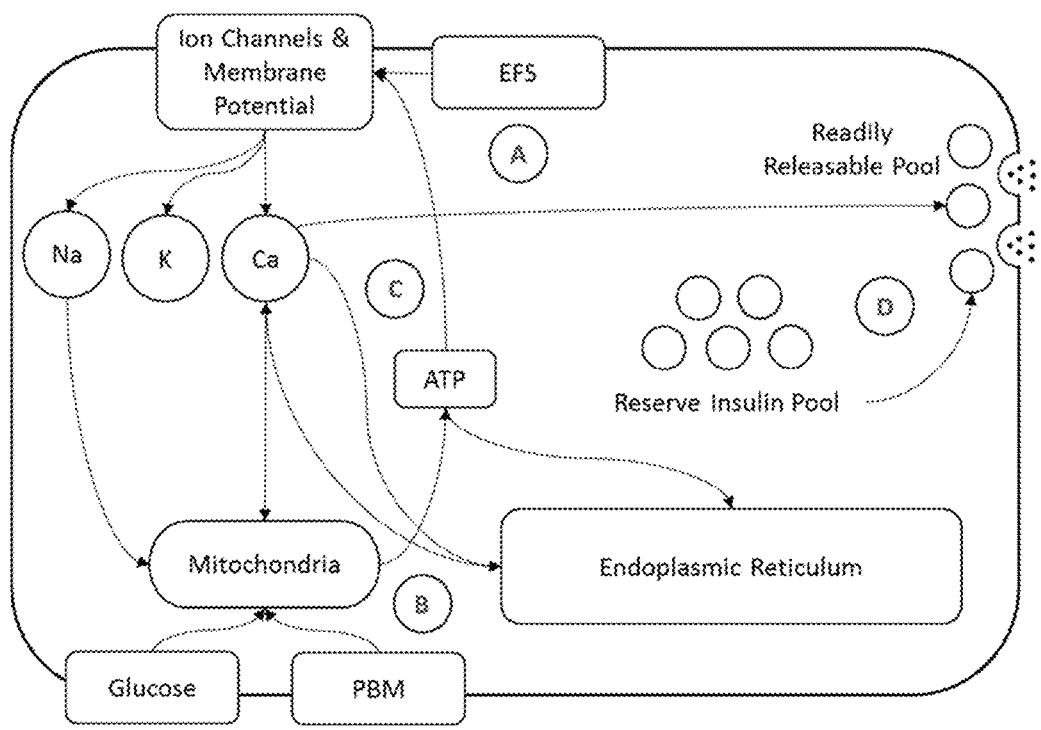
FIG. 15 shows that EFS (Point A) is capable of altering the membrane potential and thus affection cationic currents into the cell. Point B shows that PBM exerts its effects on CCO activity increasing ETC flux and ATP production. Point C shows that, due to interactions between EFS and PBM, the calcium dynamics are altered within the cell. Point D shows that these calcium dynamics directly spur insulin secretion from the readily releasable pool followed by replenishment from the reserve insulin pool.

Modeling and Simulation: The electrophysiological model was replicated in Matlab from the 2003 Fridlyand model for β-cell calcium dynamics. The ATP production in this model was then replaced with the output of the 2010 Fridlyand model for a β-cell's mitochondrial function. These two models were then integrated with a previously developed model of insulin secretion. Some modifications were made to the insulin secretion model to account for maximal secretion rates and maximum refilling rates for readily releasable pools based on a previous report. In addition, the oxygen acceptor kinetic factor (FAe) of was set to 0.6 from 1.0 to account for an assumed NO inhibition (50 nM) of CCO activity and thus an inhibited capacity for ETC flux and oxygen consumption. An illustration of the overall model's components can be found in FIG. 15.

Electrical stimulation was modeled using the equation for membrane potential by external electric fields by Schoenbach. Given the hyper- and hypo-polarization between the anode and cathode facing sides respectively, the hyperpolarized side was neglected, while the depolarized side was accounted for by assuming the average depolarization to be the average value from $-\pi/2$ to $\pi/2$, resulting in a multiplier of $2/\pi$. The averaged membrane potential then becomes $1/\pi$ of the maximal value when halved considering only the depolarized side. Thus the change in membrane voltage and its differential equation become:

$$V_m = \frac{1}{\pi} f_c E r$$

$$\frac{dV_m}{dt} = \frac{\Sigma I_m}{-C_m} + \frac{1}{\pi} f_c E r$$

Where $V_m$ is membrane voltage, $f_c$ (1.5) is the spherical form factor, E is electric field strength, and r is the cellular radius with 7 μm used for β-cells. The $I_m$ are the plasma membrane currents with $C_m$ being the overall membrane conductance.

Given that the exact mechanisms of photobiomodulation aren't fully elucidated, various potential mechanism was firstly incorporated into the model and varied their parameters to observe how the calcium dynamics can be affected. Since TRPV antagonist such as Capsazepine have demonstrated the role of TRPV1 in PBM's effects on calcium dynamics, this channel was added to the model to investigate its impact by varying its open fraction. The equations for its ionic currents were determined by its previously reported conductance elsewhere.

While TRPV1 can be activated by other factors such as ROS signaling and pH levels, the most well-established dependency is temperature. Using a simple thermal model for a cell along with a cellular convective heat loss estimate found elsewhere, the temperature rise in a cell by light exposure was simulated. This assumed light was absorbed by the cell via its cross-sectional area and with heat loss to the surrounding media via its surface area. Additionally, the temperature of the media was allowed to rise by its absorption via its cross-sectional area with an assumed surface heat convection loss of 50 W/m²K. This was then compared to experimentally determined temperature elevations of the bulk media. The differential equation for the cellular temperature rise is:

$$\frac{dT_{cell}}{dt} = \frac{\alpha\ I_r\ A_c - h_c\ A_{sc}(T_{cell} - T_{med})}{m_c\ C_p}$$

Where α is the absorbance of water at 810 nm, $I_r$ is the irradiant flux, $A_c$ is the cross sectional area for the cell, and $h_c$ was the convective heat loss to the media from the cell $T_{cell}$ and $T_{med}$ are the temperatures for the cell and media respectively, with $m_c$ being the cell's mass, and $C_p$ being the specific heat of water. The temperature change for the media was determined by:

$$\frac{dT_{med}}{dt} = \frac{\alpha\ I_r\ A_m - h_m\ A_{sm}(T_{med} - T_{sur})}{m_{med}\ C_p}$$

Where $A_m$ is the cross sectional area for the media, $h_m$ being the convective heat loss to the surrounding from the media's surface $A_{sm}$, and $m_{med}$ being the media's mass.

The cytosolic calcium influx by PBM has also been shown to originate from intracellular stores, in particular from IP3-Receptors on the ER membrane in some cell types. Since, the electrophysiological model already included equations for the calcium release via these channels, its calcium flux was multiplied by a factor to determine how a potential increase of the open fraction from the IP3-receptor channels contributes to the overall calcium dynamics.

For the activity of CCO by PBM, the integrated mitochondrial model includes an equation for proton pumping related to ETC flux:

$$J_{hres} = V_{me} F_{De} F_{Ae} F_{Te}$$

Where $V_{me}$ is the optimal rate of proton flux with, $F_{De}$ accounting for NADH availability, $F_{Te}$ accounting for mitochondrial membrane potential, and the modified $F_{Ae}$ oxygen availability for binding to CCO completing ETC flux. While the original model kept $F_{Ae}$ at maximum ($F_{Ae}=1$), this parameter in the model was varied from 0.6 to 1 to see how the availability of oxygen binding to CCO affects the calcium dynamics. Thus demonstrating the effect of PBM on CCO's activity into the model.

Based on these results, PBM was modeled by its fluence through a combination of these parameters to match experimentally observed data. CCO activity was estimated by a $2^{nd}$ order polynomial fitted to experimentally estimated CCO activity by fluence at 660 nm from a previous report. We then accounted for the difference between 660 nm and 810 nm by their respective CCO absorbance. Thus the multiplier for CCO was determined by the following:

$$\Delta FAe = 1 + 1.6[\alpha_{CCO}I_r] - 0.9[\alpha_{CCO}I_r]^2$$

With FAe being 0.6 multiplied by this change in CCO activity by PBM.

While CCO appeared to be the dominant factor affecting the calcium spiking, it did not adequately account for the observed rise in spiking frequency. Thus, PBM can be modulating Glucokinase activity (GKA) and thereby increasing the rate limiting factor for glucose consumption Small variations in Glucokinase (GK) capacity were able to substantially affect the calcium dynamics. To better match the data, a multiplier of $1 + FAe(\Delta FAe - 1)/14$ was added to the model with a maximum increase of 5% in GKA at peak PBM values.

Simulation Plots: Results from the model were generated over a range of parameter values, with the results being subtracted from the control values. These difference values were then color coded with green represented a reduction from the control and red representing an increase, with black being no change. A box mean blur was then performed to attempt an interpolation between the given simulations. The color intensity was adjusted between the negative and positive values for the absolute maximum value from the data.

Bulk Temperature Experimentation: Using an Omega HH42A thermistor, bulk temperature measurements were taken of the HBSS before and after the 1 minute exposure to PBM with the fluences 4.5, 9.0, and 18.0 J/cm². The total volume of Hank's balanced salt solution (HBSS) in the chamber was 2 mL, which was the same as the sample runs. All fluences incorporated 6 experimental runs with initial temperature readings as similar as possible.

Cell Culture: Mouse insulinoma β-TC6 cells from ATCC were grown in high glucose (4.5 g/L) Dulbecco's modified eagle's medium (DMEM) from sigma and supplemented with 15% fetal bovine serum (FBS) from Gibco and 1% penicillin-sterptomyosin (P-S) from Sigma. Cultures were incubated at a humid 37° C. with 5% $CO_2$. Samples were prepared using 0.25% Trypsin-EDTA solution from Sigma and seeded on glass coverslips at a density of 40,000 cells per cm² in low glucose (1 g/L) DMEM supplemented with 15% FBS and 1% P-S. Samples were then used within 2-4 days after seeding.

Sample Staining: Half an hour before imaging, samples were washed with HBSS from Sigma and then incubated for 30 minutes with a staining solution containing 0.8 μM Fluo-8 (Abcam) and 1 drop/mL Nucblue (Thermo). Samples were then washed and mounted to the PBM chamber immersed in HBSS. Samples from the PBM groups included Mitosox (μM) for the superoxide measurements in the previous reports.

Fluorescent Imaging: Baseline calcium spiking was measured using a 2 minute video before PBM/EFS exposure and then at 5, 10, and 15 minutes for PBM and just at 15 for EFS. Static images for calcium rise and nuclear position were taken at the baseline and these time points as well. For EFS imaging, the samples were mounted to the chamber as previously described elsewhere and imaged. While for PBM, samples were first imaged, then moved for PBM exposure, and followed by replacement and imaging of the same cells. Details on the PBM chamber and the experimental procedure can also be found in the Example 2.

Image Analysis: Samples from previous works were reanalyzed for comparison with the model's predictions. Regions of interest (ROI) were made on the location of cellular nuclei and then overlaid on the calcium spiking videos to measure the mean intensity of Fluo-8 per cell over time. Using a spike threshold of 10% above the moving average mean (n=10), spikes per cell were recorded with time and used to determine the average frequency of active cells demonstrating at least one spike. Calcium rise was determined by generating ROIs on the cell clusters and measuring the mean calcium at each time point. PBM calcium rise results used the peak intensity over the baseline for the relative values. EFS calcium rise was simply post- over pre-exposure intensities.

Insulin Secretion and Measurement: Experimental samples from the previous reports were used and reported as the relative increase in insulin secretion from their respective controls. Samples were first washed in Krebs Ringer Buffer (KRB) without glucose and incubated for an hour. Samples were then mounted to their respective chambers in KRB. Fifteen minutes after exposure to either PBM or EFS, the surrounding KRB was taken and eventually measured in an insulin ELISA. Normalization was performed using a Cyquant assay to measure DNA content to adjust for the number of cells per sample.

Statistical Analysis: Simple student's paired t-tests were performed between the time points following stimulation with a significant p-value cutoff at 0.05.

Results

Figures 16A, 16B, 16C, 16D, 16E:
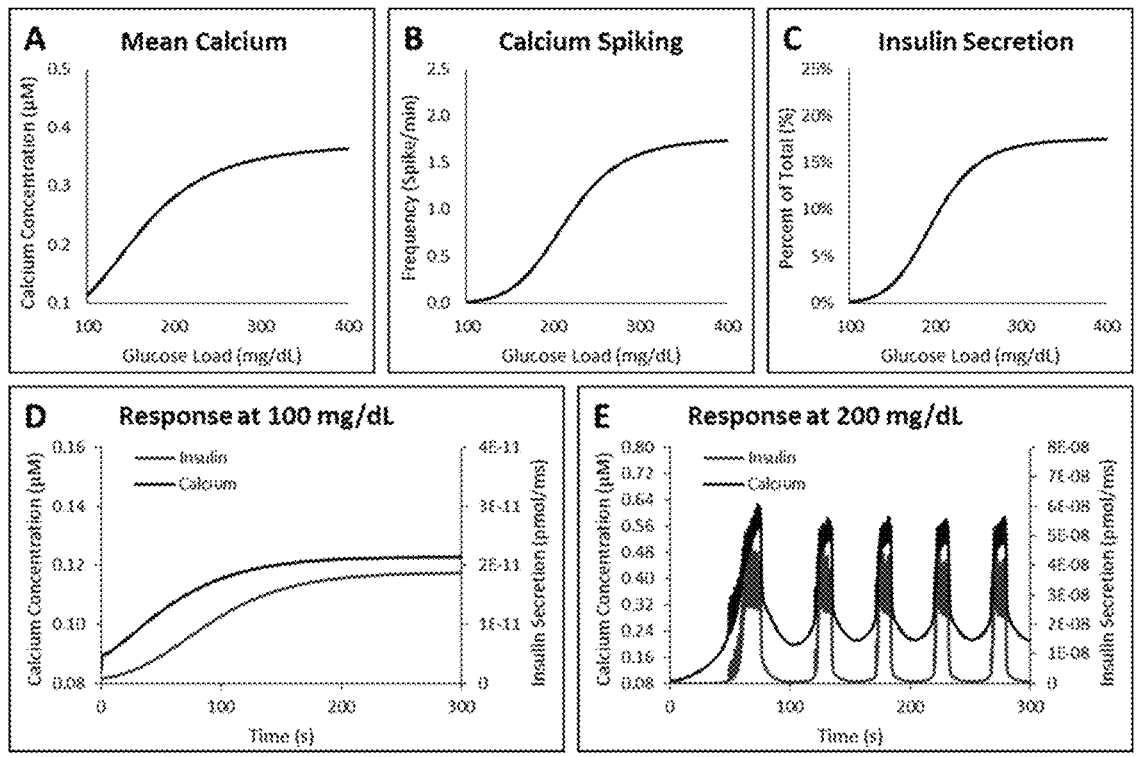
FIG. 16A shows simulated mean calcium at various levels of glucose load.
FIG. 16B shows simulated calcium spiking rates versus glucose load.
FIG. 16C shows insulin secretion as a measure of % of total insulin content by glucose load.
FIG. 16D shows temporal response of calcium and insulin secretion at normal glucose levels (100 mg/dL).
FIG. 16E shows temporal response of calcium and insulin secretion at elevated glucose levels (200 mg/dL).

Model Baseline Response: To determine the model's response to normal stimuli, the simulation results were run for mean intracellular calcium, the calcium spiking frequency, and the percent of total insulin for variations in glucose load. As can be seen in FIG. 16A-16C, the mean calcium, spiking frequency, and insulin secretion all respond appropriately to the glucose load. The rise in calcium spiking and insulin secretion begin to accelerate as the glucose loads increased is critical to normal β-cell physiology. To demonstrate the temporal characteristics of the simulation, response curves for calcium and insulin secretion are shown in FIGS. 16D-16E. At 100 mg/dL, no calcium spiking is observed, mean intracellular calcium is in a steady state, and insulin secretion is low. When the glucose load is increased to 200 mg/dL, calcium spiking begins and is tightly correlated with insulin secretion, with the overall insulin secretion being orders of magnitude higher than the low glucose condition.

EFS versus Glucose Load: Simulation plots were generated crossing glucose load against EFS strength to determine how EFS alone affects the mean calcium, calcium spiking frequency, and insulin secretion, referred to from here on as the standard responses. These plots can be seen in FIGS. 17A-17C. Mean calcium appears to follow a positive linear relationship between glucose load and EFS strength. These simulations correspond well with the observations seen in FIG. 17D.

Figures 17A, 17B, 17C, 17D, 17E, 17F:
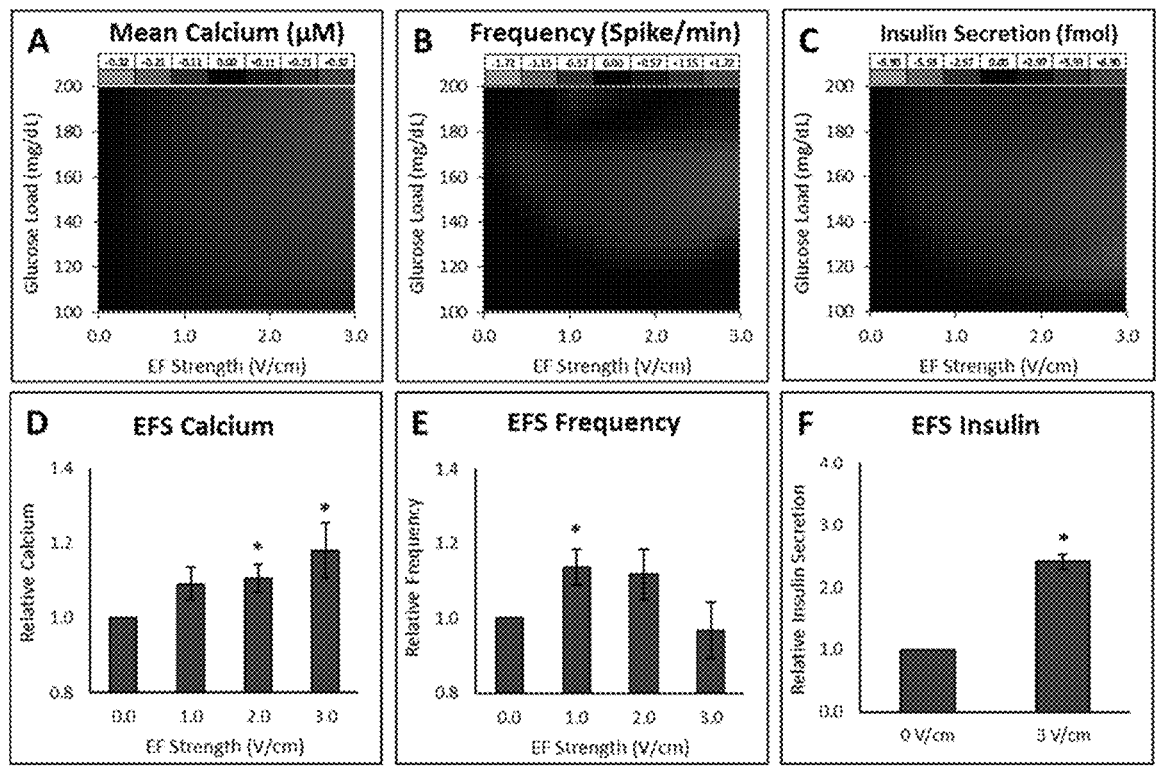
FIGS. 17A-17C show heat maps for the difference (positive=Red, negative=Green) between simulation results and baseline values for mean calcium, spiking frequency, and insulin secretion against glucose load versus electric field strengths.
FIG. 17D shows experimental results demonstrating a rise in intracellular calcium versus EFS strength.
FIG. 17E shows experimentally determined changes in spiking frequency under different EFS strengths.
FIG. 17F shows relative insulin secretion between control group and a 3 V/cm field without glucose.

The relationship between glucose load and EF strength on calcium spiking is more complex. Firstly, EFS can start calcium spiking at lower than basal glucose loads by its depolarizing effects. This phenomenon was previously reported by which the percent of active cells can be increased by EFS. Depending on the glucose load, the rise in calcium spiking occurs between particular EFS values. This type of pattern explains the observations made where calcium spiking was found to increase at 1 and 2 V/cm but then begin to decrease at 3 V/cm as seen in FIG. 17E. Another observation is that the simulation predicts a slight decrease in calcium spiking at higher glucose loads.

The relationship between EFS and glucose load on insulin secretion appears to be relatively straightforward. Given that calcium dynamics drive insulin secretion, it seems reasonable that higher glucose loads and greater EF strengths increase the overall insulin secretion rate. A note is to be made that the difference plot demonstrated a greater increase in insulin secretion at low glucose with higher EF strengths. Simulations within these regions predicted the ability of stronger EFs to induce a few calcium spikes but greatly elevate the background calcium concentration. Thus leading to a bursting effect of insulin secretion but without sustained calcium spiking events.

Figures 18A, 18B:
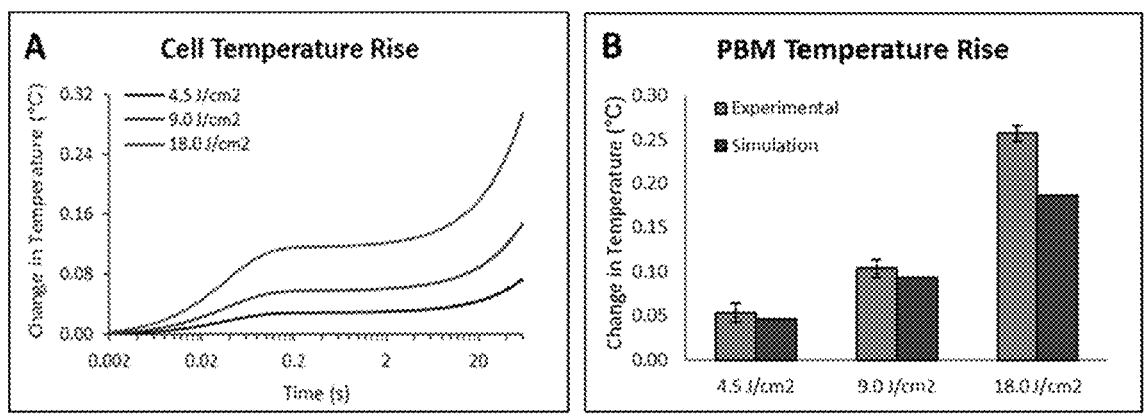
FIG. 18A shows thermal model predictions for the change in cellular temperature over log(time). Within 200 ms the cellular temperature matches the extracellular temperature and rises proportionally with it.
FIG. 18B shows experimentally measured bulk temperature change following 1 minute of laser exposure at various fluences versus the model predictions.

Temperature and TRPV1 Simulations: Given that TRPV1's primary activators are vanilloids and temperature, the temperature rise of a given cell and environment were estimated by the 810 nm laser at various strengths. It appeared that the cell's temperature can rise quickly, but can reach its steady state with the surrounding media within ~200 ms of PBM irradiation as seen in FIG. 18A. After this, the cell's temperature gradually rose as the temperature of the surrounding fluid increased. The model predicted a final temperature rise of 0.046, 0.093, and 0.187° C. for 4.5, 9.0, and 18.0 J/cm$^2$ respectively. While the cell's change in temperature was approximately 162% of the bulk temperature in these simulation, this is negligible with respect to TRPV1 activation give that the cell's max temperatures can be 37.08, 37.15, and 37.30° C. for 4.5, 9.0, and 18.0 J/cm$^2$ respectively. The measured bulk temperatures following PBM exposure seen in FIG. 18B, match well with the predicted values from the model. Assuming a 37° C. initial temperature, the temperature following 300 mW/cm$^2$ for a 1 minute exposure (18.0 J/cm$^2$) is predicted to be 37.3° C. leading to a change in TPRV1 open fraction from 0.0026 to 0.0033 using an equation from another report.

Figures 19A, 19B, 19C, 19D, 19E, 19F:
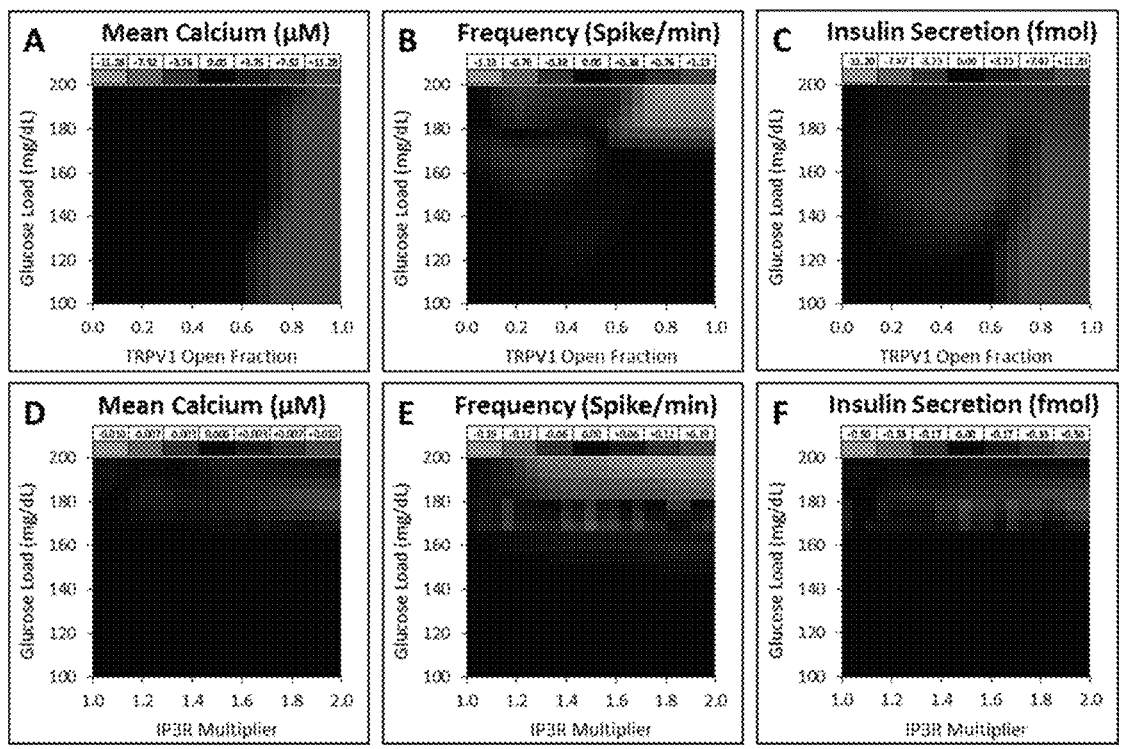
FIGS. 19A-19C show simulation plots for the difference in mean calcium, spiking frequency, and insulin secretion against glucose load versus TRPV1 open fraction.
FIGS. 19D-19F show simulation plots for the differences in mean calcium, spiking, and insulin secretion against glucose load versus an IP3R multiplier.

Nevertheless, an ionic current for TRPV1 was added to the model along with its cationic conductance values obtained elsewhere. The open fraction was then compared to the standard responses. Mean calcium was slightly increased at all open fractions, but when the open fraction was approximately greater than 0.7, the cell can be flooded with intracellular calcium as seen in FIG. 19A. TRPV1 was found to modestly increase spiking frequency at medium glucose loads between 0.0 and 0.4 open fractions, while at higher glucose loads or greater open fractions it can reduce the spiking frequency as seen in FIG. 19B. In FIG. 19C, insulin secretion can be increased at medium glucose loads with lower open fractions due to the small increases in calcium spiking and intracellular calcium. At high open fractions, the flooding of intracellular calcium leads to an insulin burst, with the maximal insulin secretion rate being reached.

IP3-Receptor Activation: The simulation plots were made for the standard responses with IP3R being sensitized up to a 2-fold increase in its calcium flux FIGS. 20A-20C. As for the mean calcium, increasing the sensitivity to opening lead to an increase in intracellular calcium. The increase in calcium was at most 0.01 μM equating to about a 3% rise from basal. Spiking frequency appeared to increase when sensitized for lower glucose loads, which was due to activation of spiking near the glucose load threshold rather than a true increase in spiking frequency, while higher glucose loads decreased the change in frequency. As with the calcium, the difference between the sensitized channel and the basal response was low, increasing at most by 0.18 spikes/min. Finally, the change in insulin followed the same trend as the change in the mean intracellular calcium. As the receptors were sensitized, insulin secretion increases, yet to a relatively small difference between it and the basal response.

Figures 20A, 20B, 20C, 20D, 20E, 20F:
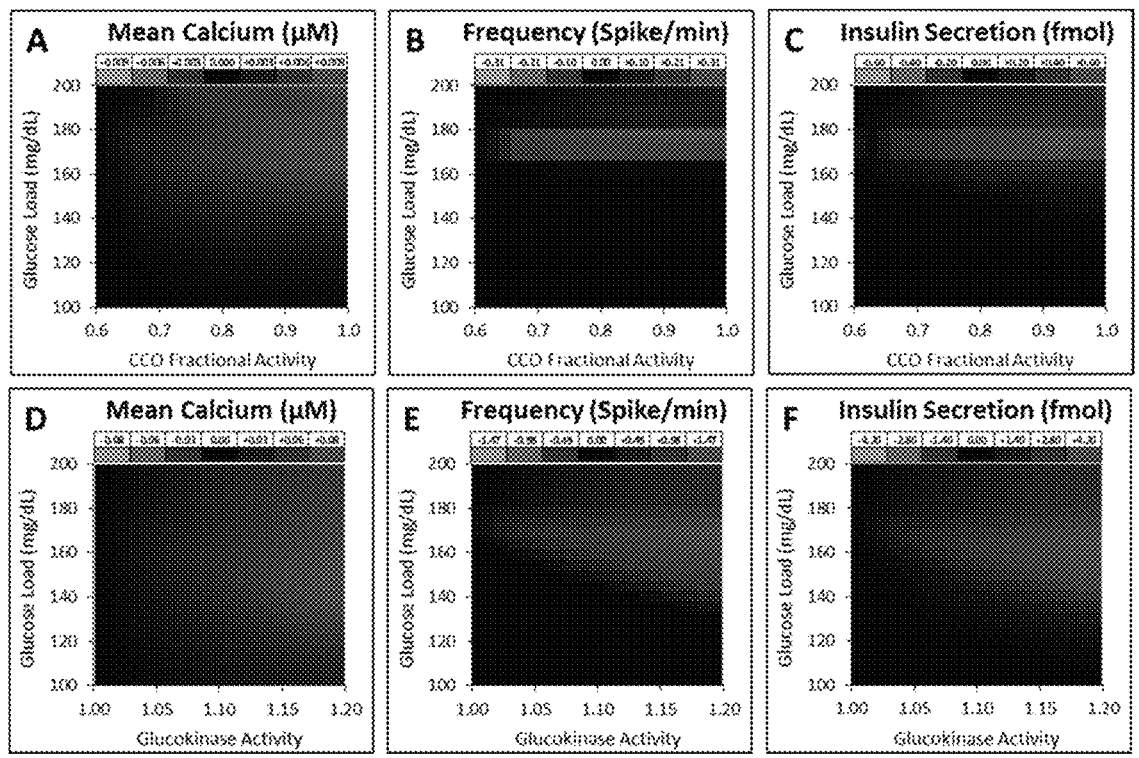
FIGS. 20A-20C show simulation plots for the difference in calcium, spiking, and insulin secretion against CCO fractional activity.
FIGS. 20D-20F show simulation plots for the difference in calcium, spiking, and insulin secretion against glucose load versus fractional glucokinase activity.

CCO Activity: The primary mechanism by which PBM affects the cell is through CCO activation by dissociating NO from its functional heme group. Given that the estimated activity for the model at basal conditions was set to approximately 60% (FAe=0.6), PBM can increase this value up to its optimal conditions near 100%. As explained in the methods section, the increase in Fae was estimated based on a previous report with PBM and CCO activity. Since the basal conditions were set at 0.6, a reduction from this activity thus inhibited the standard responses. When CCO activity is increased as seen in FIGS. 20A-20C, both insulin secretion and calcium spiking is modestly increased. Similar to results from the IP3-Receptor simulations, the activation of calcium spiking is near the threshold value for glucose. Unlike IP3-receptor simulations, increases in CCO activity do not inhibit spiking or insulin at any glucose load and had a greater increase in calcium spiking.

Glucokinase Activity Simulation: Under the assumption that PBM can increase the activity of GK, the sensitivity of the cell to its glucose load can be increased. The standard responses were modeled by a multiplier of GK from 1 to 1.2 seen in FIGS. 20D-20F. While the increase in the mean calcium was small, the spiking frequency can be greatly increased by GKA. The increase in its activity can also lead to the activation of calcium spiking at lower than basal threshold levels. This strong increase in calcium dynamics was able to increase the insulin secretion beyond the basic rise in background calcium.

PBM Model for Stimulation: Given the results from TRPV1, IP3R, CCO, and GK stimulation, the dominant factors that resulted in the spiking rise observed can be the stimulation of CCO and GKA. TRPV1 was excluded from the PBM model since the thermal rise was far too small to lead to significant opening of these channels. Beyond this, both TRPV1 and IP3-Receptor activation within the model did not result in the large rise in calcium spiking observed with experimentation. The standard responses were plotted shown in FIGS. 21A-21C. While the effects of PBM demonstrate an increase in intracellular calcium, the change was much less than the simulated effects of EFS. For calcium spiking, the greatest increase appeared near the glucose threshold, indicating an activation of the calcium dynamics when at basal conditions spiking cannot occur. Insulin secretion demonstrated peaks with calcium spiking rather than elevations in intracellular calcium.

Figures 21A, 21B, 21C, 21D, 21E, 21F:
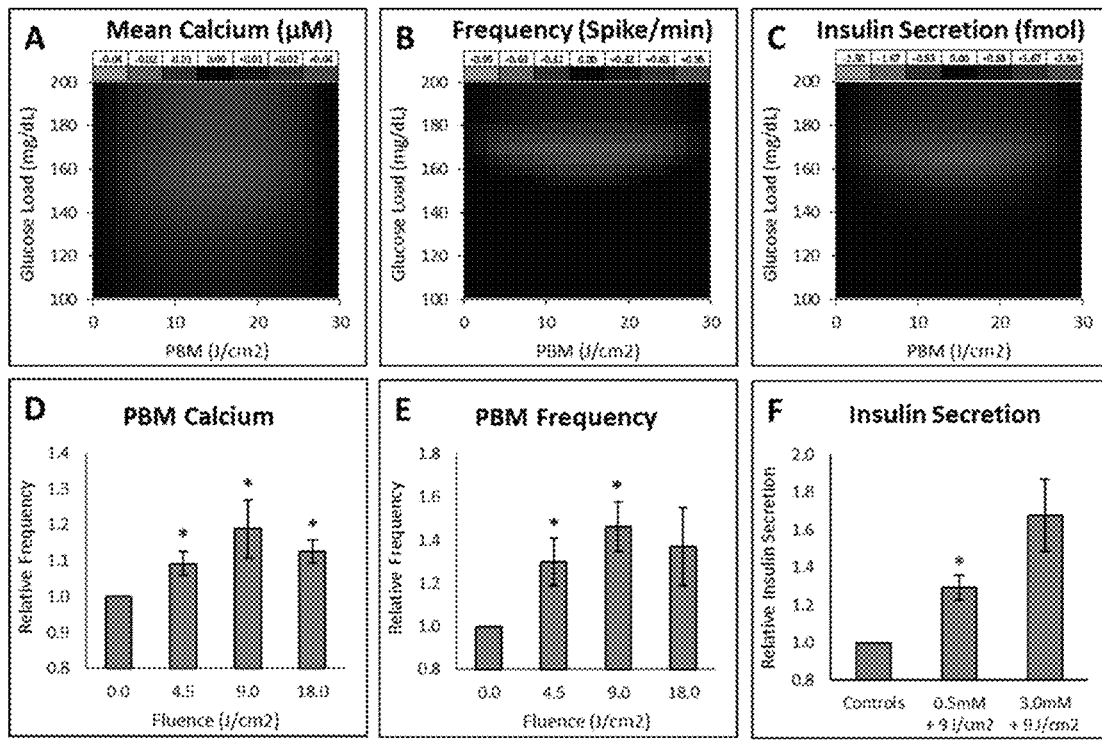
FIGS. 21A-21C show simulation plots for the difference in mean calcium, spiking, and insulin secretion against glucose load versus PBM fluence based on CCO and GK activation.
FIG. 21D shows experimentally derived relative changes in mean calcium following PBM irradiation at various fluences.
FIG. 21E shows relative change in frequency following PBM exposure.
FIG. 21F shows percent total insulin secretion following 9 J/cm2 PBM exposure at 0.5 and 3.0 mM glucose loads.

The simulations demonstrated similar patterns to the data presented in FIGS. 21D-21F. The mean calcium along with spiking frequency increased with fluence and then began to decrease at higher strengths. While the simulations demonstrate an optimal range between 10-20 J/cm$^2$, the data show that the peak may be closer to 10 J/cm$^2$ with a narrower range. This can be due to differences between how isolated mitochondria and intracellular mitochondria respond to PBM. The experimental results for insulin secretion were increased following PBM exposure and demonstrated the influence of glucose load with PBM.

EFS with PBM: Finally, in an attempt to determine interactions on the cellular response between EFS and PBM, multiple plots were generated and shown in FIGS. 22A-22C. Both mean calcium and insulin secretion were maximized when the simulation's optimal fluence (15 J/cm$^2$) and greatest EF strength (3 V/cm) were applied. All of these plots were generated at a glucose load of 180 mg/dL since this is the threshold for spiking to begin. The plot for calcium spiking frequency was the most diverse, with a section around 1 V/cm and the PBM window having the lowest increase in spiking. Also worth noting, the calcium spiking was greatest within the PBM window at low EF strengths, but was the least at higher EF strengths.

Figures 22A, 22B, 22C, 22D, 22E:
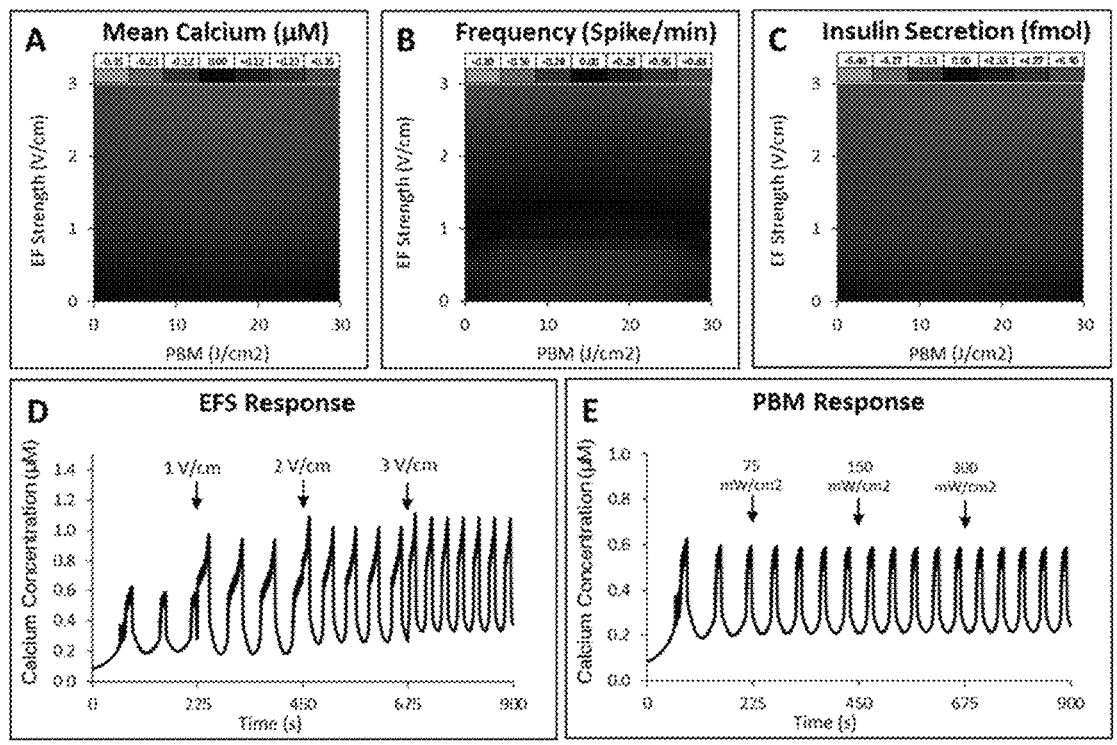
FIGS. 22A-22C show simulation plots for the difference in mean calcium, spiking, and insulin secretion with EFS strengths versus PBM fluence at 180 mg/dL demonstrating potentially optimal therapeutic windows for synergistic cooperation.
FIG. 22D shows temporal plots of calcium and insulin secretion for 180 mg/dL, with sequential increases in EF strength demonstrating the change in calcium waveforms and frequency.
FIG. 22E shows temporal plot for intracellular calcium at 180 mg/dL, with sequential increases in PBM irradiance demonstrating the change in frequency derived by PBM's effects.

To observe the temporal responses to these stimuli, FIGS. 22D-22E plotted the calcium response to sequentially increasing EFS and PBM stimulations respectively. EFS caused an increase in frequency with greater EF strengths, but also increased the amplitude and reduced the spike duration as the EF's strengths increased. Similar to EFS, PBM was able to increase spiking frequency at higher fluences, but unlike the EFS response the spikes' morphologies and amplitudes appeared unchanged.

Discussion

EFS exerts the majority of its effects by altering the membrane potential leading to an increase in the open fraction of any voltage dependent channels. The previous report demonstrating the involvement of VGCCs in EFS instigated calcium influx indicates that it is the dominant driver, yet several other cationic channels present in β-cells can also be affected. While this can explain the influx of intracellular calcium from the extracellular space, it does not account for the change in the spiking frequency. Therapies utilizing EFs with neurological processes have demonstrated that fields as weak as 0.05 V/cm can affect the depolarization events of neuronal cell. It seems that the small shift in membrane polarity is able to reduce the delay between depolarization events by increasing the voltage driving force for the ionic currents. This increase in the depolarization frequency can lead to shorter and more frequent calcium spikes, given their dependency on depolarization events.

When investigating the effects of EFS with respect to the model's predictions, it appeared that by increasing the EF strength under a constant glucose load, the frequency continues to rise until a dropping point was reached that depended on the particular glucose load. When applying even greater EF strengths, the model predicted a region where spiking ceases and the cell can be flooded by an influx of calcium. This is due to a driving force inducing calcium influx that surpasses the cell's capacity to sequester or remove calcium from the cytosolic space. This has been well documented with stronger EFs as a method to induce cellular death via calcium cytotoxicity. Another region occurred with glucose loads greater than around 180 mg/dL under constant EF strengths, where the spiking did not increase and even decreased at lower EF strengths. Looking at the temporal plots in this region, it appeared that the duration between each spike was in fact reduced, but because of the increased amplitude of each spike, its width became longer than its period and thus reduced the overall frequency.

The insulin secretion appeared greatest at higher field strengths with a strong increase in calcium spiking, but another area also appeared at lower glucose concentrations with elevated EF strengths. The temporal plots indicated that the calcium influx overwhelmed the cellular machinery to remove calcium from the cytosol given that one large spike occurred followed by a steady elevated level of intracellular calcium which lead to a strong burst of insulin secretion. Since repolarization events and the resting membrane potential require ATP dependent ionic pumps, these outward currents were insufficient to overcome the influx of cations brought about by EFS.

While previous work has demonstrated the involvement of TRPV1 channels with PBM's effects, the lack of temperature rise is unlikely to induce their opening. Other TRPV channels are also be involved since they are able to respond to lower temperature levels. Alternatively, it has been reported that the drug Capsazepine can inhibit VGCCs alongside TRPV1. Since VGCCs are critical to the electrophysiology of β-cells, this inhibition can guise itself as TRPV1 inactivation. PBM can also induce elevations in ROS leading to the activation of TRP channels. Since the peak of calcium spiking commonly occurred around the 10 minute mark following irradiation in the experimentation, this can be a cause; however, the opening of TRPV1 alone does not seem to account for the effects given by the model's predictions.

Previous publications reported that cardiomyocytes can be stimulated to by high intensity pulsed laser to drive calcium spikes. Furthermore, it was indicated that sarcoplasmic release of calcium was the more likely source of cytoplasmic influx. Another report concluded that PBM was able to induce IP3-Receptor calcium release from the endoplasmic reticulum. While IP3-Receptor activation can be induced by PBM exposure, the model did not predict significant changes in the calcium dynamics of these cells. Drugs to inactivate IP3-Receptors can be interfering with oscillatory machinery instead of simply blocking the effects of PBM.

The primarily cited mechanism of action is the stimulation of CCO leading to elevations in ATP, ROS, and NO. Depending on the amount of inhibition by NO on CCO, this mechanism explains some of the findings, yet if there is little NO inhibition to begin with, it wouldn't seem likely to have a great effect. The model here demonstrated an increase in calcium spiking and insulin secretion brought about by a shift in CCO activity, yet the magnitude of the effects was lacking in comparison with the experimental observations. Looking for another explanation, the increased metabolic state of the cell can increase the activity of Glucokinase thereby increasing ATP production. GKA has been shown to be adjusted by the cell within minutes depending on the activity of the GK regulatory proteins. These proteins inactivate and transport GK inside the nucleus at low glucose condition, but when glucose is plentiful, GK can be transported into the cytosol thereby increasing glycolytic flux. GK acts as the rate limiting factor in glucose uptake by β-cells and thus presented as a mediator for the observed effects. Additionally, other groups have demonstrated that cytosolic NO along with calcium release from the endoplasmic reticulum can lead to an increase in GKA. Thus the increase in GKA can be an observed effect of IP3-Receptor release with PBM.

While EFS has a strong ability to affect the electrophysiology of the cell, it is unable to affect many of the intracellular processes. In contrast, PBM appears to directly affect the metabolic state of the cell while also affecting a plethora of other potential chromophores. Since metabolic shifts along with elevations in ROS have been shown to affect insulin dynamics, PBM can also lead to insulin secretion via different mechanisms than EFS. The results from the model indicate that through the combination of EFS and PBM, β-cells can be stimulated to secrete insulin and respond to lower glucose levels as if they were higher glucose concentrations. While at elevated glucose concentrations, EFS and PBM can only induce smaller changes in the cell's immediate response.

Given that calcium dynamics play a major role in controlling the functions of various transcription factors and enzymatic activity, the ability to augment it via non-invasive modalities proves a powerful therapeutic tool, especially for ex vivo or stem cell interventions. Another group has demonstrated beneficial outcomes from the combination laser therapy with magnetic fields to improve mesenchymal stem cell proliferation thus validating the possibility of a synergistic action between these modalities. Low strength EFS can improve insulin secretion similar to the electrophysiologic mechanisms of Sulfonylurea. While multiple PBM exposures have been shown to increase SOD2 expression, and thus can be used as a preventive measure to glucose toxicity and oxidative stress in diabetes.

The results from the model indicate that the optimal parameters depend very much on the desired physiologic outputs and the metabolic state of the cell. At lower glucose levels a combination of increasing the metabolic state by PBM with an amplified insulin secretion by EFS is optimal, while at higher glucose concentrations PBM is not as necessary, as EFS had stronger effects with this regime. The results of this model give insight towards a synergistic methodology utilizing these modalities for use in diabetic therapies.

Example 4. Simulation Flow Chart

Figure 34:
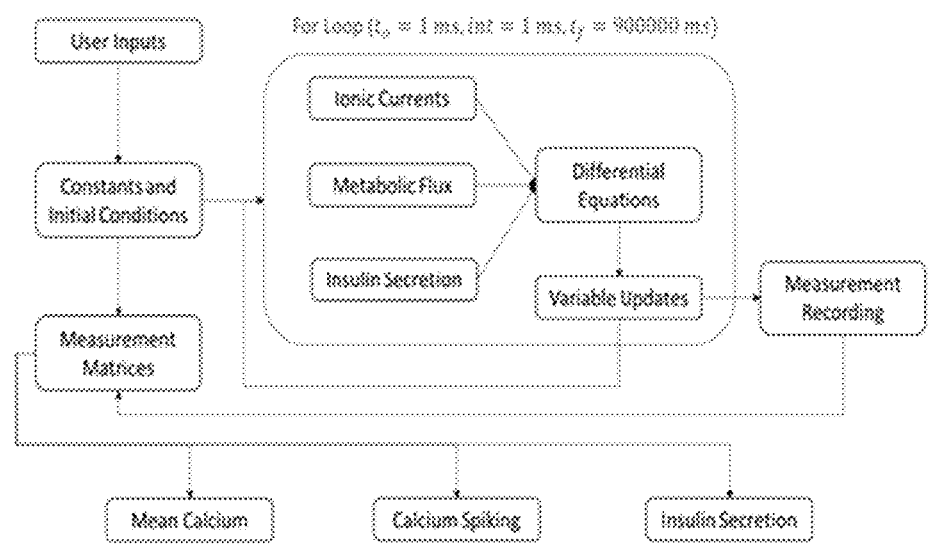
FIG. 34 shows a flowchart for simulations, with user inputs and constants fed into a for loop solving for ionic currents, metabolic fluxes, and insulin secretion. These values are then fed into the differential equations and followed by the variables being updated. Measurements are taken at each time point and used to determine the output results.

All values used the following units: Time (ms), Concentration (μM), Volume (pL), Potential (mV), Current (fA), Capacitance (fF), and Conductance (pS). All simulations were performed on a Dell Latitude E7470 with an Intel i7-6600 with 8 GB of DDR4 RAM using MATLAB Version: 9.2.0.556344 (R2017a). Each run of the full model was timed at 5.17088 (s), the thermal model being 0.013769 (s), and the frequency count code taking 0.005511 (s). Each plot run for the standard parameters would include approximately 441 simulation runs under different parameters, thus taking approximately 38 minutes (FIG. 34).

Example 5. Models and Equations

All of the equations for electrophysiology model (including ion flux equations and differential equations) and parameters were from Fridlyand, L., Tamarina, N. and Philipson, L., 2003. Modeling of Ca2+ flux in pancreatic β-cells: role of the plasma membrane and intracellular stores. *American Journal of Physiology-Endocrinology and Metabolism*, 285 (1), pp. E138-E154, incorporated by reference herein in its entirety.

All of the equations for the metabolic model (including metabolic equations) and parameters were from Fridlyand, L. and Philipson, L., 2010. Glucose sensing in the pancreatic beta cell: a computational systems analysis. *Theoretical Biology and Medical Modelling*, 7(1), incorporated by reference herein in its entirety.

All of the equations for the insulin secretion model and parameters were from Kang, H., Jo, J., Kim, H., Choi, M., Rhee, S., & Koh, D. (2005). Glucose metabolism and oscillatory behavior of pancreatic islets. *Physical Review E*, 72(5), incorporated by reference herein in its entirety.

Equation Updates for EFS and PBM:
EFS Equations:
During the parameter updates, the membrane voltage changed by:

$$V(t+1) = V(t) + \frac{dV}{dt} + (E_m \cdot EFS)$$

$$E_m = \frac{1}{\pi} f_c \, r$$

Where EFS is the strength of the electric field set by the user in V/cm. $E_m$ being the coefficient derived explained in chapter 4 for assuming an average membrane depolarization, with $f_c$ being the spherical form factor (1.5) and r being the radius of the cell (7 μm).

This equation was derived from the equation given in: Schoenbach, K., et al. Ultrashort electrical pulses open a new gateway into biological cells. Proc. IEEE 92:1122-1137, 2004, incorporated by reference herein in its entirety.

PBM Equations:
The effects of PBM were via CCO activation utilized the equation:

$$J_{hres} = V_{me} F_{De} DF_{Ae} F_{Te}$$

With the basal $F_{Ae}$ being changed from 1.0 to 0.6 based on the activity of CCO at 50 nM nitric oxide concentration from: Poderoso, J., Carreras, M., Lisdero, C., Riobó, N., Schöpfer, F. and Boveris, A., 1996. Nitric Oxide Inhibits Electron Transfer and Increases Superoxide Radical Production in Rat Heart Mitochondria and Submitochondrial Particles. Archives of Biochemistry and Biophysics, 328 (1), pp. 85-92, incorporated by reference herein in its entirety.

The change in $F_{Ae}$ by PBM was determined by:

$$DF_{Ae} = F_{Ae}(1 + (1.6 A_e) - (0.9 A_e^2))$$

$$A_e = Abs_{CCO} PBM_{ir} \, EXP(10^{-3})$$

Where $DF_{Ae}$ is the updated $F_{Ae}$ under PBM, $Abs_{CCO}$ being the absorption of CCO for 810 nm light, $PBM_{ir}$ being the irradiance in (mW/cm²), EXP being the duration of PBM (s), and ($10^{-3}$) to convert to model units.

The change in CCO activity was interpolated via a 2nd order polynomial for the experimental data found here: Houreld, N., Masha, R. and Abrahamse, H., 2012. Low-intensity laser irradiation at 660 nm stimulates cytochrome c oxidase in stressed fibroblast cells. Lasers in Surgery and Medicine, 44(5), pp. 429-434, incorporated by reference herein in its entirety.

The effects of PBM on glucokinase activity modified the glucose consumption equation to:

$$J_{glu} = HKA\left(1 + \frac{((1.6 A_e) - (0.9 A_e^2))}{14}\right) V_{mglu} \left(\frac{[ATP]_i}{[ATP]_i + K_{mATP}}\right)\left(\frac{[Glu]^{hgl}}{[Glu]^{hgl} + K_{mgl}^{hgl}}\right)$$

Where HKA was the glucokinase fractional activity (1 at basal) with PBM's effects increasing it by at most 5%.

For TRPV1, the open fraction was manipulated by the user with the following equations added:

$$I_{TRPVCa} = G_{TRPVCa} PoTRPV(V - V_{ca})$$

$$I_{TRPVNa} = G_{TRPVNa} PoTRPV(V - V_{Na})$$

Where $I_{TRPVCa}$ and $I_{TRPVNa}$ are the TRPV currents for calcium and sodium respectively, $G_{TRPVCa}$ and $G_{TRPVNa}$ being the conductance values for TRPV for each ion, and PoTRPV being the open fraction for TRPV1 channels. This led to the change in the following differential equations:

$$\frac{d[Ca]_i}{dt} = f_i\left(\frac{-I_{VCa} + 2I_{NaCa} - 2I_{Capump} - I_{TRPVCa}}{2FV_i} - J_{ER} + \frac{J_{out}}{V_i} - \frac{d[Ca]_m}{dt}\right) - K_{sg}[Ca]_i$$

$$\frac{d[Na]_i}{dt} = \frac{-3I_{NaCa} - 3I_{NaK} - I_{Na} - I_{Cran} - I_{TRPVNa}}{FV_i}$$

Insulin Equations: Maximum insulin dynamic rates were found from the following paper: Rorsman, P. and Renström, E., 2003. Insulin granule dynamics in pancreatic beta cells. Diabetologia, 46(8), pp. 1029-1045, incorporated by reference herein in its entirety.

This led to the following if statement conditions:

if $R_r \geq I_t 1.4 \times 10^{-6}$ and $t \leq 300000$, then $R_r = I_t 1.4 \times 10^{-6}$ if $R_r \geq I_t 5.0 \times 10^{-7}$ and $t > 300000$, then $R_r = I_t 5.0 \times 10^{-7}$ else $R_r = \alpha_r(S_{max} - S_R)$

TABLE 1

Parameters for updated and custom equations.

| Parameter | Value | Reference |
|---|---|---|
| $f_c$ | 1.5 | A1 |
| r | 7 (μm) | A2 |
| $Abs_{CCO}$ | 0.06 | A3 |
| $PBM_{i_r}$ | User Defined | |
| EXP | User Defined | |
| $G_{TRPVCa}$ | 15 | A4 |
| $G_{TRPVNa}$ | 63 | A4 |
| $I_t$ | 0.0222 | A1 |

Thermal Simulation Equations:
The change in temperature in the cell was determined by:

$$\frac{dT_{cell}}{dt} = \frac{\alpha\, I_r\, A_c - h_c\, A_{sc}(T_{cell} - T_{med})}{m_c\, C_p}$$

Where α is water absorbance at 810 nm, $I_r$ is the irradiance (W/cm$^2$), $A_c$ is the cross-sectional area of the cell, $T_{cell}$ being the current cell temperature, $T_{med}$ being the current media temperature, $m_c$ being the mass of the cell, $A_{sc}$ being the cell's surface area, and $C_p$ being the specific heat of water.

For the change in temperature of the media:

$$\frac{dT_{med}}{dt} = \frac{\alpha\, I_r\, A_m - h_m\, A_{sm}(T_{med} - T_{sur})}{m_{med}\, C_p}$$

Where $A_m$ is the cross-sectional area of the media, $h_m$ is the convective heat loss to the surrounding environment, $T_{sur}$ is the environmental temperature, $A_{sm}$ being the exposed surface area, and $m_{med}$ being the mass of the media. Temperature values were in kelvin and mass in grams.

TABLE 2

Parameters for the thermal simulations.

| Parameter/Variable | Value/Initial Value | Reference |
|---|---|---|
| $T_{cell}$ | 300 | |
| $T_{med}$ | 300 | |
| $T_{sur}$ | 300 | |
| α | 0.04 | A5 |
| $I_r$ | Varied | |
| $A_c$ | 1.5394 × 10$^{-6}$ | |
| $A_m$ | 2.25 | |
| $h_c$ | 0.026 | A6 |
| $h_m$ | 0.005 | |
| $A_{sc}$ | 6.1575 × 10$^{-6}$ | |
| $A_{sm}$ | 2.25 | |
| $m_c$ | 1.44 × 10$^{-9}$ | |
| $m_{med}$ | 2 | |
| $C_p$ | 4.168 | |

What is claimed is:

1. An in vitro method of improving functionality of isolated islets or a group of β-cells comprising:
   pumping the isolated islets or the group of β-cells into a bioreactor system, wherein the bioreactor system comprises;
   a fluid chamber;
   a plurality of cell culture chambers in fluidic communication with the fluid chamber;
   a plurality of cell size sorters coupled to the plurality of cell culture chambers and configured to filter fluid into the plurality of cell culture chambers;
   a sorter inlet in fluidic communication with the fluid chamber;
   a sorted outlet in fluidic communication with the fluid chamber and apart from the sorter inlet;
   at least one electric field generator in electrical communication with at least one of the plurality of cell culture chambers;
   at least one light source in optical communication with the at least one of the plurality of cell culture chambers; and
   a perfusion pump in fluidic communication with the sorter inlet and configured to facilitate the flow of fluid into the fluid chamber;
   wherein the at least one electric field generator is configured to apply an electric field to at least one of the plurality of cell culture chambers, and
   wherein the at least one light source is configured to generate light in at least one of the plurality of cell culture chambers, wherein the light has a wavelength from about 600 nm to about 1000 nm; and
   applying the electric field to at least one of the plurality of cell culture chambers; and
   generating light into at least one of the plurality of cell culture chambers, wherein the electric field impulse is from about 5 min to 30 min in duration, wherein the electric field impulse is from about 1.0 to about 5.0 volts per centimeter, and
   wherein the electric field is applied and the light is generated simultaneously.

2. An in vitro method of improving functionality of isolated islets or a group of β-cells, comprising
   a) contacting the isolated islets or the group of β-cells with light, wherein the light has a wavelength from about 600 nm to about 1000 nm; and
   b) applying an electric field impulse to the isolated islets or the group of β-cells, wherein the electric field impulse is from about 5 min to 30 min in duration, and wherein the electric field impulse is from about 1.0 to about 5.0 volts per centimeter.

3. The method of claim 2, wherein steps a) and b) are applied simultaneously.

4. The method of claim 2, wherein the isolated islets or the group of β-cells form a cluster with a diameter ranging from about 20 μm to about 1000 μm.

5. The method of claim 2, wherein the isolated islets or the group of β-cells form a cluster with a diameter ranging from about 20 μm to about 100 μm.

6. The method of claim 2, wherein the electric field impulse is about 3.0 volts per centimeter.

7. The method of claim 2, wherein the electric field impulse is about 15 min in duration.

8. The method of claim 2, wherein the light has a wavelength about 810 nm.

9. The method of claim 2, wherein the isolated islets or the group of β-cells is in contact with the light for about 1 min.

10. The method of claim 2, wherein the light has an intensity of about 150 mW/cm$^2$.

11. The method of claim 2, wherein the group of β-cells are a group of primary β-cells.

12. The method of claim 2, wherein the isolated islets or the group of β-cells are differentiated from one or more stem cells.

13. The method of claim 12, wherein the one or more stem cells are one or more induced pluripotent stem cells (iPSCs).

14. A method of treating type 1 diabetes in a subject in need thereof, comprising
    i. stimulating isolated islets or a group of β-cells using the method of claim 2; and
    ii. administering to the subject a therapeutically effective amount of the isolated islets or the group of β-cells of step i).

15. The method of claim 14, wherein the isolated islets or the group of β-cells are derived from the subject.

16. The method of claim 14, wherein the isolated islets or the group of β-cells are not derived from the subject.

* * * * *